(12) United States Patent
Herr et al.

(10) Patent No.: US 10,393,701 B2
(45) Date of Patent: Aug. 27, 2019

(54) MICROFLUIDIC METHODS OF ASSAYING MOLECULE SWITCHING AND DEVICES FOR PRACTICING THE SAME

(71) Applicant: The Regents of the University of California, Oakland, CA (US)

(72) Inventors: Amy E. Herr, Oakland, CA (US); Augusto M. Tentori, Berkeley, CA (US); Alex J. Hughes, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 958 days.

(21) Appl. No.: 14/035,846

(22) Filed: Sep. 24, 2013

(65) Prior Publication Data

US 2014/0158537 A1 Jun. 12, 2014

Related U.S. Application Data

(60) Provisional application No. 61/710,988, filed on Oct. 8, 2012.

(51) Int. Cl.
*G01N 27/447* (2006.01)
*G01N 30/00* (2006.01)
*G01N 30/88* (2006.01)

(52) U.S. Cl.
CPC ....... *G01N 27/44795* (2013.01); *G01N 30/00* (2013.01); *G01N 2030/8831* (2013.01)

(58) Field of Classification Search
CPC ....... G01N 27/44756; G01N 27/44791; G01N 27/44795; G01N 30/00; G01N 2030/8831; G01N 33/558; G01N 33/559; G01N 33/561; G01N 33/563; B01L 3/502753; B01L 2300/1861
See application file for complete search history.

(56) References Cited

U.S. PATENT DOCUMENTS 6,818,112 B2 11/2004 Schneider et al.
6,974,526 B2 12/2005 Lee et al.
(Continued)

FOREIGN PATENT DOCUMENTS

WO 2010135364 A2 11/2010
WO 2011142781 A2 11/2011

OTHER PUBLICATIONS

Fan et al., "Nanofluidic proteomic assay for serial analysis of oncoprotein activation in clinical specimens" Nature Medicine, May 2009, 15(5):566-571.
(Continued)

*Primary Examiner* — Maris R Kessel
(74) *Attorney, Agent, or Firm* — Bret E. Field; Rudy J. Ng; Bozicevic, Field & Francis LLP

(57) ABSTRACT

Microfluidic methods of assaying molecule switching are provided. Aspects of the methods include microfluidically separating a sample containing the molecule of interest and then employing the resultant separation pattern to determine a switching characteristic of the molecule. Also provided are microfluidic devices, as well as systems and kits that include the devices, which find use in practicing embodiments of the methods. The methods, devices, systems and kits find use in a variety of different applications, such as analytical and diagnostic assays.

24 Claims, 26 Drawing Sheets

(56) References Cited

U.S. PATENT DOCUMENTS

| | | |
|---|---|---|
| 7,112,444 B2 | 9/2006 | Beebe et al. |
| 7,641,780 B2 | 1/2010 | Lee et al. |
| 7,754,150 B2 | 7/2010 | Wada et al. |
| 7,846,676 B2 | 12/2010 | Yang et al. |
| 7,935,308 B2 | 5/2011 | O'Neill et al. |
| 7,935,479 B2 | 5/2011 | O'Neill et al. |
| 7,935,489 B2 | 5/2011 | O'Neill et al. |
| 2004/0262160 A1 | 12/2004 | Schneider et al. |
| 2005/0155861 A1 | 7/2005 | Guzman |
| 2005/0269267 A1 | 12/2005 | Patton et al. |
| 2006/0029978 A1 | 2/2006 | O'Neill et al. |
| 2008/0009078 A1* | 1/2008 | O'Neill ............. B01L 3/502715 436/501 |
| 2013/0252282 A1* | 9/2013 | Zhou .................... C07K 14/001 435/69.7 |

OTHER PUBLICATIONS

He et al., "Automated microfluidic protein immunoblotting", Nature Protocols, Nov. 2010, 5(11):1844-1856.

Herr et al., "Photopolymerized Cross-Linked Polyacrylamide Gels for On-Chip Protein Sizing" Anal. Chem., Aug. 2004, 76(16):4727-4733.

Lerch et al., "Electrokinetic Fluid Control in Two-Dimensional Planar Microfluidic Devices" Anal. Chem., Oct. 2007, 79(19):7485-7491.

Lo et al., "Photopolymerized diffusion-defined polyacrylamide gradient gels for on-chip protein sizing" Lab on a Chip, Aug. 2008, 8(8):1273-1279.

\* cited by examiner

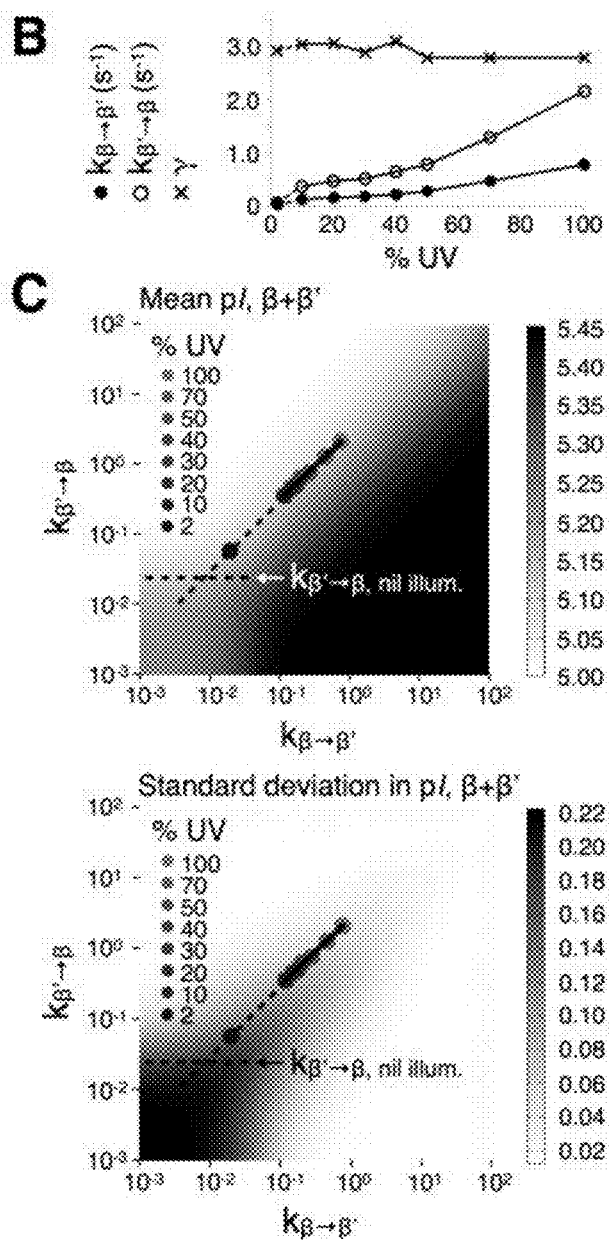
FIG. 26, continued

MICROFLUIDIC METHODS OF ASSAYING MOLECULE SWITCHING AND DEVICES FOR PRACTICING THE SAME

CROSS-REFERENCE TO RELATED APPLICATION

Pursuant to 35 U.S.C. § 119 (e), this application claims priority to the filing date of U.S. Provisional Patent Application Ser. No. 61/710,988 filed on Oct. 8, 2012, the disclosure of which is herein incorporated by reference.

REFERENCE TO GOVERNMENT SUPPORT

This invention was made with government support under grant number OD007294 awarded by the National Institutes of Health. The government has certain rights in the invention.

INTRODUCTION

A variety of analytical techniques may be used to separate and detect specific analytes in a given sample. A range of related immunoblotting methods have enabled the identification and semi-quantitative characterization of e.g., DNA (Southern blot), RNA (northern blot), proteins (Western blot), and protein-protein interactions (far-western blot); by coupling biomolecule separations and assays. For example, Western blotting can be used to detect proteins in a sample by using gel electrophoresis to separate the proteins in the sample followed by probing with antibodies specific for the target protein. In a typical Western blot, gel electrophoresis is used to separate native proteins by 3-D structure or denatured proteins by the length of the polypeptide. The proteins are then transferred to a membrane (typically nitrocellulose or PVDF), where they are probed (detected) using antibodies specific to the target protein.

Conventional blotting techniques, as discussed above, may fall short of performance needs for applications that demand either high-throughput sample analysis or operation in resource poor settings. Blotting techniques may require labor-intensive, time consuming, multi-step procedures carried out by a trained technician, and thus may be impractical for use in a clinical setting. Furthermore, devices that are less expensive and easier to fabricate and operate are desired.

SUMMARY

Microfluidic methods of assaying molecule switching are provided. Aspects of the methods include microfluidically separating a sample containing the molecule of interest and then employing the resultant separation pattern to determine a switching characteristic of the molecule. Also provided are microfluidic devices, as well as systems and kits that include the devices, which find use in practicing embodiments of the methods. The methods, devices, systems and kits find use in a variety of different applications, such as analytical and diagnostic assays.

BRIEF DESCRIPTION OF THE FIGURES

FIG. 2A shows a graph in which the top and middle traces are from the same experiment as FIGS. 1C-F, showing identical endogenous and probe relative fluorescence readouts respectively after electrophoretic washout of excess probe (traces offset in y-axis by 0.2 and 0.3 RFU respectively for clarity); inset shows correspondence of signals. The peak labeled "†" is a photoswitchable isoform with pI of 5.33. The bottom trace shows the immobilized endogenous GFP fluorescence profile for 120 sec pre-exposure of isoforms to blue light via a 10× objective in the focused state. FIG. 2B (bottom) shows an image of dynamic wtGFP pI 5.33 isoform photoswitching in 10× field of view upon application of blue light in dark, focused state (nominal [GFP]=617 nM). FIG. 2B (top) shows a graph of the switch-on of pI 5.33 isoform fluorescence indicating first-order kinetics with a time constant of 420 msec.

FIG. 3A shows a graph indicating defocusing of wtGFP (abrupt decrease in $E_{IEF}$ from 300 V cm$^{-1}$ to 0 V cm$^{-1}$) with inverse square root dependence of pI 5 and 5.19 isoform resolution on time (nominal [GFP]=617 nM). FIG. 3A (inset) shows GFP bands before and after the defocusing period, showing a decrease in resolution by diffusion. FIG. 3B shows a graph of capture efficiency η of 15 μM GFP under non-focusing conditions against spot UV exposure time fit to $$\eta = a\left(b - e^{-\frac{t}{\tau}}\right)$$

with τ=5.5 s (n=4). Maximum η was ~1.8% vs. <0.2% in BPMA− control gels. FIG. 3B (inset) shows images of the edges of separate microchannel UV exposure spots for several exposure times after washout of free GFP. FIG. 3C (top) shows a graph of ampholyte* η versus pH in BPMA+ and BPMA− separation media (η computed on the basis of the UV-exposed, refocused fluorescence profiles, [ampholyte*]=0.025% w/v, grey envelopes are ±SD, n=4). Peaks caused by pI marker bleaching artifacts are marked by black arrows. Native GFP* and PSA* efficiencies from separate chips are also shown (±SD, n=8 and 3 respectively). FIG. 3C (bottom) shows a graph of captured ampholyte* SNR after gradient washout. The dotted lines demarcate the approximate pH region of valid η data. FIG. 3D shows gel images showing immobilized ampholyte* after electrophoretic washout, accompanied by focused-state pI markers.

FIG. 4A shows images of a focused pI marker, primary (1°) and secondary (2°) fluorescent antibody probe signals for unlabeled purified PSA ([PSA]=500 nM). Integrated signal over pH region is marked by brackets used to construct calibration curve in FIG. 4B. FIG. 4B shows a calibration curve in nominal [PSA]=1-500 nM range (0.033-16.5 μg ml$^{-1}$, [1°, 2° pAb*]=0.1 μM for [PSA]=1-20 nM, [1°, 2° pAb*]=1 μM for [PSA]=50-500 nM, n=4 for all points except 5 nM, n=2). FIG. 4C (bottom) shows a graph of a comparison of signal after 1° and 2° probing for 500 nM PSA points. FIG. 4C (top) shows a graph of 2°:1° signal amplification ratio (dotted line marks baseline of nil 2° signal at 2°:1°=1, grey envelope was ±SD, n=4). FIG. 4D shows gel images of LAPC4 (PSA+) and DU145 (PSA−) 1° Ab* gel images (representative of 4 replicates per lysate, total protein concentration ~1 mg ml$^{-1}$ each). The integrated signal over the pH region marked by brackets was used in ELISA comparison.

FIGS. 5A and 5B show gel images of CE540-labeled PSA* in focused, captured/washed and probed states for monoclonal (FIG. 5A) and polyclonal Ab* (FIG. 5B) (all gel images were adjusted for identical contrast, [PSA*]=500 nM, [mAb*, pAb*]=1 μM). Electrophoretically washed data showed a lack of contribution to probe signals by immobilized PSA* detected on the same spectral channel. FIG. 5C shows a graph of 1° Ab* readouts aligned to corresponding focused PSA* traces. FIG. 5D shows a graph of probed:focused signal ratios adjusted by GFP capture efficiency (grey envelopes are ±SD, n=8 for each of mAb* and pAb* sets). FIG. 5E shows a graph of the ratio of pAb*:mAb* data from FIG. 5D.

FIG. 9A shows gel images of the effect of 10 sec flood UV exposure on ampholyte* profile in the focused state prior to washout. pI markers increased local ampholyte* bleaching (grey and black arrows). FIG. 9B shows a graph of ampholyte* signal retained after UV exposure. Troughs in pI marker regions are marked by black arrows. Higher overall bleaching occurred in the BPMA+ separation medium, which may be due to side reactions between ampholyte* radicals and other reactive species generated upon BPMA photoactivation.

FIG. 10 (top), solid lines are microplate green fluorescence data for analytes (1 μM each) in 50 μl aliquots of loading buffers titrated to the measured pH values shown with 2M HCl or NaOH. Data points at pH 9.9 are for washout buffer (wb) samples (see Table 1 for buffer compositions). $\varepsilon_{pHw=9.9,pHf\sim5}$ for GFP was approximated via the ratio of fluorescence values at the points indicated by short arrows. FIG. 10 (bottom) shows a graph of the corresponding red fluorescence values for each analyte, which shows a negligible dependence of CE540 fluorescence on pH for all labeled species.

FIG. 12A shows gel images of a comparison of purified PSA and GFP readouts in the subject microfluidic device to Novex slab gel (GFP visible in pI marker set). FIG. 12B shows gel mages of a PSA isoform pattern in a custom slab gel that agrees with major band assignments in the subject microfluidic device (gel buffer compositions here were identical to those in the subject microfluidic device).

FIG. 18A shows a schematic of a scalable-throughput, 10-60 min microfluidic method that includes: (i) analyte stacking and SDS-PAGE; (ii) band capture onto the separation medium; (iii) removal of SDS by brief electrophoretic washing; (iv) electrophoretic introduction of fluorescently-labeled primary and (optionally) secondary detection antibodies specific to target; and (v) washout of excess probe. Ultra-rapid assay readout was also enabled by dynamic probe imaging. FIG. 18B shows a continuous gel image over time of SDS-PAGE of fluorescently-labeled six protein ladder, completed in 60 s (4× magnification; band weights are 155, 98, 63, 40, 32, and 21 kDa). Channel aspect ratios were adjusted to produce gel-like images (see dimensions). (i) Transient isotachophoresis. (ii) SDS-PAGE. FIG. 18C shows fluorescence images and intensity for four ladder proteins photoimmobilized after SDS-PAGE (1 µM each, weights in kDa); before and after washout of uncaptured protein. At right, capture efficiency of bovine serum albumin (BSA, ±SD, n=3) for separation media fabricated chemically or photochemically. FIG. 18D shows a multiplexed micro-Western blot readout (red) in 40 min total assay times using primary antibodies for (i) ovalbumin (OVA), (ii) β-galactosidase (β-gal), OVA and trypsin inhibitor (TI), and (iii) β-gal, gp120, OVA, prostate specific antigen (PSA, 34 kDa) and TI (gp120, 200 nM; others antigens, 1 µM).

FIG. 19A shows a schematic of modular interfacing of microchips with a scalable electrode array. FIG. 19B shows 54 parallel micro-Western blots (18 samples in triplicate) of the four protein fluorescent ladder probed for ovalbumin (OVA) and β-galactosidase (β-gal) targets (1 µM each) with red fluorescent primary antibodies in 40 min total assay time. At top, total injected (inj.) fluorescence on weight marker spectral channel at the end of the ITP phase of SDS-PAGE acted as loading control. FIG. 19C shows fluorescence micrographs and plot of signal-to-noise ratio (SNR, ±SD, n=3) for electrophoretic introduction of red fluorescent primary antibody (Ab*) to OVA band at 4 min total assay time (arrow). FIG. 19D shows further probing of micro-Western blots from FIG. 19B with 10 nM alkaline phosphatase (AP)-conjugated donkey anti-goat IgG for specific amplification of the β-gal band. Electrophoretic introduction of 300 µM DiFMUP phosphatase substrate led to blue DiFMU product signal development upon stopped electric field. Dynamic fluorescence imaging compared β-gal peak SNR on red (primary antibody) and blue (DiFMU) fluorescence channels during this stopped field period.

FIG. 20A shows gel images of a 60 min micro-Western blot of 0.5 mg/ml transfected 293T lysate probed for NFκB with primary and fluorescently labeled secondary antibodies (red). Untransfected negative control lysate and loading controls (GAPDH and total injected fluorescence, inj.) were included. At right, the corresponding conventional 6-8 hr western blot readouts are shown for visual comparison. The conventional blot dimensions, "footprint" surface area was 800-fold larger than the micro-Western. FIG. 20B shows gel images of 40 min micro-Western blots of purified human immunodeficiency virus (HIV) proteins (reverse transcriptase, RT, 200 nM; gp120, 200 nM; p24, 1 µM) after probing targets with fluorescently labeled primary antibodies (red). FIG. 20C shows a graph of standard curves for NFκB and gp120 (±SD, n=3) constructed from the peak areas of the bands indicated by arrows in FIGS. 20A and 20B. gp120 is over the 5-200 nM range; NFκB is over 1:1 to 1:128 lysate dilution.

FIG. 21A shows a schematic of a conventional confirmatory HIV diagnostic assay. FIG. 21B shows gel images of the reactivity of 1:100-diluted strongly reactive (++), weakly reactive (+) and non-reactive control (−) human sera to gp120 (200 nM) and p24 (1 µM) "bait" proteins revealed by fluorescently-labeled secondary antibody to human IgG (red). At right, the conventional 6-1812 hr HIV western blot, with gp120- and p24-reactive bands indicated by arrows. The conventional blot used whole HIV lysate, whereas the micro-Western used specific HIV antigens, accounting for the additional reactive bands visible in the conventional blot.

FIG. 22(A) shows a schematic of reversible photobleaching upon UV illumination, which created dark GFP isoforms with increased pIs relative to their bright "parents". FIG. 22(B) shows a microfluidic chip with three parallel channels between each pair of access wells. Dynamic isoelectric photoswitching processes were monitored in real time, or isoforms were captured to the gel matrix and probed in situ with fluorescently labeled anti-GFP antibody (Ab*). FIG. 22(C) shows a schematic of avGFP chromophore and proton wire dynamics. Hydrogen bond networks allow proton exchange of the chromophore pocket with the external solvent. Glu222 was involved in excited state proton transfer (ESPT) with the chromophore Tyr66. The E222G mutation in acGFP inhibited ESPT and proton exchange with the internal wire. The dependence of reversible photobleaching magnitude on pH indicated involvement of a titratable residue, X, in the chromophore vicinity that affected chromophore protonation state by hydrogen bonding.

FIG. 23(A) shows static gel fluorescence images and electropherograms of immobilized avGFP isoforms (bright: α, β, γ; dark: α' and β'; γ' is below the assay limit of detection) within the microchannel (black; excitation 445-495 nm, emission 508-583 nm) after focusing under—top: nil light exposure conditions, bottom: 150 ms pre-exposure to 100% UV (270 mW cm$^{-2}$, 300-380 nm). Isoform capture was initiated immediately after the indicated pre-exposure protocol by 15 s UV irradiation of the gel under non-focusing conditions. Red fluorescence (excitation 525-555 nm, emission>575 nm) gel images and electropherograms were produced following pH gradient washout and gel probing with 600 nM Texas Red-labeled anti-GFP antibody for immobilized isoforms. The fluorescence of captured dark isoforms (α' and β') was switched on during imaging under blue illumination. FIG. 23(B) shoes the corresponding micrographs and electropherograms for immobilized acGFP isoforms (bright: δ, ε, ζ; dark: δ', ε' and ζ') probed with the same anti-GFP antibody.

FIGS. 24(A-C) show log-transformed fluorescence micrographs corrected for cathodic pH gradient drift showing dynamic isoelectric point evolution of avGFP isoforms during isoelectric focusing over time (100 ms streamed exposures, E=300 V cm$^{-1}$). Initial and final electropherograms in linear relative fluorescence units accompany each timelapse micrograph. The three panels show typical behavior upon applying a sequence of microchannel exposure conditions: FIG. 24(A) Nil-to-blue light exposure; FIG. 24(B) 100% UV exposure (excitation 300-380 nm, emission>410 nm); and FIG. 24(C) Blue light exposure. Delay between micrographs due to filter cube exchange was ~2 s.

FIG. 25(A) shows fluorescence photoswitching in avGFP and acGFP. Ten consecutive illumination cycles of 100% UV (1 s per cycle) and blue light (5 s per cycle) were conducted via 10× objective and total isoform fluorescence plotted over time for 10 ms frames. FIG. 25(B) shows fast reversible bleaching of isoforms under UV illumination. Left: Dark isoforms of avGFP were generated by pre-exposure of bands to 100% UV light for the indicated exposure times y, followed by a focusing equilibration period of 7 s under nil illumination. Focusing field was then halted and dark isoforms converted to the bright state by 3 s blue light exposure and quantified by measuring peak areas. Electropherograms showed an increase in dark isoform (α' and β') representation as a function of UV pre-illumination period. Right: Growth of dark state isoform peak areas in pI 5.25-5.6 range were determined from electropherogram data at left (black) and inferred by direct observation of bleaching under 100% UV (purple, from the first exposure cycle of (A)), both fit to RFU=a(1−e$^{-t/\tau}$)+b. FIG. 25(C) shows slow isoform fluorescence recovery under nil illumination. Left: Dark isoforms of avGFP were generated by 10 s pre-exposure of bands to 100% UV light via 10× objective, followed by a nil illumination period z of between 10 and 170 s. The focusing field was then halted and remaining dark isoforms were converted to the bright state by 3 s blue light exposure. Electropherograms showed decay in the representation of dark isoform (α' and β') peak areas in the pI 5.25-5.6 range as a function of nil illumination period. Right: Dark isoform peak areas fit to a single exponential of the form RFU=RFU$_{max}$e$^{-t/\tau}$ (±SD, n=3, error bar heights smaller than marker size).

FIG. 26(A) shows, at left, a sketch of concentration distributions from 1D model of focusing of bright (β) and dark (β') states of the major avGFP isoform over a range of interconversion rates; x-axes are pI 4.8-5.5, y-axes are arbitrary fluorescence units. κ/Pe compares reaction to focusing speeds, governing the observed morphology of the β peak during focusing. Concentration distributions of the bright and dark states can be distinct (κ/Pe<1) or overlapping (κ/Pe>1) depending on the UV intensity, even for the same equilibrium constant γ. Right hand column, least-squares fits of model distributions of β to experiment data for the indicated UV intensities. Fits from 10%-100% UV were global optima, while that at 2% assumed an average γ value from the other fits (square brackets and dashed lines denote this here and in FIGS. 26(B) and (C)). FIG. 26(B) shows interconversion rates between β and β' states and their ratio, γ, from fits in (A). FIG. 26(C) shows intensity plots of pI mean and standard deviation for the sum of β and β' distributions. Interconversion rates determined from experimental data in (B) are overlayed. Best-fit slope of 0.94 reflects approximately constant γ and mean pI across the UV range.

DETAILED DESCRIPTION

Figure 1:
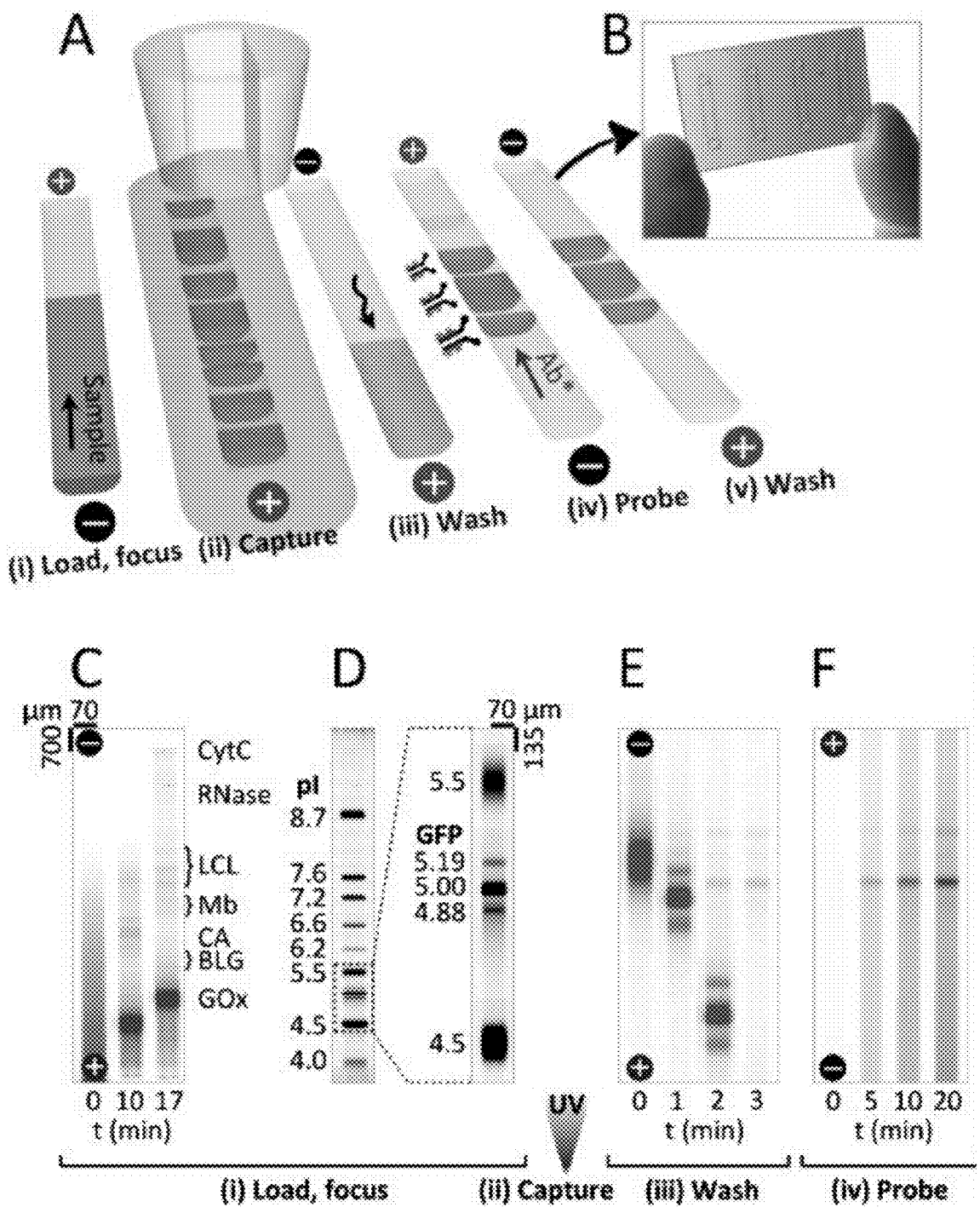
FIG. 1A shows a workflow illustration for a method according to embodiments of the present disclosure. The method includes: (i) electrophoretic loading and IEF of a heterogeneous sample, (ii) UV photoimmobilization of protein isoforms (grey bands), (iii) electrophoretic pH gradient washout, (iv) fluorescently labeled antibody probing of target antigen, and (v) washout of excess probe with specific fluorescence readout in an 80 min assay.
FIG. 1B shows a photograph of a microfluidic chip that includes 16 parallel separation media running between 4 pairs of access wells.
FIG. 1C shows images over time of IEF on CE540-labeled protein ladder mixed with wtGFP target in a single separation medium (red fluorescence imaging, nominal [ladder*]=0.38 mg ml$^{-1}$, ladder is CytC: cytochrome C, RNase: ribonuclease A, LCL: lentil lectin, Mb: myoglobin, CA: carbonic anhydrase, BLG: β-lactoglobulin, GOx: glucose oxidase, [GFP]=617 nM/16.7 μg ml$^{-1}$).
FIG. 1D shows spectrally resolved pI markers co-focused in the same channel as in FIG. 1C. Triplet peak pattern of wtGFP was detectable due to absorption in the UV.
FIG. 1E shows images over time of pH gradient washout after UV photoactivation of the separation medium monitored via endogenous green fluorescence of GFP, leaving gel-captured fraction behind.
FIG. 1F shows images over time of electrophoretic probing with 200 nM Texas Red-labeled pAb* to GFP.

Microfluidic methods of assaying molecule switching are provided. Aspects of the methods include microfluidically separating a sample containing the molecule of interest and then employing the resultant separation pattern to determine a switching characteristic of the molecule. Also provided are microfluidic devices, as well as systems and kits that include the devices, which find use in practicing embodiments of the methods. The methods, devices, systems and kits find use in a variety of different applications, such as analytical and diagnostic assays.

Microfluidic Devices

Aspects of the present disclosure include microfluidic devices for separating constituents of a fluid sample. A "microfluidic device" is device that is configured to control and manipulate fluids geometrically constrained to a small scale (e.g., sub-millimeter). Embodiments of the microfluidic devices include an elongated flow path and a separation medium. The separation medium may be configured to separate constituents in a sample from each other. In certain embodiments, the microfluidic device is configured to perform a method of assaying molecule switching as described in more detail below. For example, the microfluidic device may be configured to microfluidically separate a sample that includes a molecule to obtain a separation pattern, and determine a switching characteristic of the molecule from the switching pattern. In some instances, the separation medium may include functional groups that covalently bond to one or more constituents of interest in the separation medium upon application of an applied stimulus. The separated constituents may then be detected. Additional details about the separation medium are discussed below.

Separation Medium

In certain embodiments, the microfluidic devices include a separation medium. The separation medium may be configured to separate constituents of a sample from each other. In some cases, the separation medium is configured to separate constituents in a sample based on the physical properties of the constituents. For example, the separation medium may be configured to separate the constituents in the sample based on the molecular mass, size, charge (e.g., charge to mass ratio), isoelectric point, etc. of the constituents.

In certain instances, the separation medium is configured to separate the constituents in the sample based on the size and charge of the constituents. The separation medium may be configured to separate the constituents in the sample into distinct detectable bands of constituents. By "band" is meant a distinct detectable region where the concentration of a constituent is significantly higher than the surrounding regions. Each band of constituent may include a single constituent or several constituents, where each constituent in a single band of constituents has substantially similar physical properties, as described above.

In certain embodiments, the separation medium is configured to separate the constituents in a sample as the sample traverses the separation medium. In some cases, the separation medium is configured to separate the constituents in the sample as the sample flows through the separation medium. Aspects of the separation medium include that the separation medium has a directional axis. In some instances, the directional axis is oriented in the direction the sample travels as the sample traverses the separation medium. In some embodiments, the directional axis of the separation medium is aligned with the length of the separation medium. In these embodiments, the sample traverses the separation medium along the length of the separation medium. In some cases, the length of the separation medium is greater than the width of the separation medium, such as 2 times, 3 times, 4 times, 5 times, 10 times, 25 times, 50 times, 75 times, 100 times, 125 times, 150 times, 175 times, or 200 times or more the width of the separation medium.

In some instances, the separation medium is defined by a region of the microfluidic device that includes the separation medium. For example, the microfluidic device may include an elongated flow path. The elongated flow path may include the separation medium. For instance, the microfluidic device may include a channel (e.g., a microfluidic channel). The channel may include the separation medium. The separation medium may be included in the channel, such that a sample traverses the separation medium as the sample flows through the channel. In some instances, the length of the elongated flow path is greater than the width of the elongated flow path, such as 2 times, 3 times, 4 times, 5 times, 10 times, 25 times, 50 times, 75 times, 100 times, 125 times, 150 times, 175 times, or 200 or more times the width of the elongated flow path.

In certain embodiments, the separation medium includes a polymer, such as a polymeric gel. The polymeric gel may be a gel suitable for gel electrophoresis. The polymeric gel may include, but is not limited to, a polyacrylamide gel (e.g., methacrylamide gel), an agarose gel, and the like. The resolution of the separation medium may depend on various factors, such as, but not limited to, pore size, total polymer content (e.g., total acrylamide content), concentration of cross-linker, applied electric field, assay time, and the like. For instance, the resolution of the separation medium may depend on the pore size of the separation medium. In some cases, the pore size depends on the total polymer content of the separation medium and/or the concentration of cross-linker in the separation medium. In certain instances, the separation medium is configured to resolve analytes with molecular mass differences of 50,000 Da or less, or 25,000 Da or less, or 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a total acrylamide content, T (T=total concentration of acrylamide and bisacrylamide monomer), ranging from 1% to 20%, such as from 3% to 15%, including from 5% to 10%. In some instances, the separation medium has a total acrylamide content of 7.5%. In certain cases, the separation medium has a total acrylamide content of 6%.

In certain embodiments, the separation medium is configured to be formed from precursor moieties. For example, the separation medium may be a gel (e.g., a polyacrylamide gel) formed form gel precursors (e.g., polyacrylamide gel precursors, such as polyacrylamide gel monomers). The precursor moieties may be configured to react to form the separation medium. For instance, the gel precursors may be configured to react with each other to form the polyacrylamide gel separation medium. The reaction between the gel precursors may be activated by any suitable protocol, such as, but not limited to, chemical activation, light activation, etc. In some embodiments, the gel precursors are configured to be activated chemically, for example by contacting the gel precursors with an activation agent, such as, but not limited to, a peroxide. In some embodiments, the gel precursors are configured to be activated by light (i.e., photo-activated), for instance by contacting the gel precursors with light. The light may be of any wavelength suitable for activating the formation of the separation medium, and in some instances may have a wavelength associated with blue light in the visible spectrum. For example, the light used to activate formation of the separation medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the separation medium has a wavelength ranging from 465 to 475 nm. In some instances, the light used to activate formation of the separation medium has a wavelength of 470 nm.

In certain embodiments, the separation medium includes a buffer. The buffer may be any convenient buffer used for gel electrophoresis. In certain embodiments, the buffer is a Tris buffer. In certain embodiments, the separation medium includes a buffer, such as a Tris-glycine buffer. For example, the buffer may include a mixture of Tris and glycine.

In some cases, the buffer includes a detergent. In certain instances, the detergent is configured to provide analytes in the sample with substantially similar charge-to-mass ratios. Analytes with substantially similar charge-to-mass ratios may facilitate the separation of the analytes into one or more bands in the separation medium based on the molecular masses of the analytes in the sample. In certain cases, the detergent is anionic detergent configured to provide analytes in the sample with a charge, such as a negative charge. For example, the detergent may be an anionic detergent, such as, but not limited to, sodium dodecyl sulfate (SDS).

In certain embodiments, the separation medium is configured to separate the constituents in the sample based on the isoelectric point (pI) of the constituents (e.g., isoelectric focusing, IEF). In some cases, the separation medium includes a polymeric gel as described above. For example, the polymeric gel may include a polyacrylamide gel, an agarose gel, and the like. In certain instances, the polymeric gel includes a pH gradient, which, in some embodiments, is co-polymerized with the polymeric gel. In embodiments where the pH gradient is co-polymerized with the polymeric gel, the pH gradient may be substantially immobilized resulting in a separation medium having an immobilized pH gradient. In certain instances, the pH gradient includes a weak acid or a weak base (e.g., Immobilines), ampholytes, or the like.

In certain embodiments, the separation medium is configured to separate constituents in a sample based on size. For example, in some cases, the separation medium includes a polymeric gel having a pore size gradient. The pore size gradient may decrease along the directional axis of the separation medium. For example, the pore size gradient may have a pore size that decreases along the directional axis of the separation medium, such that a sample traversing the separation medium encounters progressively smaller and smaller pore sizes in the separation medium. As constituents in the sample traverse the pore size gradient, the constituents in the sample may be separated based on size. For example, larger constituents in the sample may be retained in the separation medium more readily than smaller constituents, which are able to traverse greater distances through the decreasing pore size gradient.

In some cases, the pore size of the separation medium depends on the total polymer content of the separation medium and/or the concentration of cross-linker in the separation medium. In certain instances, the separation medium pore size sufficient to resolve analytes with molecular mass differences of 50,000 Da or less, or 25,000 Da or less, or 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a pore size that depends on the total acrylamide content, T (T=total concentration of acrylamide and bisacrylamide monomer), where the total acrylamide content ranges from 1% to 20%, such as from 3% to 15%, including from 5% to 10%. In some instances, the separation medium has pore size defined by a total acrylamide content of 7.5%. In certain cases, the separation medium has a pore size defined by a total acrylamide content of 6%.

In certain embodiments, the support (e.g., separation medium) is configured to covalently bond to the constituents of interest. The covalent bond may be formed upon application of an applied stimulus. For example, the applied stimulus may include electromagnetic radiation, such as light. In some cases, the light is ultraviolet (UV) light. In some instances, the light used to covalently bond the constituents of interest to the separation medium has a wavelength ranging from 10 nm to 400 nm, such as from 50 nm to 400 nm, including from 100 nm to 400 nm, or from 150 nm to 400 nm, or from 200 nm to 400 nm, or from 250 nm to 400 nm, or from 300 nm to 400 nm, or form 325 nm to 375 nm, or from 350 nm to 365 nm. In certain cases, the light has a wavelength ranging from 350 to 365 nm.

In certain embodiments, the light used to covalently bond the constituents of interest to the separation medium has a wavelength different from the light used to activate formation of the separation medium. For example, as described above, the light used to activate formation of the separation medium may have a wavelength of blue light in the visible spectrum. As described above, the light used to covalently bond the constituents of interest to the separation medium may have a wavelength of UV light. As such, in certain embodiments, the separation medium is configured to be formed upon application of a first wavelength of light, and configured to covalently bond the constituents of interest upon application of a second wavelength of light. The first and second wavelengths of light may be blue light and UV light, respectively, as described above.

In some cases, the separation medium includes functional groups that covalently bond to the one or more constituents of interest. For example, the constituents of interest may be an analyte of interest, such as, but not limited to, a protein, a peptide, and the like. The functional groups may include functional groups that are activated upon application of an applied stimulus, such as electromagnetic radiation (e.g., light) as described above. As such, in certain instances, the functional groups are light-activatable functional groups. Upon application of light, the light-activatable functional groups may form a reactive species capable of forming covalent bonds, such as a radical alkyl intermediate. Examples of functional groups that may covalently bond to the constituents of interest upon application of an applied stimulus (e.g., light) include, but are not limited to, benzophenone groups, and the like. Once activated by the applied stimulus, the functional group may bond to the constituent of interest (e.g., protein or peptide) forming a covalent bond between the separation medium and the constituent of interest. For example, the functional group may form a carbon-carbon bond between the functional group and the constituent of interest.

In some embodiments, the functional groups are co-polymerized with the separation medium. For example, the functional groups may include a linker group that is attached to the separation medium. The functional group may be bound to the linker group at a first end of the linker group, and a second end of the linker group may be bound to the separation medium, thereby indirectly bonding the functional group to the separation medium. In some instances, the second end of the linker group, which is bound to the separation medium, includes a co-monomer, such as, but not limited to, an acrylamide co-monomer, and the like. In some embodiments, the second end of the linker group includes a methacrylamide co-monomer. In certain cases, the functional group is a benzophenone functional group and the linker group includes a co-monomer, such as an acrylamide co-monomer. For example, the functional group (including the linker group) may be N-(3-[(4-benzoylphenyl)formamido]propyl) methacrylamide (also known as BPMA or BPMAC). As described above, the linker group may have a first end bound to the functional group, and a second end bound to the separation medium. In some instances, the middle portion of the linker group between the first and second ends includes an aliphatic group, such as, but not limited to, a $C_1$-$C_{10}$ alkyl group. In certain cases, the middle portion of the linker group includes a lower alkyl group (e.g., a $C_1$-$C_6$ alkyl group). For instance, the middle portion of the linker group may include a propyl group.

In certain embodiments, the separation medium is configured to bind to constituents in a sample at a minimum capture efficiency. The capture efficiency is the percentage of constituents in the sample that are bound by the separation medium. In some instances, the capture efficiency, $\eta$, is the ratio of fluorescence measured after gradient washout ($AFU_w$) to the fluorescence during focusing ($AFU_f$), corrected by a factor $\varepsilon$ to account for the anticipated influence of pH on the species fluorescence signal. In certain embodiments, the separation medium is configured to have a capture efficiency of 1% or more, such as 5% or more, including 10% or more, or 20% or more, or 30% or more, or 40% or more, or 50% or more, or 60% or more, or 70% or more, or 80% or more, or 90% or more, or 95% or more. In some instances, the separation medium has a capture efficiency of 75% or more.

Further Aspects of Embodiments of the Microfluidic Devices

Aspects of the microfluidic devices include embodiments where the microfluidic device is configured to subject a sample to a flow field. By "flow field" is meant a region where components traverse the region in substantially the same direction. For example, a flow field may include a region where mobile components move through a medium in substantially the same direction. A flow field may include a medium, such as a separation medium, a loading medium, etc., where components, such as buffers, analytes, reagents, etc., move through the medium in substantially the same direction. A flow field may be induced by an applied electric field, a pressure differential, electroosmosis, and the like. In some embodiments, flow field may be directionally distinct.

For example, the flow field may be aligned with the directional axis of the separation medium. The flow field may be configured to direct the sample or constituents (e.g., analytes) through the elongated flow path containing the separation medium.

In certain embodiments, the microfluidic device is configured to subject a sample to an electric field. The electric field may facilitate the movement of the sample through the microfluidic device (e.g., electrokinetic transfer of the sample from one region of the microfluidic device to another region of the microfluidic device). The electric field may also facilitate the separation of the analytes in the sample by electrophoresis (e.g., polyacrylamide gel electrophoresis (PAGE), SDS-PAGE, isoelectric focusing, etc.), as described above.

For instance, the electric field may be configured to direct the analytes in a sample through the separation medium of the microfluidic device. The electric field may be configured to facilitate the separation of the analytes in a sample based on the physical properties of the analytes. For example, the electric field may be configured to facilitate the separation of the analytes in the sample based on the molecular mass, size, charge (e.g., charge to mass ratio), isoelectric point, etc. of the analytes. In certain instances, the electric field is configured to facilitate the separation of the analytes in the sample based on the molecular mass of the analytes. In other embodiments, the electric field is configured to facilitate separation of the analytes in the sample based on the isoelectric point (pI) of the analytes.

In some embodiments, the electric field may be directionally distinct. For example, the electric field may be aligned with the directional axis of the separation medium. The electric field may be configured to direct the sample or analytes through the separation medium along the directional axis of the separation medium.

In certain embodiments, the microfluidic device includes one or more electric field generators configured to generate an electric field. The electric field generator may be configured to apply an electric field to various regions of the microfluidic device, such as one or more of the separation medium, the loading medium, and the like. The electric field generators may be configured to electrokinetically transport the analytes and components in a sample through the various media in the microfluidic device. In certain instances, the electric field generators may be proximal to the microfluidic device, such as arranged on the microfluidic device. In some cases, the electric field generators are positioned a distance away from the microfluidic device. For example, the electric field generators may be incorporated into a system for use with the microfluidic device, as described in more detail below.

Embodiments of the microfluidic device may be made of any suitable material that is compatible with the assay conditions, samples, buffers, reagents, etc. used in the microfluidic device. In some cases, the microfluidic device is made of a material that is substantially inert (e.g., does not degrade or react) with respect to the samples, buffers, reagents, etc. used in the subject microfluidic device and methods. For instance, the microfluidic device may be made of materials, such as, but not limited to, glass, quartz, polymers, elastomers, paper, combinations thereof, and the like.

In some instances, the microfluidic device includes one or more sample input ports. The sample input port may be configured to allow a sample to be introduced into the microfluidic device. The sample input port may be in fluid communication with the separation medium. In some instances, the sample input port is in fluid communication with the upstream end of the separation medium. The sample input port may further include a structure configured to prevent fluid from exiting the sample input port. For example, the sample input port may include a cap, valve, seal, etc. that may be, for instance, punctured or opened to allow the introduction of a sample into the microfluidic device, and then re-sealed or closed to substantially prevent fluid, including the sample and/or buffer, from exiting the sample input port.

In certain embodiments, the microfluidic device is substantially transparent. By "transparent" is meant that a substance allows visible light to pass through the substance. In some embodiments, a transparent microfluidic device facilitates application of an applied stimulus (e.g., electromagnetic radiation, such as light, including visible light, UV light, etc.) to the separation medium. In certain cases, a transparent microfluidic device facilitates detection of analytes bound to the separation medium, for example analytes that include a detectable label, such as a fluorescent label.

In some aspects, the separation medium is provided in an elongated flow path, as illustrated in FIG. 1. In these embodiments, the microfluidic device includes a channel, such as a microfluidic channel. The channel may include the separation medium as described above. In certain embodiments, the elongated flow path includes an interior volume defined by the sides of the elongated flow path. For example, the elongated flow path may be a channel (e.g., a microfluidic channel), which may define an interior volume of the channel. In certain instances, the separation medium is provided in the interior volume of the elongated flow path. For instance, the separation medium may be provided in substantially the entire interior volume of the functional region of the elongated flow path. The functional region of the elongated flow path is the region used for separation and detection of the sample constituents and may not include other regions of the elongated flow path, e.g., for sample loading, buffer reservoirs, microfluidic fluid conduits, etc. As described above, the separation medium may be provided in substantially the entire interior volume of the functional region of the elongated flow path, such that the separation medium substantially fills the width of the interior volume of the elongated flow path. In these embodiments, the separation medium substantially fills the interior volume of the elongated flow path, such that there are no significant voids in the interior volume that do not include the separation medium. For instance, in these embodiments, the separation medium is not a coating on the interior surface of the elongated flow path, but rather the separation medium substantially fills the interior volume of the elongated flow path.

In addition to the separation medium, the microfluidic device may also include a loading medium. The loading medium may be in fluid communication with the separation medium. In some instances, the loading medium is in direct physical contact with the separation medium. For example, the loading medium may be bound to the separation medium, such as contiguously photopatterned with the separation medium. The loading medium may be positioned such that the sample contacts the loading medium before contacting the separation medium. For example, the loading medium may be positioned upstream from the separation medium in the elongated flow path. In certain embodiments, the loading medium facilitates contacting a sample with the separation medium. For instance, the loading medium may be configured to concentrate the sample before the sample contacts the separation medium. In certain embodiments, the loading medium may include two or more regions that have different physical and/or chemical properties. The loading medium may include a loading region and a stacking region. The loading medium may be configured to include a loading region upstream from a stacking region.

In certain embodiments, the loading medium includes a polymer, such as a polymeric gel. The polymeric gel may be a gel suitable for gel electrophoresis. The polymeric gel may include, but is not limited to, a polyacrylamide gel, an agarose gel, and the like. In some cases, the loading region includes a polymeric gel with a large pore size. For example, the loading region may include a polyacrylamide gel that has a total acrylamide content of 5% or less, such as 4% or less, including 3% or less, or 2% or less. In some instances, the loading region has a total acrylamide content of 3%.

In some cases, the stacking region of the loading medium may be configured to concentrate the sample before the sample contacts the separation medium. The stacking region may include a polymeric gel with a smaller pore size than the loading region. For example, the stacking region may include a polyacrylamide gel that has a total acrylamide content of ranging from 5% to 10%, such as from 5% to 9%, including from 5% to 8%, or from 6% to 8%. In some cases, the stacking region has a total acrylamide content of 7.5%. In some instances, the stacking region has a total acrylamide content of 6%. The smaller pore size of the stacking region, as compared to the loading medium, may slow the electrophoretic movement of the sample through the stacking region, thus concentrating the sample before it contacts the separation medium.

In certain instances, the channel contains the loading medium and the separation medium. The channel may be configured to contain the loading medium and the separation medium such that the loading medium and the separation medium are in fluid communication with each other, as described above. For example, the channel may include a contiguous polymeric gel monolith with various regions. Each region of the contiguous polymeric gel monolith may have different physical and/or chemical properties. The contiguous polymeric gel monolith may include a first region having a loading medium and a second region having a separation medium. The flow paths of each region of the polymeric gel monolith may be configured such that a sample first contacts the loading medium and then contacts the separation medium. For example, the flow paths of the loading medium and the separation medium may be substantially aligned with the directional axis of the elongated flow path of the microfluidic channel in the microfluidic device.

In certain embodiments, In some cases, the elongated flow path that includes the separation medium has a width of 1 mm or less, such as 500 μm or less, including 250 μm or less, or 200 μm or less, or 150 μm or less, or 100 μm or less, or 75 μm or less, or 50 μm or less, or 40 μm or less, or 30 μm or less, or 20 μm or less, or 10 μm or less. In some instances, the elongated flow path that includes the separation medium has a width of 70 μm. In some cases, the elongated flow path that includes the separation medium has a length ranging from 0.5 mm to 50 mm, such as from 0.5 mm to 25 mm, including from 1 mm to 20 mm, or from 5 mm to 15 mm. In certain embodiments, the elongated flow path that includes the separation medium has a length of 10 mm. In certain instances, the elongated flow path that includes the separation medium has a depth of 100 μm or less, such as 75 μm or less, including 50 μm or less, or 25 μm or less, or 20 μm or less, or 15 μm or less, or 10 μm or less, or 5 μm or less. In some instances, the elongated flow path that includes the separation medium has a depth of 10 μm. The dimensions of the separation medium itself may be similar to the widths, lengths and depths listed above.

Aspects of the microfluidic device also include embodiments that have two or more elongated flow paths, each of which includes a separation medium as described above. The two or more elongated flow paths may be arranged on the microfluidic device in parallel or in series. For instance, the two or more elongated flow paths may be arranged in parallel, which, in some embodiments, may facilitate the analysis of two or more samples simultaneously. Microfluidic devices may include 2 or more, such as 4 or more, including 8 or more, 12 or more, 16 or more, 20 or more, 24 or more, 36 or more, 54 or more, or 100 or more elongated flow paths arranged in parallel. In some cases, the two or more elongated flow paths may be arranged in series. For example, the microfluidic device may include a first elongated flow path and a second elongated flow path arranged in series. In some instances, arranging the elongated flow paths in series may facilitate the subsequent analysis of constituents in the sample that are not retained by the separation medium in the first elongated flow path.

In certain embodiments, the microfluidic device has a width ranging from 1 mm to 10 cm, such as from 5 mm to 5 cm, including from 5 mm to 1 cm. In some instances, the microfluidic device has a length ranging from 1 mm to 100 cm, such as from 1 mm to 50 cm, including from 5 mm to 10 cm, or from 5 mm to 1 cm. In certain aspects, the microfluidic device has an area of 1000 $cm^2$ or less, such as 100 $cm^2$ or less, including 50 $cm^2$ or less, for example, 10 $cm^2$ or less, or 5 $cm^2$ or less, or 3 $cm^2$ or less, or 1 $cm^2$ or less, or 0.5 $cm^2$ or less, or 0.25 $cm^2$ or less, or 0.1 $cm^2$ or less.

Further aspects related to microfluidic devices, separation media for microfluidic devices, and methods for using microfluidic devices are found in U.S. application Ser. No. 13/055,679, filed Jan. 24, 2011, the disclosure of which is incorporated herein by reference in its entirety.

FIG. 1B shows a photograph of a microfluidic device according to embodiments of the present disclosure. The microfluidic device may also include various microfluidic ports, such as access ports. For example, a pair of microfluidic ports may be associated with each channel, with a first port at an upstream end of the channel and a second port at a downstream end of the channel. As shown in the photograph in FIG. 1B, the microfluidic device may include multiple parallel channels that each contain a separation medium. One or more channels may be in fluid communication with each pair of access port, such as 1 channel, 2 channels, 3 channels, 4 channels, 5 channels, 6 channels, 7 channels, 8 channels, 9 channels, or 10 or more channels. In the embodiment shown in FIG. 1B, each pair of access ports has four corresponding channels that each contain a separation medium.

Methods

Embodiments of the methods are directed to separating constituents in a fluid sample. In certain embodiments of the methods, one or more constituents in the sample may be separated. The method includes separating a sample that includes a molecule of interest to obtain a separation pattern. In some instances, a microfluidic device as described above may be used to separate the sample, and thus the method includes microfluidically separating the sample that includes the molecule to obtain a separation pattern. In some instances, as described above, the separation medium is configured to separate the constituents in the sample based on an equilibrium separation technique. For example, the method may include microfluidically separating the sample using an equilibrium separation technique, such as, but not limited to isoelectric focusing (IEF). In these instances, the separation pattern produced corresponds to the pattern of separated constituents in the sample after performing the equilibrium separation technique (e.g., IEF). In other embodiments, the separation medium is configured to separate the constituents in the sample based on a non-equilibrium separation technique. For example, the method may include microfluidically separating the sample using a non-equilibrium separation technique, such as gel electrophoresis separation techniques, including, but not limited to, PAGE, SDS-PAGE, and the like. In these instances, the separation pattern produced corresponds to the pattern of separated constituents in the sample after performing the non-equilibrium separation technique (e.g., PAGE).

The method further includes determining a switching characteristic of the molecule from the separation pattern. By "switching characteristic" is meant a physicochemical property of the molecule that changes (i.e., switches) from a first state to a second state in response to an external stimulus. The switching characteristic may include any detectable physicochemical property of the molecule, such as, but not limited to, isoelectric point, charge, electrophoretic mobility, fluorescence, binding affinity, conformation, molecular weight, hydrophobicity, and the like. In some instances, the switching characteristic is the isoelectric point of the molecule of interest. In some cases, the switching characteristic is the charge of the molecule of interest. In some instances, the switching characteristic is a photoswitching characteristic, such as the fluorescence of the molecule of interest. By "photoswitching characteristic" is meant a physicochemical property of the molecule that changes (i.e., switches) from a first state to a second state in response to an external light stimulus. For example, the photoswitching characteristic may be a change between fluorescent and non-fluorescent states of the molecule. In some instances the change between fluorescent and non-fluorescent states of the molecule may depend on the light the molecule is exposed, such as the wavelength or intensity of the light the molecule is exposed to.

The external stimulus that induces the change in the switching characteristic of the molecule may include, but is not limited to light, temperature, binding/cleavage events (e.g., contacting the molecule with a ligand or protease, etc.), pH of the surrounding buffer medium, contacting the molecule with a detergent or denaturant (e.g., urea), and the like. In certain embodiments, the switching characteristic is a photoswitching characteristic and, thus, the external stimulus that induces the change in the photoswitching characteristic is light. In some instances, the photoswitching characteristic depends on the wavelength of the light. In certain cases, the photoswitching characteristic may change from a first state to a second state depending on the wavelength of the light the molecule is exposed to. For instance, the photoswitching characteristic may be in a first state upon exposure to a first wavelength of light, and may switch to a second state upon exposure to a second wavelength of light. As indicated above, the photoswitching characteristic may be a change between fluorescent and non-fluorescent states of the molecule. In some cases, the molecule may switch from a fluorescent state to a non-fluorescent state depending on the wavelength of the light the molecule is exposed to. For instance, the molecule may be in a fluorescent state upon exposure to a first wavelength of light, and may switch to a non-fluorescent state upon exposure to a second wavelength of light.

In certain embodiments, the method includes determining the switching characteristic of the molecule. The switching characteristic may be determined from the separation pattern of the sample after microfluidically separating the sample as described above (e.g., using IEF or PAGE, and the like). For example, the switching characteristic may be determined based on the isoelectric point of the molecule of interest, which in turn is detected using IEF as described above. In some cases, the isoelectric point of the molecule may change from a first state to a second state in response to an external stimulus (e.g., an external light stimulus). For example, the isoelectric point may change as the molecule switches from a fluorescent state to a non-fluorescent state as described above. In some instances the change between fluorescent and non-fluorescent states of the molecule also induces a change in the isoelectric point of the molecule. The change in isoelectric point of the molecule may correspondingly be detected using IEF. For example, a change in the separation pattern of the sample may be detected as the isoelectric point of the molecule switches from a first state to a second state in response to the external stimulus (e.g., external light stimulus). In some cases, the change in the separation pattern may be detected by a shift in the corresponding IEF band of the molecule of interest (see, e.g., FIG. 24). Other switching characteristics of the molecule of interest may similarly be detected as a detectable change in a corresponding physicochemical property of the molecule similar to the method described above.

In certain embodiments, the method includes determining a kinetic property of the switching characteristic of the molecule. For instance, the method may include determining the rate of change for the switching characteristic as the molecule switches from a first state to a second state. In some cases, the method may include determining the rate of change for the switching characteristic as the molecule switches from the second state to the first state. In some instances, the method includes determining the rate of photoswitching between fluorescent and non-fluorescent states as described above, or the rate of photoswitching between non-fluorescent and fluorescent states as described above. In some cases, the method includes determining the rate of switching between a first isoelectric point and a second isoelectric point as described above, or the rate of switching between the second isoelectric point and the first isoelectric point as described above.

In certain embodiments, the method includes determining a mechanism of the switching characteristic of the molecule. For example, the method may include determining the mechanism of photoswitching between fluorescent and non-fluorescent states. In some cases, the mechanism may be determined by detecting a change in a physicochemical property of the molecule as described above. For instance, the mechanism may be determined based on a change in the isoelectric point of the molecule in response to an external stimulus (e.g., an external light stimulus). In certain instances, the mechanism of the photoswitching characteristic may be determined from the separation pattern of the sample after microfluidically separating the sample as described above (e.g., using IEF or PAGE, and the like). For example, the mechanism of the switching characteristic may be determined based on the isoelectric point of the molecule of interest, which in turn is detected using IEF as described above. In some cases, the isoelectric point of the molecule may change from a first state to a second state in response to an external stimulus (e.g., an external light stimulus). In some cases, the isoelectric point may change as the molecule switches from a fluorescent state to a non-fluorescent state as described above. In some instances, the change between fluorescent and non-fluorescent states of the molecule also induces a change in the isoelectric point of the molecule. The change in isoelectric point of the molecule may correspondingly be detected using IEF. For example, a detected increase in the isoelectric point of a molecule upon exposure to an external stimulus may indicate a switching mechanism that includes proton uptake into the molecular structure. Vice versa, a detected decrease in the isoelectric point of the molecule may indicate a mechanism that includes proton expulsion from the molecular structure. A change in the separation pattern of the sample may be detected as the isoelectric point of the molecule switches from a first state to a second state in response to the external stimulus (e.g., external light stimulus). In some cases, the change in the separation pattern may be detected by a shift in the corresponding IEF band of the molecule of interest (see, e.g., FIG. 24), which may facilitate determination of the mechanism of switching characteristic as described above. The mechanisms of other switching characteristics of the molecule of interest may similarly be determined based on a detectable change in a corresponding physicochemical property of the molecule similar to the method described above.

In certain embodiments, the method may initially include the step of introducing a fluid sample into a microfluidic device that includes an elongated flow path as described above. Introducing the fluid sample into the microfluidic device may include contacting the sample with the separation medium, or in embodiments of the microfluidic devices that include a loading medium, contacting the sample with the loading medium. The method may further include separating the sample constituents in the separation medium to produce a separated sample, as described above. In some cases, the separated sample is produced by gel electrophoresis as the sample traverses the separation medium, as described above. In other cases, the separated sample is produced by isoelectric focusing in the separation medium. The separated sample may include distinct detectable bands of constituents (e.g., analytes), where each band includes one or more constituents that have substantially similar properties, such as molecular mass, size, charge (e.g., charge to mass ratio), isoelectric point, etc. depending on the type of separation performed.

After the constituents in the sample have been separated, the method may include determining the switching characteristic of the molecule as described above. In other embodiments, the method includes applying a stimulus to the separation medium to covalently bond the constituents to the separation medium before detecting the molecule of interest. In some cases, the applying the stimulus includes applying electromagnetic radiation to the separation medium. For instance, the method may include exposing the separation medium to light, such as, but not limited to, visible light, UV light, infrared light, etc. In certain cases, the method includes applying light (e.g., UV light) to the separation medium to covalently bond the constituents to the separation medium. Further aspects of the separation medium, devices and methods related to covalently bonding constituents in a sample to the separation medium are described in U.S. Application Publication No. 2012/0329040, filed Jun. 21, 2012, the disclosure of which is incorporated herein by reference in its entirety.

In certain embodiments, the light used to covalently bond the constituents of interest to the separation medium has a wavelength different from the light used to activate the switching characteristic of the molecule, and different from the wavelength of light used for formation of the separation medium. For example, as described herein, the light used to activate formation of the separation medium may have a wavelength of blue light in the visible spectrum. As described above, the light used to covalently bond the constituents of interest to the separation medium may have a wavelength of UV light. As such, in certain embodiments, the method includes exposing the separation medium to a first wavelength of light to form the separation medium, and exposing the separation medium to a second wavelength of light to covalently bond the constituents of interest to the separation medium. The first and second wavelengths of light may be blue light and UV light, respectively, as described herein.

In certain embodiments, the method includes determining whether an analyte of interest is present in a sample, e.g., determining the presence or absence of one or more analytes of interest in a sample. In some instances, the microfluidic devices are configured to detect the presence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which a measurement of the concentration of the analyte is provided to the user.

In certain embodiments, the method includes detecting an analyte of interest bound to the separation medium. Detectable binding of an analyte of interest to the separation medium indicates the presence of the analyte of interest in the sample. In some instances, detecting the analyte of interest includes contacting the analyte of interest with a label configured to specifically bind to the analyte of interest. The label can be any molecule that specifically binds to a protein or nucleic acid sequence or biomacromolecule that is being targeted (e.g., the analyte of interest). Depending on the nature of the analyte, the label can be, but is not limited to: single strands of DNA complementary to a unique region of the target DNA or RNA sequence for the detection of nucleic acids; antibodies against an epitope of a peptidic analyte for the detection of proteins and peptides; or any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the label includes an antibody. The antibody may specifically bind to the analyte of interest.

In certain embodiments, the label includes a detectable label. Detectable labels include any convenient label that may be detected using the methods and systems, and may include, but are not limited to, fluorescent labels, colorimetric labels, chemiluminescent labels, multicolor reagents, enzyme-linked reagents, avidin-streptavidin associated detection reagents, radiolabels, gold particles, magnetic labels, and the like. In certain embodiments, the label includes an antibody associated with a detectable label. For example, the label may include a labeled antibody (e.g., a fluorescently labeled antibody) that specifically binds to the analyte of interest. As such, the method may include detecting the labeled analyte of interest.

As described above, detecting the analyte of interest includes contacting the analyte of interest with a label configured to specifically bind to the analyte of interest (e.g., an antibody that specifically binds to the analyte of interest). For example, detecting the analyte of interest may include contacting the analyte of interest with a primary label that specifically binds to the analyte of interest. In certain embodiments, the method includes enhancing the detectable signal from the labeled analyte of interest. For instance, enhancing the detectable signal from the labeled analyte of interest may include contacting the primary label with a secondary label configured to specifically bind to the primary label. In certain instances, the primary label is a primary antibody that specifically binds to the analyte of interest, and the secondary label is a secondary antibody that specifically binds to the primary antibody. As such, enhancing the detectable signal from the labeled analyte of interest may include contacting the primary antibody with a secondary antibody configured to specifically bind to the primary antibody. The use of two or more detectable labels as described above may facilitate the detection of the analyte of interest by improving the signal-to-noise ratio.

Samples that may be assayed with the subject methods may include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analyte of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular mass, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like. In certain embodiments, the molecule of interest is a protein. In some cases, the protein is a fluorescent protein, such as, but not limited to, green fluorescent protein (GFP), enhanced green fluorescent protein (EGFP), yellow fluorescent protein (YFP) and yellow fluorescent protein derivatives (e.g., Citrine, Venus, Ypet, etc.), blue fluorescent protein (BFP) and blue fluorescent protein derivatives (e.g., EBFP, EBFP2, Azurite, mKalama1, etc.), cyan fluorescent protein (CFP) and cyan fluorescent protein derivatives (e.g., ECFP, Cerulean, CyPet, etc.), and the like. In certain instances, the fluorescent protein is GFP.

In certain embodiments, the method is configured to separate and/or detect constituents of interest in a sample, where the sample size is small. For example, the method may be configured to separate and/or detect constituents of interest in a sample, where the sample size is 1 mL or less, such as 750 μL or less, including 500 μL or less, or 250 μL or less, of 100 μL or less, or 75 μL or less, or 50 μL or less, or 40 μL or less, or 30 μL or less, or 20 μL or less, or 10 μL or less, or 5 μL or less, or 1 μL or less. In some instances, the method is configured to separate and/or detect constituents of interest in a sample, where the sample size is 20 μL or less.

In certain embodiments, the method includes concentrating, diluting, or buffer exchanging the sample prior to directing the sample through the separation medium. Concentrating the sample may include contacting the sample with a concentration medium prior to contacting the sample with the separation medium. The concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method includes contacting the separated analytes bound to the separation medium with a blocking reagent prior to detecting the analyte of interest. In some cases, contacting the separated analytes with a blocking reagent prior to detecting the analyte of interest may facilitate a minimization in non-specific binding of a detectable label to the separated analytes. For example, contacting the separated analytes with the blocking reagent prior to detecting the analyte of interest may facilitate a minimization in non-specific binding of a labeled antibody to the separated analytes. The blocking reagent can be any blocking reagent that functions as described above, and may include, but is not limited to, bovine serum albumin (BSA), non-fat dry milk, casein, and gelatin. In other embodiments, no blocking step is required. Thus, in these embodiments, the method does not include a blocking step prior to detecting the analyte of interest.

In certain embodiments, the method also includes optional washing steps, which may be performed at various times before, during and after the other steps in the method. For example, a washing step may be performed after binding the separated sample to the separation medium, after contacting the separated sample with the blocking reagent, after contacting the separated sample with the detectable label, etc.

Embodiments of the method may also include releasing the analyte bound to the separation medium. The releasing may include contacting the bound analyte with a releasing agent. The releasing agent may be configured to disrupt the binding interaction between the analyte and the separation medium. In some cases, the releasing agent is a reagent, buffer, or the like, that disrupts the binding interaction between the analyte and the separation medium causing the separation medium to release the analyte. After releasing the analyte from the separation medium, the method may include transferring the analyte away from the separation medium. For example, the method may include directing the released analyte downstream from the separation medium for secondary analysis with a secondary analysis device such as, but is not limited to, a UV spectrometer, and IR spectrometer, a mass spectrometer, an HPLC, an affinity assay device, a second microfluidic device as described herein, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular mass, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes. In certain embodiments, multiplex analysis also includes the use of two or more different detectable labels. The two or more different detectable labels may specifically bind to the same or different analytes. In some cases, the two or more different detectable labels may specifically bind to the same analyte. For instance, the two or more different detectable labels may include different antibodies specific for different epitopes on the same analyte. The use of two or more detectable labels specific for the same analyte may facilitate the detection of the analyte by improving the signal-to-noise ratio. In other cases, the two or more different detectable labels may specifically bind to different analytes. For example, the two or more detectable labels may include different antibodies specific for epitopes on different analytes. The use of two or more detectable labels each specific for different analytes may facilitate the detection of two or more respective analytes in the sample in a single assay.

In certain embodiments, the method is an automated method. As such, the method may include a minimum of user interaction with the microfluidic devices and systems after introducing the sample into the microfluidic device. For example, the steps of separating the sample constituents in the separation medium to produce a separated sample and applying the stimulus to the separation medium to covalently bond the constituents to the separation medium may be performed by the microfluidic device and system, such that the user need not manually perform these steps. In some cases, the automated method may facilitate a reduction in the total assay time. For example, embodiments of the method, including the separation and detection of analytes in a sample, may be performed in 120 minutes or less, such as 90 minutes or less, or 60 minutes or less, or 45 minutes or less, or 30 minutes or less, such as 20 minutes or less, including 15 minutes or less, or 10 minutes or less, or 5 minutes or less, or 2 minutes or less, or 1 minute or less.

FIG. 1A shows a workflow illustration of an embodiment of a method for separating constituents of a fluid sample. In the embodiment shown in FIG. 1A, the method includes isoelectric focusing (IEF) of the sample constituents followed by post-separation binding to the separation medium and, finally, detection using a labeled antibody probe. Analytes are identified in situ by specific affinity interactions. In step (i) of FIG. 1A, a sample is contacted with the separation medium. After the sample is contacted with the separation medium, an electric field is applied along the directional axis of the separation medium to focus constituents in the sample based on the isoelectric point (pI) of the constituents. In step (ii) of FIG. 1A, the various analytes in the sample constituents have been separated by IEF in the separation medium, and the separation medium is exposed to UV light to covalently bond the constituents to the separation medium. In step (iii) of FIG. 1A, the separation medium is washed, for example to wash out the pH gradient used for IEF from the separation medium. In step (iv) of FIG. 1A, a detectable label (e.g., a fluorescently labeled antibody) is contacted with the separated analytes bound to the separation medium. The detectable label specifically binds to the analyte of interest (e.g., the target protein). Unbound label is washed away to facilitate a reduction in background signal (step (v) of FIG. 1A). A positive detection of the detectable label indicates the presence of the analyte of interest in the sample.

Aspects of embodiments of the methods may also include methods of producing a separation medium in a flow path. The method of producing the separation medium in the flow path may include providing precursor moieties in the flow path. For instance, the flow path may be filled with the precursor moieties (e.g., gel precursors, such as polyacrylamide gel precursors). In some cases, the method includes activating the precursor moieties to form the separation medium. For example, activating the gel precursors may include chemically activating the gel precursors by contacting the gel precursors with an activation agent, such as, but not limited to, a peroxide. In certain cases, activating the gel precursors includes photo-activating the gel precursors by contacting the gel precursors with light. As described above, the light used to activate formation of the separation medium may have a wavelength of blue light in the visible spectrum. For instance, the light used to activate formation of the separation medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the separation medium has a wavelength ranging from 465 to 475 nm. In some instances, the light used to activate formation of the separation medium has a wavelength of 470 nm.

Systems

Aspects of certain embodiments include a system for separating constituents in a fluid sample. In some instances, the system includes a microfluidic device as described herein. The system may also include a source of electromagnetic radiation (i.e., an electromagnetic radiation source). In certain embodiments, the system includes a module configured to perform a method of assaying molecule switching as described in more detail below. For example, the module may be configured to determine a switching characteristic of a molecule from a switching pattern produced by microfluidically separating a sample that includes the molecule using a microfluidic device as described herein.

In certain embodiments, the module includes a processor. The processor may be configured to execute programming that includes instructions for controlling the system to perform one or more of the steps in the method described herein. For instance, the processor may be configured to execute programming that includes instructions for determining a switching characteristic of a molecule from a switching pattern produced by microfluidically separating a sample that includes the molecule using a microfluidic device as described herein.

In certain embodiments, the electromagnetic radiation source is a light source. For example, the light source may include a visible light source, a UV light source, an infrared light source, etc. In some instances, the electromagnetic radiation source includes a light source, such as a UV light source. As described above, the electromagnetic radiation source may be used to apply electromagnetic radiation to the separation medium in the microfluidic device to covalently bond sample constituents to the separation medium.

In certain embodiments, the system also includes a detector. In some cases, the detector is a detector configured to detect a detectable label. The detector may include any type of detector configured to detect the detectable label used in the assay. As described above, detectable label may be a fluorescent label, colorimetric label, chemiluminescent label, multicolor reagent, enzyme-linked reagent, avidin-streptavidin associated detection reagent, radiolabel, gold particle, magnetic label, etc. In some instances, the detectable label is a fluorescent label. In these instances, the detector may be configured to contact the fluorescent label with electromagnetic radiation (e.g., visible, UV, X-ray, etc.), which excites the fluorescent label and causes the fluorescent label to emit detectable electromagnetic radiation (e.g., visible light, etc.). The emitted electromagnetic radiation may be detected by the detector to determine the presence of the labeled analyte bound to the separation medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

Systems of the present disclosure may include various other components as desired. For example, the systems may include fluid handling components, such as microfluidic fluid handling components. The fluid handling components may be configured to direct one or more fluids through the microfluidic device. In some instances, the fluid handling components are configured to direct fluids, such as, but not limited to, fluid samples, buffers (e.g., electrophoresis buffers, wash buffers, release buffers, etc.), and the like. In certain embodiments, the microfluidic fluid handling components are configured to deliver a fluid to the separation medium of the microfluidic device, such that the fluid contacts the separation medium. The fluid handling components may include microfluidic pumps. In some cases, the microfluidic pumps are configured for pressure-driven microfluidic handling and routing of fluids through the microfluidic devices and systems disclosed herein. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less, or 5 µL or less, or 1 µL or less.

In certain embodiments, the systems include one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the separation medium. In some cases, the applied electric field may be aligned with the directional axis of the separation medium. As such, the applied electric field may be configured to electrokinetically transport the analytes and components in a sample through the separation medium. In some instances, the electric field generators are configured to apply an electric field with a strength ranging from 10 V/cm to 1000 V/cm, such as from 100 V/cm to 800 V/cm, including from 200 V/cm to 800 V/cm, or from 400 v/cm to 800 V/cm.

In certain embodiments, the system includes an electric field generator configured to apply an electric field such that analytes and/or constituents in the sample are isoelectrically focused in the separation medium. For instance, an applied electric field may be aligned with the directional axis of the separation medium and configured to isoelectrically focus the sample constituents along the directional axis of the separation medium.

In certain embodiments, the subject system is a biochip (e.g., a biosensor chip). By "biochip" or "biosensor chip" is meant a microfluidic system that includes a substrate surface which displays two or more distinct microfluidic devices on the substrate surface. In certain embodiments, the microfluidic system includes a substrate surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., devices) may be separated by intervening spaces. Any given substrate may carry one, two, four or more arrays disposed on a front surface of the substrate. Depending upon the use, any or all of the arrays may be the same or different from one another and each may contain multiple distinct microfluidic devices. An array may contain one or more, including two or more, four or more, eight or more, 10 or more, 25 or more, 50 or more, or 100 or more microfluidic devices. In certain embodiments, the microfluidic devices can be arranged into an array with an area of 100 cm$^2$ or less, 50 cm$^2$ or less, or 25 cm$^2$ or less, 10 cm$^2$ or less, 5 cm$^2$ or less, such as 1 cm$^2$ or less, including 50 mm$^2$ or less, 20 mm$^2$ or less, such as 10 mm$^2$ or less, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

Arrays of microfluidic devices may be arranged for the multiplex analysis of samples. For example, multiple microfluidic devices may be arranged in series, such that a sample may be analyzed for the presence of several different analytes in a series of microfluidic devices. In certain embodiments, multiple microfluidic devices may be arranged in parallel, such that two or more samples may be analyzed at substantially the same time.

Aspects of the systems include that the microfluidic devices may be configured to consume a minimum amount of sample while still producing detectable results. For example, the system may be configured to use a sample volume of 100 μL or less, such as 75 μL or less, including 50 μL or less, or 25 μL or less, or 10 μL or less, for example, 5 μL or less, 2 μL or less, or 1 μL or less while still producing detectable results. In certain embodiments, the system is configured to have a detection sensitivity of 1 nM or less, such as 500 pM or less, including 100 pM or less, for instance, 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 μg/mL or less, such as 500 ng/mL or less, including 100 ng/mL or less, for example, 10 ng/mL or less, or 5 ng/mL or less, such as 1 ng/mL or less, or 0.1 ng/mL or less, or 0.01 ng/mL or less, including 1 pg/mL or less. In certain embodiments, the system has a dynamic range from $10^{-18}$ M to 10 M, such as from $10^{-15}$ M to $10^{-3}$ M, including from $10^{-12}$ M to $10^{-6}$ M.

In some cases, the system is configured to have a signal-to-noise ratio (SNR) of 10 or more, such as 15 or more, including 20 or more, or 30 or more, or 40 or more, or 50 or more, or 60 or more, or 70 or more, or 80 or more, or 90 or more, or 100 or more, or 150 or more, or 200 or more, or 500 or more, or 1,000 or more, or 2,000 or more, or 3,000 or more, or 4,000 or more, or 5,000 or more, or 6,000 or more, or 7,000 or more, or 8,000 or more, or 9,000 or more, or 10,000 or more. In some cases, the achievable signal-to-noise ratio depends on the method of detection used in the assay. For example, in certain embodiments the analyte of interest is directly labeled with a detectable label. In these embodiments, the signal-to-noise ratio may be 10 or more, such as 15 or more, including 20 or more, or 30 or more, or 40 or more, or 50 or more, or 60 or more, or 70 or more, or 80 or more, or 90 or more, or 100 or more, or 150 or more, or 200 or more. In other embodiments, the analyte of interest is first labeled with a primary label (e.g., a primary antibody) and then the primary label is labeled with a secondary label (e.g., a secondary antibody). In these embodiments, the signal-to-noise ratio may be 100 or more, such as 150 or more, including 200 or more, or 500 or more, or 1,000 or more, or 2,000 or more, or 3,000 or more, or 4,000 or more, or 5,000 or more, or 6,000 or more, or 7,000 or more, or 8,000 or more, or 9,000 or more, or 10,000 or more.

In certain embodiments, the microfluidic devices are operated at a temperature ranging from 1° C. to 100° C., such as from 5° C. to 75° C., including from 10° C. to 50° C., or from 20° C. to 40° C. In some instances, the microfluidic devices are operated at a temperature ranging from 35° C. to 40° C.

Utility

The subject devices, systems and methods find use in a variety of different applications where the determination of characteristics related to molecule switching is desired. For example, the dynamic and probed IEF assays described herein find use in analytical screening and quantitative kinetic analysis of photoswitching and other charge switching processes in response to stimuli including light, temperature, binding/cleavage events (e.g., contacting the molecule with a ligand or protease, etc.), pH of the surrounding buffer medium, contacting the molecule with a detergent or denaturant (e.g., urea), and the like. The subject devices, systems and methods also find use in other equilibrium and non-equilibrium separations and other switching processes where a different property is altered from switching (e.g., electrophoretic mobility altered due to ligand binding/unbinding during polyacrylamide gel electrophoresis (PAGE)).

The subject devices, systems and methods also find use in the measurement of dynamic protein reaction processes in real time. For example, the subject devices, systems and methods may be used to determine dynamic protein processes, including the photophysics of fluorescent proteins. Dynamic IEF analysis as described herein may be used to resolve and track fluorescent protein populations through physicochemical properties rather than by traditional fluorescence or static crystallographic measurements. As such, the subject devices, systems and methods find use in probing the chemical and structural nature of conformational photoswitching processes. The subject devices, systems and methods find use in the analysis of a range of fluorescent and other light-reactive proteins. For example, the ability to characterize GFP constructs genetically encoded with light-switchable charge may be used for a broad range of applications, such as the study of cellular membrane transport processes and the rational engineering of electrostatic aggregation in signaling molecule or metabolic networks. The subject devices, systems and methods find use in the study of reversible fluorescence (and thus isoelectric point) photoswitching at pH values in the vicinity of the fluorescence $pK_a$s of GFPs, which indicates that mutants developed as sensitive pH indicators in the physiologic range may be used for achieving maximum charge switching in biological systems. Other photoactivatable GFPs (e.g., Dronpa, Padron0.9 and PA-GFP, and the like) may also find use as described above.

Charge-switchable proteins may also find use in the engineering of biomimetic smart materials with light-actuated transitions in zeta potential, hydrophilicity/wetting behavior, and adhesion properties. The subject devices, systems and methods for dynamic IEF also find use in high-throughput screening for rational or directed tuning of photoactivatable protein phenomena, such as reversible photochromism and light-induced protein-protein interactions. The subject devices, systems and methods for dynamic and probed IEF assays also find use in analytical screening and quantitative kinetic analysis of photoswitching and other charge switching processes in response to stimuli including light, temperature, or binding/cleavage events.

The subject devices, systems and methods described herein can also be used with other equilibrium separations such temperature gradient focusing (TGF), isotachophoresis (ITP), and non-equilibrium separation techniques such as PAGE, chromatography, etc. In addition to photoswitching, the switching mechanism can be any other that alters physicochemical properties screened in the separation (examples include cleavage, ligand association/dissociation, etc.). The property altered can be different than pI, for example charge, molecular weight, conformation, electrophoretic mobility, hydrophobicity, etc. The switching can also be modulated by other external stimuli such as temperature, introduction of ligand, proteases, detergent, urea, etc. The switching could also occur spontaneously, such as a protein adopting different conformation states during electromigration.

Analyte probing and visualization can be done with reagents other than antibodies such as affibodies, aptamers, dyes, enzyme conjugates, etc. Readout methods other than fluorescence such as contactless conductance, absorbance, etc. can be used to determine band morphology during separation or after immobilization.

The subject devices, systems and methods find use in the determination of the presence or absence, and/or quantification of one or more analytes in a sample. For example, the subject devices, systems and methods find use in the separation and detection of proteins, peptides, nucleic acids, and the like. In some cases, the subject devices, systems and methods find use in the separation and detection of proteins.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the mass and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a microfluidic device as described in detail herein. The kits may further include a buffer. For instance, the kit may include a buffer, such as an electrophoresis buffer, a sample buffer, and the like. In certain cases, the buffer is an electrophoresis buffer, such as, but not limited to, a Tris buffer, a Tris-glycine, and the like. In some instances, the buffer includes a detergent (such as sodium dodecyl sulfate, SDS).

The kits may further include additional reagents, such as but not limited to, release reagents, denaturing reagents, refolding reagents, detergents, detectable labels (e.g., fluorescent labels, colorimetric labels, chemiluminescent labels, multicolor reagents, enzyme-linked reagents, detection reagents (e.g., avidin-streptavidin associated detection reagents), calibration standards, radiolabels, gold particles, magnetic labels, etc.), and the like.

In certain embodiments, the kits include a detectable label. The detectable label may be associated with a member of a specific binding pair. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the member of the specific binding pair includes an antibody. The antibody may specifically bind to an analyte of interest in the separated sample bound to the separation medium. For example, the detectable label may include a labeled antibody (e.g., a fluorescently labeled antibody) that specifically binds to the analyte of interest.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric.

EXAMPLES

Example 1

1. Multi-Stage, Single-Channel Assay Under Programmable Electrophoretic Control

The microfluidic device included a single microchannel housing a photoactive polyacrylamide gel matrix to integrate three assay stages (FIG. 1A): Separation—(i) sample loading and isoelectric focusing; Photocapture—(ii) UV exposure to covalently attach IEF-resolved protein isoforms to the separation medium followed by (iii) electrophoretic mobilization and washout of uncaptured species; and Probing—(iv) electrophoretic-introduction of antibody to the immobilized protein bands and (v) electrophoretic washout of unbound detection antibodies. Two or more microfluidic devices can be run in parallel on a single microfluidic chip (FIG. 1B).

In the first stage of the assay, proteinaceous samples were prepared and loaded in an ampholyte buffer titrated to the alkaline limit of the buffering range (~pH 10 for Pharmalyte 3-10) to minimize electrophoretic loading bias. After addition of anolyte and catholyte to the terminal reservoirs, an electric field was applied and IEF focused the analytes at channel positions determined by the pI of the analyte relative to the axial pH gradient. Recombinant wtGFP was included in the unlabeled protein mixture as a loading and immobilization standard along with a mixture of fluorescent pI marker peptides that absorb in the UV. Stepped ramping of the applied electric field (50 to 300 V cm$^{-1}$ in 50-100 V cm$^{-1}$ increments) yielded focusing of analytes in <20 min (FIGS. 1C and 1D). Analysis of the pI marker peptides indicated that repeatable, linear pH gradients were achieved (y=10.8–7.53x, where x is the fractional channel distance from the cathode; within-chip % RSD in slope of 6.5%, n=16, $R^2$>0.99 for all fits over pH 4-8.7 range).

Figure 6:
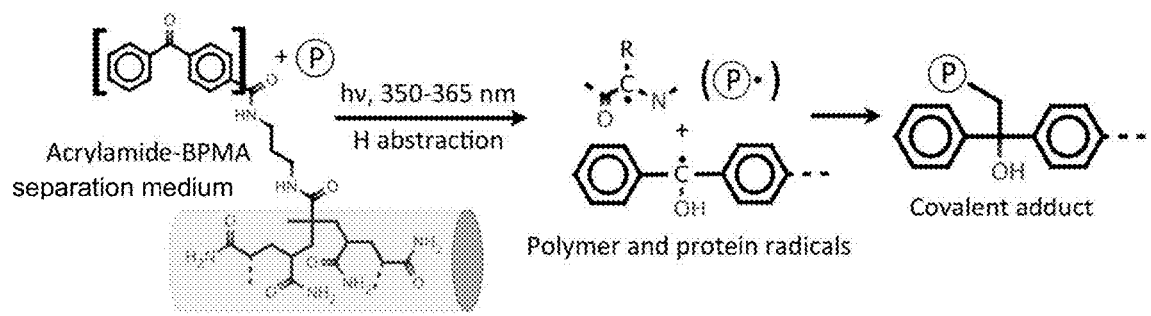
FIG. 6 shows a reaction scheme of a light-activated covalent bonding reaction between the carbonyl functional groups of a benzophenone methacrylamide (BPMA) monomer and target polypeptide, according to embodiments of the present disclosure.
Figure 7:
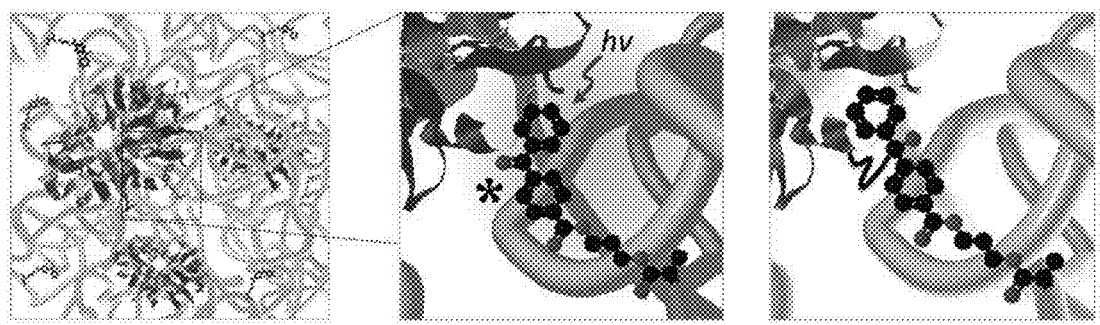
FIG. 7 shows a molecular model of a reaction scheme of a light-activated covalent bonding reaction between the carbonyl functional groups of a benzophenone methacrylamide (BPMA) monomer and target polypeptide, according to embodiments of the present disclosure.

The second stage of the assay was a transition between the IEF and immunoprobing stage, with the immunoprobing taking place in situ (i.e., no transfer of sample to a blotting membrane). The separation medium containing the focused analytes was exposed to UV light (350-365 nm, 10 sec), which induced photoimmobilization of analytes by the light-activatable copolymer gel matrix. Exposure to UV promoted the carbonyl groups of the benzophenone methacrylamide (BPMA) monomer termini to an electrophilic triplet state, $T_1^*$. Subsequent hydrogen abstraction was preferential towards C—H bonds in target polypeptides (Ⓟ) and other buffer constituents, leading to formation of stable covalent linkages to the gel matrix (see FIG. 6 and FIG. 7).

After UV exposure, uniform pH buffer conditions were recovered by chemical mobilization and washout of the pH gradient from the channel. Chemical mobilization was initiated by applying glycine buffer (pH 9.9) and an electric field at the access wells, resulting in elution of uncaptured species into the anodic well within 20 min (FIG. 1E).

Figure 2:
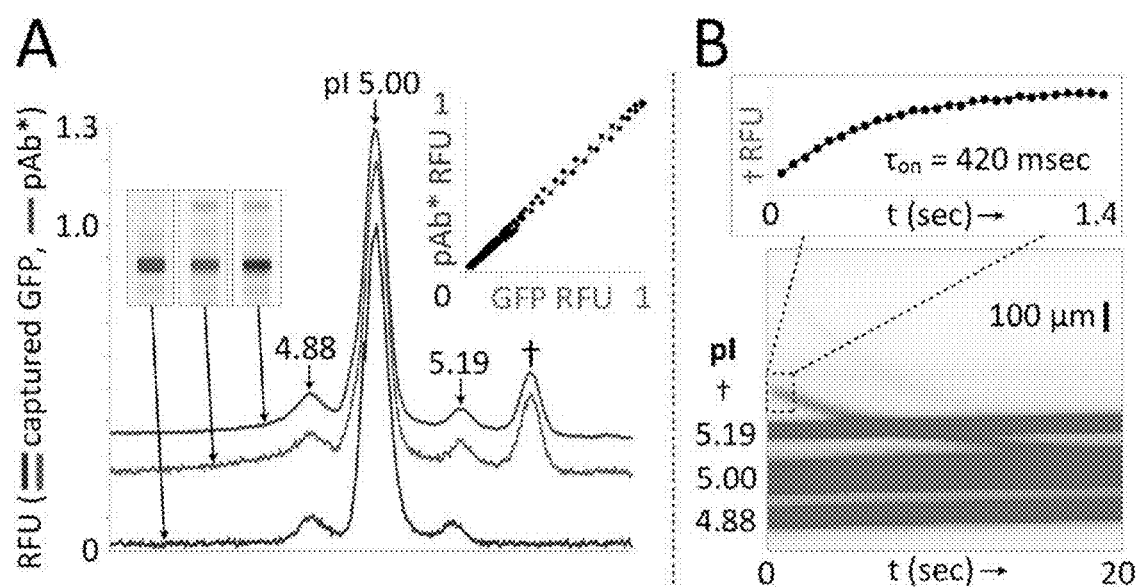
FIG. 2 shows assays of wtGFP indicating a photoswitchable isoform, according to embodiments of the present disclosure.
Figure 8:
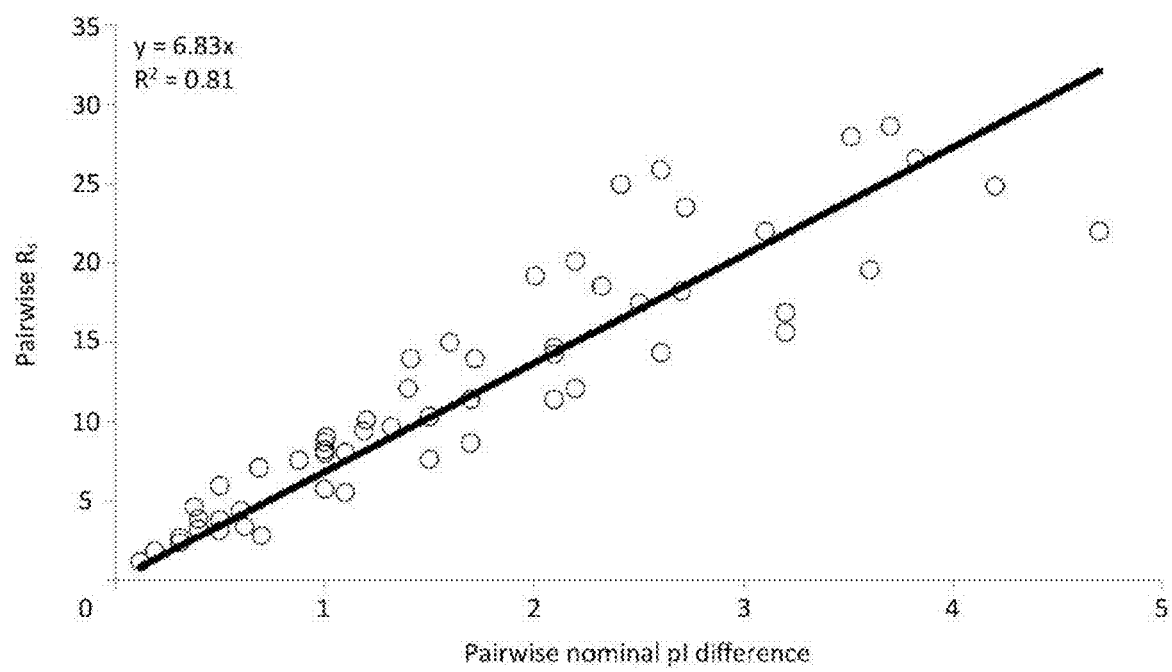
FIG. 8 shows a graph of separation resolution of analyte pairs under focusing conditions for the 8 pI markers and 3 GFP isoforms presented in FIG. 1D (55 total comparisons), according to embodiments of the present disclosure. A threshold of $R_s$=1 yielded a minimum separable pI difference of 0.15 via linear regression.

In the third assay stage, the re-established homogeneous buffer conditions permitted electrophoretic introduction of immunoaffinity probes (fluorescently labeled detection antibodies, pAb*=polyclonal antibody, mAb*=monoclonal antibody) into the protein-decorated gel (FIG. 1F). Electromigration of the probes through the nanoporous gel matrix facilitated efficient mass transfer of probe to captured target analytes. A final 20 min electrophoretic washout of free probe resulted in the target protein isoform pattern (FIG. 2A). Additional secondary antibody probing can be employed to improve assay sensitivity. Specific detection of wtGFP isoforms yielded a pAb* red fluorescence readout that replicated the native green fluorescence readout of the captured wtGFP against a ~20-fold excess of off-target ladder proteins. Analysis of wtGFP indicated a minimum resolvable pI difference of 0.15 pH units and a peak capacity of 110±22 (n=3 isoforms) (FIG. 8).

2. Isoelectric Photoswitching of wtGFP

Directly comparing the focused, captured and probed isoform patterns of wtGFP enabled identification of an isoform with reversibly photoswitchable fluorescence and pI. When wtGFP was briefly exposed to blue light (460-500 nm, 120 sec, in the focused state), the wtGFP isoform profile exhibited three canonical isoforms with pI's of 4.88, 5.00 and 5.19 (see FIG. 2A). When wtGFP was not exposed to blue light, a fourth isoform (pI~5.33) complemented the three expected wtGFP isoforms. The pI 5.33 peak accounted for ~16% of the GFP mass.

A dynamic photoswitching process was observable in real time using an IEF separation medium. Exposure of focused "dark-state" wtGFP to blue light switched on the fluorescence of the pI 5.33 peak. IEF monitoring allowed estimation of the "on" time constant at 420 msec (FIG. 2B). Further, dynamic "retreat" of the pI 5.33 wtGFP isoform towards the dominant peak (pI 5.00) was observed on the 5-10 sec timescale (FIG. 2B). This light-activated migration process was partially reversible under subsequent dark-light cycles. Without being limited to any particular theory, the pI switching behavior may be due to chromophore photoconversion and charge transfer phenomena. For example, the photoswitching peak may be the protonated (neutral) chromophore population, with blue light excitation leading to chromophore deprotonation and proton transfer to the solvent along an internal "proton wire". The reversible decrease in pI of this isoform indicates solvent accessibility of the labile wtGFP chromophore proton.

3. Capture Kinetics Inform Photoimmobilization Conditions

Experiments were performed to identify conditions for optimal mapping of the IEF separation to the separation medium during photoimmobilization. IEF exhibited cathodic drift due to the slight negative charge of polyacrylamide gels and the associated EOF. The separation medium cathodic drift velocity $u_{drift}$ was 1.0 μm s$^{-1}$<$u_{drift}$<3.3 μm s$^{-1}$ ($E_{IEF}$=300 V cm$^{-1}$ at IEF completion). Thus, a 10 s UV exposure ($\Delta t_{UV}$) during photoimmobilization yielded a drift distance ($L_{drift}$=$u_{drift}$·$\Delta t_{UV}$) of 10-33 μm for a focused protein band. The average peak width of focused GFP isoforms ($w_{ave}$=4$\sigma_{ave}$) was 100 μm, making $L_{drift}$ comparable to $w_{ave}$. As such, the UV exposure may be performed under zero-field conditions (E=0 V cm$^{-1}$) to minimize captured analyte dispersion arising from cathodic drift.

Figure 3:
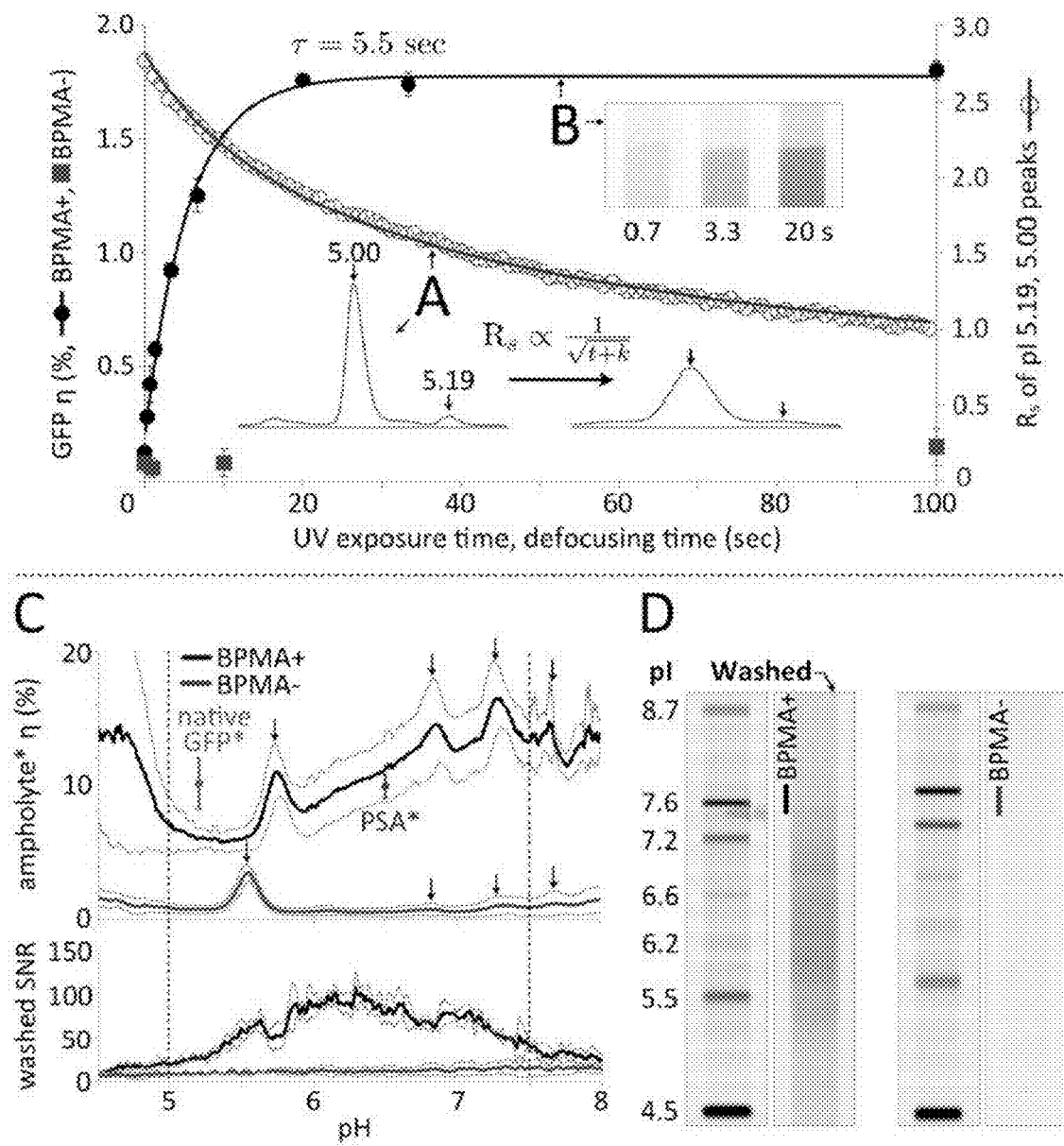
FIG. 3 shows graphs indicating rapid photoimmobilization kinetics with high capture efficiency and weak pH dependence, according to embodiments of the present disclosure.

In certain embodiments, the focusing force of IEF goes to zero under zero-field conditions with the initially focused protein bands broadening due to molecular diffusion. In some instances, this leads to a tradeoff between the extent of diffusional band broadening during capture and the duration of the photoimmobilization reaction. The timescale of diffusional band broadening was characterized after IEF focusing of wtGFP. Focused GFP was allowed to "defocus" under zero-field conditions with real-time single-point imaging (FIG. 3A). The separation resolution, $R_s$, of the pI 5.00 and 5.19 wtGFP isoform peak pair decreased from 2.8 to 1.0 over the course of 100 s $$(R_s = \frac{x_1 - x_2}{4\sigma_{ave}},$$

where $x_1$-$x_2$ is the distance between peaks). The defocusing behavior was in close agreement with the behavior expected under Fickian diffusion of Gaussian peaks.

To characterize the photoimmobilization reaction (FIG. 3B), an analyte "capture efficiency" was observed. The capture efficiency, η, was defined as the ratio of fluorescence measured after gradient washout ($AFU_w$) to the fluorescence during focusing ($AFU_f$), corrected by a factor ε to account for the anticipated influence of pH on the species fluorescence signal. In some instances, the washout buffer (pH$_w$=9.9) and the local pH of the buffer in the focused state (pH$_f$~pI) are different. Thus, the capture efficiency was:

$$\eta = \frac{AFU_{w,pHw}}{AFU_{f,pHf}} \times \varepsilon_{pHw,pHf} \times 100\% \quad [1]$$

Where the pH dependence of the fluorescence signal was measured via free-solution microplate experiments to be: $\varepsilon_{pHw=9.9,pHf\sim5}$≈0.75 for wtGFP and $\varepsilon_{pHw=9.9,pHf=4.3-9.4}$≈1 for all CE540-labeled species in this example. The capture efficiency of wtGFP was evaluated under non-focusing conditions using GFP uniformly distributed throughout the separation medium. The wtGFP was then immobilized by spot UV exposure via a 10× microscope objective (FIG. 3B). GFP photoimmobilization was adequately described by a first order process relating η to the UV exposure time through an integrated rate law of the form $$\eta = a\left(b - e^{-\frac{t}{\tau}}\right).$$

By least-squares fitting, the time constant τ for the immobilization reaction was determined to be 5.5 sec (a=1.59, b=1.12). The maximum wtGFP capture efficiency was 1.8%. This capture efficiency was a more than 100-fold improvement over the ~0.01% reported for surface photoimmobilization. The significant increase in capture efficiency may be due to the greater reactive surface area of the separation medium according to embodiments of the present disclosure.

Balancing the photoimmobilization kinetics with resolution loss by defocusing suggested an optimal exposure time of 10 sec. A $\Delta t_{UV}$ of 10 sec conferred 84% of the achievable capture efficiency for a decrease in separation resolution of 22% from that in the focused-state.

4. Separation Medium Capture Efficiency has a Weak pH Dependence

Experiments were performed to verify pH-consistent photoimmobilization performance by determining η over a wide pH range under IEF conditions. To achieve this, the immobilization behavior of fluorescently labeled ampholytes with pIs in the 5-7.5 range was characterized (FIGS. 3C and 3D). Ampholytes are mixtures of polyprotic amino carboxylic acids that buffer at their pIs. The pH 5-7.5 range encompassed most protein pIs (~65% of a diverse set of 500 protein isoforms studied using macro-IEF). The red fluorescent pyrilium salt CE540 (Chromeo P540, Pye 6) was conjugated to the amine termini of the ampholytes. A charge-compensating reaction mechanism allowed CE540 labeling to avoid introduction of charge heterogeneity. The resulting red fluorescent ampholyte species (ampholyte*) were a structural analog to polypeptides, and allowed η to be measured across a broad pH range.

FIG. 3C shows a ~2-fold monotonic rise in the ampholyte* η between pH 5 and 7.5. The η for the negative control gel (BPMA–) over this range is indistinguishable from background. Similarly, while the BPMA+ signal-to-noise ratio (SNR) spanned ~20-100 over pH 5-7.5, the BPMA– gel yielded substantially lower SNR. For further comparison, FIG. 3D shows fluorescence micrographs of ampholyte* intensity along the separation channel for both BPMA+ and BPMA– gels after electrophoretic washout. Without being limited to any particular theory, the increase in η with pH may be due to a change in the chemical properties of the ampholyte species, which were also graded along the pH axis. The pH response of η was acceptable given the absence of a strong bias towards any particular pH zone and the fact that protein isoforms were generally clustered over a relatively tight pI range. Thus, in certain embodiments, a single capture efficiency for all isoforms of a given target was likely to be valid in most applications. Also plotted on FIG. 3C is η for both native GFP* and PSA* (10.1±1.91%, n=8; and 9.92±0.86%, n=3 respectively). Both species exhibited η on par with ampholyte* capture.

Figure 9:
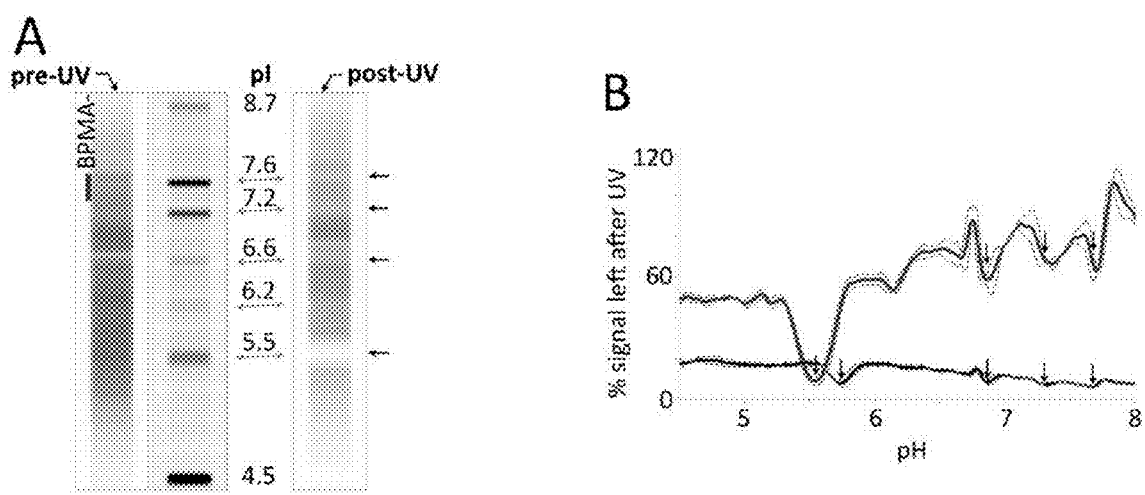
FIG. 9 shows gel images and a graph indicating that colocalized ampholyte* species and pI markers yielded enhanced photobleaching, according to embodiments of the present disclosure.

Arrows in FIG. 3C indicate regions in which co-localization of pI markers and ampholyte* produced higher ampholyte* photobleaching during UV exposure in both BPMA+ and BPMA– gels (see FIG. 9). This exaggerated local bleaching manifested as artifactual peaks in the ampholyte* η data.

5. Influence of Target Protein Hydrophobicity on Separation Medium Capture Efficiency In certain embodiments, CE540 labeling effected the conformational heterogeneity and capture efficiency of wtGFP. In some instances, the ampholyte*, PSA* and native GFP* η values (at ~10% each) were all significantly higher than the η of 1.30±0.17% (n=44) measured for unlabeled GFP in the focused state across several chips and experiment days. Without being limited to any particular theory, the hydrophobic structure of CE540 may be the source of this higher η by increasing weak "pre-covalent" interactions of labeled species with the gel matrix.

6. Assays for PSA Isoform Quantitation

Figure 4:
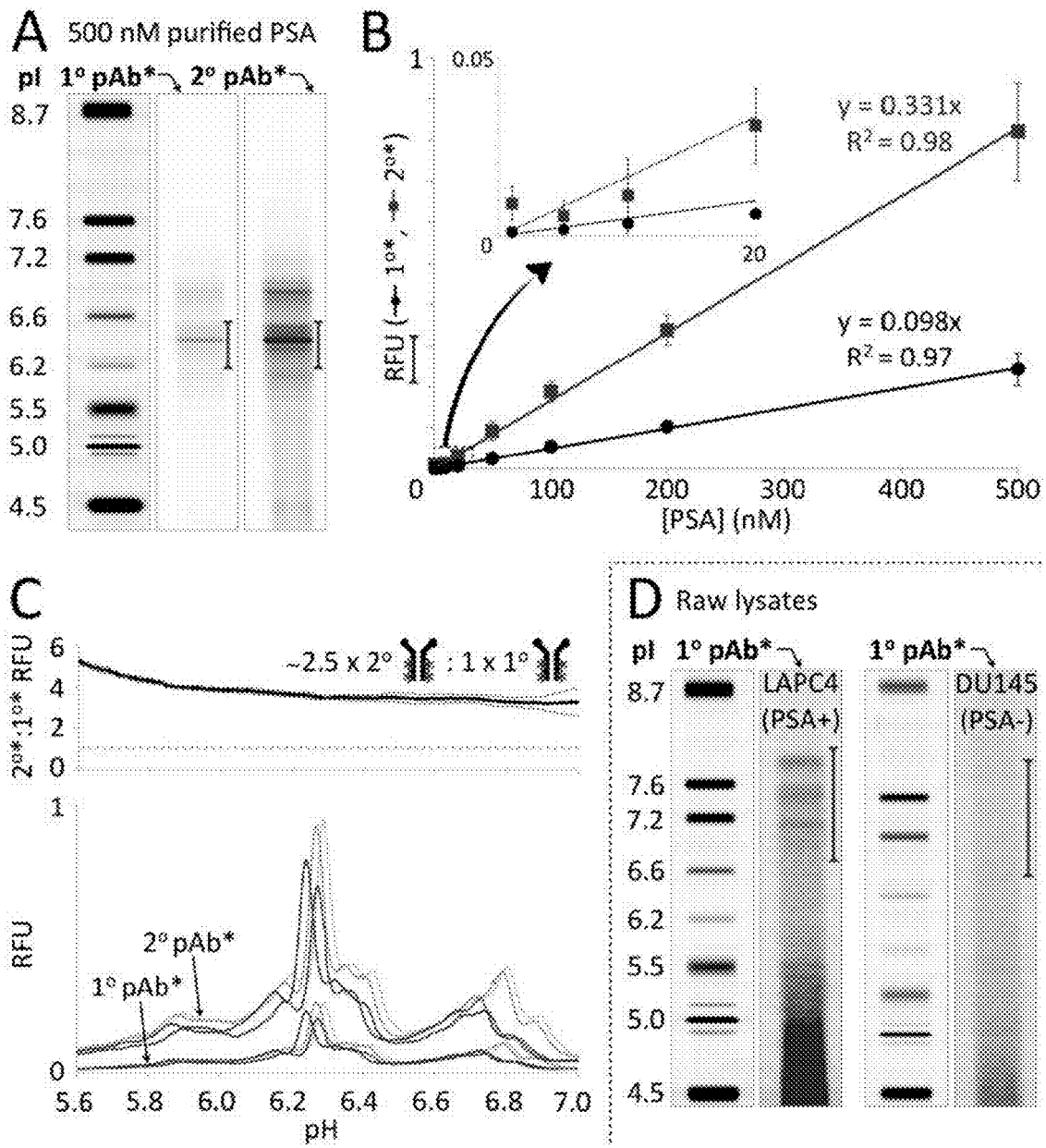
FIG. 4 shows a linear separation medium calibration curve for purified PSA with inference of probe stoichiometry and the measurement of PSA in cell lysate, according to embodiments of the present disclosure.

Purified underivatized PSA was probed after IEF and photoimmobilization using sequential introduction of specific primary and secondary detection antibodies (FIG. 4A). Two major isoforms with pIs of 6.27±0.02 and 6.77±0.04 (n=4) were apparent, accompanied by several minor peaks below baseline resolution. Macroscale slab gel IEF of PSA gave a similar isoform pattern. The PSA calibration curve is shown in FIG. 4B. In FIG. 4B, the relationship between the nominal PSA concentration and fluorescence readout over the dominant isoform (pH 6.0-6.5) was linear in the range of ~10-500 nM. Quantitative capacity was maintained to ~5 nM PSA (165 ng ml$^{-1}$) or ~1.1 pg of PSA.

Based on these antibody probing analyses, the stoichiometry of secondary:primary Ab* binding can be inferred from the ratio of the respective fluorescence traces (FIG. 4C). In these experiments, the degrees of labeling of each antibody probe were similar, and the labeling dye was the same (red Alexa Fluor 568). The binding stoichiometry was determined to be ~2.5 across the relevant pH range, exhibiting somewhat higher values at the acidic end of the isoform pattern due to a non-specific contribution of the secondary Ab* to the assay readout.

Experiments were performed to quantify endogenous PSA isoforms present in minimally processed cell lysate from LAPC4 human prostate cancer cells (FIG. 4D). The LAPC4 cell lysate expressed PSA at a concentration of 19.5±2.7 nM, as quantified by ELISA (n=8). As a negative control, a DU145 (PSA–) lysate was also assayed. The probed LAPC4 lysate presented a distinctive 3-peak pattern in the pI 6.75-8 range, with non-specific signal apparent near the anodic well (the electrophoretic introduction point for both sample and pAb*). This pattern was similar to those presented in slab gel assays of PSA purified from LNCaP cell culture medium. The total LAPC4 PSA concentration for this assay was determined to be 27.8±4.7 nM (n=4) from the purified PSA calibration curve of FIG. 4B.

7. Assays in Isoform "Recognition Mapping" Mode

Figure 5:
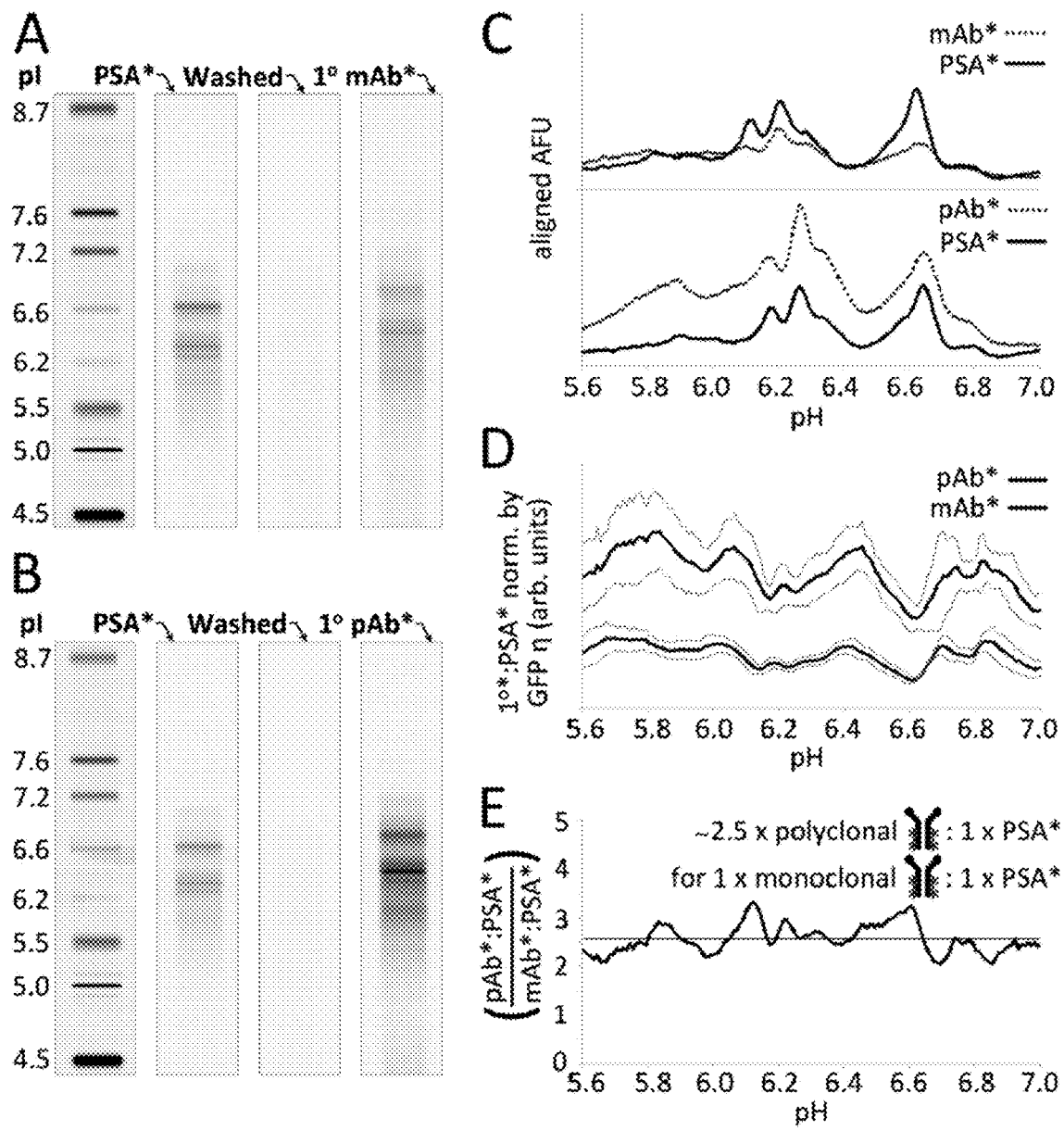
FIG. 5 shows microfluidic assays in recognition mapping mode for isoform-resolution probe screening, according to embodiments of the present disclosure.

To validate the capability of assays of the present disclosure to measure immunoreagent isoform specificity, the isoform distribution of IEF-focused CE540-labeled PSA* were compared to its probe fluorescence readout after photoimmobilization and probing with mAb* and pAb* (FIG. 5). Alignment between each pair of fluorescence intensity profiles (PSA*, Ab*) was accomplished by applying a translation inferred from their cross-correlation. The translational shift corrected for the slight drift (~190 μm) between imaging of focused PSA* and the photoimmobilization step. The focused PSA* isoform pattern agreed well with that of the probed unlabeled PSA, suggesting minimal impact of CE540 on the pIs of the native PSA isoforms (compare FIGS. 5A and 5B to FIG. 4A). Ratiometric comparison of the probed and focused PSA* signals suggested spatially uniform probe layering onto immobilized PSA* across the pH region of interest, for both polyclonal and monoclonal detection antibodies (FIGS. 5C and 5D). Some variation across the pH range was induced by diffusional band broadening during photoimmobilization, which had the expected "peak blunting" effect on the probing data. Comparison of the monoclonal and polyclonal probing ratios showed a 2.5:1 pAb*:PSA* stoichiometry (assuming a 1:1 stoichiometry inherent in the monoclonal readout with [Ab*]»$K_D$, equilibrium in binding (30), and negligible PSA "epitope disfigurement" upon immobilization, FIG. 5E).

Discussion

1. Rapid Capture Kinetics with Efficiency Independent of Analyte Concentration.

The reaction between the separation medium and the protein target analyte occurred against a background of competing reactions. In some embodiments, a portion of the photoactive BPMA sites may form conjugates with off-target species (e.g., ampholytes, gel matrix, sorbitol, NDSB 256 and CHAPS), which constitute a ~$10^6$-fold excess over protein targets.

Consider homogeneous parallel irreversible reactions between one common reactant (BPMA, species A) and a set of competing species (species $B_i$), one of which is the target protein of interest. Assuming small capture efficiencies, free species concentrations do not change appreciably from their initial values, where lower case denotes concentration of a species), meaning $b_i \sim b_{i,o}$. From the rate of consumption of BPMA, the integrated rate expression for formation of a given adduct $P_i$ can be determined:

$$p_i = \frac{b_{i,o} k_i a_o}{(k_T')(1 - e^{-k_T' t})} \text{units } Ms^{-1} \quad [2]$$

Where $$k_T' = \sum_{i=1}^{n} k_i' = \sum_{i=1}^{n} b_{i,o} k_i$$

is a sum of the pseudo-first-order rate constants $k'_i$ the competing reactions (N.B. $a_o$ is the concentration of BPMA). Equation 2 shows the property that despite each individual reaction having different $k'_i$, the rates of generation of each product are identical, characterized by a time constant $$\tau = \frac{1}{k_T'}$$

that is made small by the strong competition for BPMA sites. The observed timescale of target capture was expected to be approximately independent of the target protein concentration as the contribution of $k'_{target}$ to $k'_T$ is small given the excess of off-target reactants ($k'_T \gg b_{target,o} k_{target}$, where subscript target denotes the reaction between the protein target of interest and BPMA). Also, for long reaction times (from Equation 2):

$$\eta_{target} = \frac{p_{target}}{b_{target,o}} \times 100 = \frac{k_{target} a_o}{k_T'} \times 100 \quad [3]$$

-continued $$\eta_{target} = \frac{p_{target}}{b_{target,o}} \times 100 = \frac{k_{target} a_o}{k_T'} \times 100$$

$$\eta_{target} = \frac{p_{target}}{b_{target,o}} \times 100 = \frac{k_{target} a_o}{k_T'} \times 100$$

Again, for $k'_T$~ independent of the target concentration $b_{target,o}$, $\eta_{target}$ is independent of (i.e., a constant across the calibration curve). Taken together with the fact that subsequent probe binding to captured target is driven to saturation at equilibrium for reaction-limited conditions and sufficiently high probe concentration above $K_D$, a linear calibration curve was expected in the subject microfluidic devices, as observed for PSA in FIG. 4B.

2. Analyte Capture Efficiency is Boosted by 3D Reaction Site Matrix.

The capture efficiency of the separation medium was compared to capture on an internal surface of an "open" capillary tube with 100 μm ID. The benefit of high immobilization surface area $A_s$ is revealed by noting that the concentration of BPMA in a control volume V is $$a_o = \frac{a_{o,s} A_s}{V}$$

assuming a uniform site density $a_{o,s}$ (mol BPMA m$^{-2}$). Approximating the gel as a bundle of packed cylinders in simple cubic arrangement with radius equal to that of the mean pore radius of ~120 nm for a 4% T, 2.6% C polyacrylamide gel yielded (via Equation 3):

$$\frac{\eta_{gel}}{\eta_{cap}} \sim \frac{A_{s,gel}}{A_{s,cap}} \sim 300 \quad [4]$$

$$\frac{\eta_{gel}}{\eta_{cap}} \sim \frac{A_{s,gel}}{A_{s,cap}} \sim 300$$

Suggesting a ~2-3 order-of-magnitude increase in capture efficiency within the gel matrix as compared to the capillary surface. This estimate was similar to the experimentally observed ~180-fold increase in η over that measured for capillary surface photoimmobilization.

3. Microscale Mass Transport Accelerates Immunoprobing to Reaction "Speed Limit".

Probing of target protein $P_{target}$ with antibody C electromigrating through the gel pores to form a stationary product immunocomplex can be considered as a homogeneous reaction occurring between two reactant bands mixed electrophoretically. The arrangement of target on the separation medium circumvents the diffusion-limited mixing regime that often arises at the microscale. Here, the appropriate mass transfer timescale is that of band/front crossing, $$t_{cross} = \frac{w}{u_{rel}} \sim 2$$

sec for probing of a captured target band, where w is its width and $u_{rel}$ the velocity of the probe front.

In the case of target probing on the wall of a capillary, mass transfer and surface reaction rates can become intimately coupled via a surface boundary layer in which the probe is locally depleted. The dimensionless factor that evaluates the interplay between surface reaction (rate coefficient k') and boundary layer mass transfer (rate coefficient β) is the Damkohler number:

$$Da = \frac{k'}{\beta} \quad [5]$$

Thus for Da ≫ 1, reaction speed is greater than mass transfer and the system becomes mass transfer limited, whereas for Da ≪ 1, mass transfer if faster than the reaction and the system is reaction limited. Estimating Da for the open capillary capture scenario indicates that Da ≪ 1 (for the low achievable values of $P_{target}$), which indicates reduced boundary layer resistances in confined micro-nanoscale reaction volumes.

The small values of Da and $t_{cross}$ suggest that the minimum reaction timescale $$\tau_R \sim \frac{1}{k_{on}c_o + k_{off}}$$

controls the probing equilibration time, where $c_o$ is the bulk probe concentration in the separation medium or capillary lumen and $k_{on}$ and $k_{off}$ are the forward and reverse binding rate constants, respectively. FIG. 1F shows experimental evidence for this in the separation medium, showing $\tau_R \gg t_{cross}$ in the separation medium. In certain embodiments, $k_{on}\sim 10^6$ M$^{-1}$ s$^{-1}$ and $k_{off}\sim 10^{-3}$ s$^{-1}$ ($K_D\sim 1$ nM, depending on the antibody). In certain cases, the probe antibody concentration $c_o$ was chosen to be in large excess compared to $K_D$ at $c_o\sim 100$ nM, giving $$\tau_R \sim \frac{1}{k_{on}c_o} = 10$$

sec (c.f. $t_{cross}\sim 2$ sec). Further, at equilibrium, captured target species can be shown to be saturated with probe when $c_o \gg K_D$ (again contributing to assay linearity in FIG. 4B). The fact that the observed value of $\tau_R$ in the separation medium is on the order of 5 min (FIG. 1F) rather than 10 sec may indicate that the kinetic "on" and "off" rates are modified in the gel environment. In some instances, the rapid mass transfer regime operating in a nanoporous separation medium accelerates the immunoprobing process to the reaction "speed limit".

Materials and Methods

1. Microfluidic Assay Instrumentation.

Optical white soda lime glass microdevices were designed in-house and fabricated by Caliper Life Sciences (Hopkinton, Mass.) using standard wet etching processes. Channels were 10 μm in depth, 70 μm wide, and had a working length of ~10.4 mm. Channels were spaced 80 μm apart (edge-to-edge) in doublets between each 2 mmø access well pair to ensure optical isolation during simultaneous imaging of neighboring channels. Pairs of doublets were arranged in "imaging streets" ~2 mm apart, yielding 4 separation media per well pair and 16 separation media per chip.

A programmable high-voltage power supply (1275 Lab-Chip Controller, Caliper) was used for electrophoretic chip control via platinum electrodes directly inserted into 10 μL press-fit pipet tip sample reservoirs.

Glass channels were functionalized with acrylate-terminated self-assembled monolayers. The separation medium was fabricated via introduction of a gel precursor solution by capillary action. The precursor contained 4% w/v total acrylamide (4% T) with 2.6% of the total as the crosslinker bisacrylamide (2.6% C), 2% Pharmalyte 3-10 titrated to pH 9.9 with NaOH (17-0456-01, GE Healthcare, Little Chalfont, UK), 3% CHAPS detergent (C9426, Sigma, St. Louis, Mo.), 10% sorbitol, 200 mM NDSB-256 (17236, Sigma), 4.5 mM BPMA (see Reagents and Samples). The initiators APS (0.08%, A3678, Sigma) and TEMED (0.08% v/v, T9281, Sigma) were added just before introduction of degassed precursor to channels. Just after visible gelation of the excess precursor, wells were flushed and replaced with gel buffer (details of buffers used and microfluidic chip operation protocol are provided below).

2. Reagents and Samples.

N-[3-[(4-benzoylphenyl)formamido]propyl]methacrylamide (BPMA) monomer was synthesized and verified by $^1$H NMR and mass spectrometry. The monomer was added to BPMA+ gel precursor solutions at 4.5 mM (~1 mol % with respect to acrylamide) from a 100 mM stock in DMSO. BPMA- precursors contained an equivalent volume of DMSO lacking BPMA. Purified proteins, antibodies and fluorescent labeling protocols are described in more detail below.

LAPC4 and DU145 lysates were purified in P-6 Bio-Spin columns (Bio-Rad, Hercules, Calif.) and added to samples at 2× dilution. Equal volumes of a set of fluorescent IEF pI markers (pI 4.0, 4.5, 5.5, 6.2, 6.6, 7.2, 7.6, and 8.7) were mixed in a cocktail and added to samples at 20× dilution (89827 and related products, Sigma). Samples in loading buffer were titrated to pH 9.9 with 1M NaOH just prior to electrophoretic loading.

3. Data Acquisition and Analysis.

Whole channel imaging at 10× was conducted via stitching of adjacent, overlapping CCD images in ImageJ (NIH, Bethesda, Md.) to produce full gel channel images and electropherograms. Imaging scans along both streets required ~40 s to complete.

4. Synthesis of BPMA.

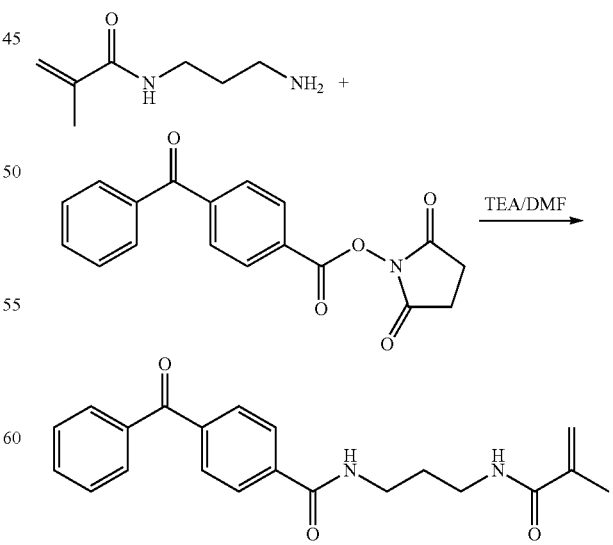

N-[3-[(4-benzoylphenyl)formamido]propyl]methacrylamide (BPMA, $C_{21}H_{22}O_3N_2$, 350.4 g mol$^{-1}$) monomer was synthesized via reaction of the succinimidyl ester of 4-benzoylbenzoic acid (BP-NHS, 323.3 g mol$^{-1}$; B1577, Invitrogen) with N-(3-aminopropyl)methacrylamide hydrochloride (APMA, 178.7 g mol$^{-1}$; 21200, Polysciences, Warrington, Pa.) in the presence of catalytic triethylamine (TEA) in dimethylformamide (DMF). A mixture of the reactants and TEA at 50 mM each in DMF was incubated overnight (18 hrs) at room temperature, centrifuged at 18,000 g for 5 minutes and the pellet discarded. The supernatant was incubated on a tube inverter for 24 hrs with 30 mg isothiocyanate-functionalized (primary amine-reactive) polystyrene beads (538604, Sigma) for every 100 µmol of APMA initially added to the reaction. The mixture was then spun at 18,000 g for 5 minutes and the supernatant passed through a 0.2 µm syringe filter. A 10-fold excess of acetone was added to the filtrate and the mixture dried in vacuo. The BPMA product (white powder) was verified by $^1$H NMR (400 MHz, d$_6$-DMSO, δ8.79 (t, 1H), 8.04 (t, 1H), 8.02 (d, 2H), 7.80 (d, 2H), 7.75 (d, 2H), 7.70 (t, 1H), 7.58 (t, 2H), 5.67 (s, 1H), 5.32 (s, 1H), 3.31 (q, 2H), 3.18 (q, 2H), 1.86 (s, 3H), 1.71 (quin, 2H)) and mass spectrometry (ESI, m/z 351.2, $C_{21}H_{22}O_3N_2+H^+$). 100 mM stocks of BPMA in DMSO were stored at −20° C. until use, and were stable for at least 12 months.

5. Purified Proteins and Antibodies.

Pharmalyte 3-10 was minimally labeled by mixing a 1% solution in 200 mM sodium bicarbonate pH 8.3 with an equal volume of 2.27 mM CE540 in DMSO (346.5 g mol$^{-1}$, 15102, Active Motif, Carlsbad, Calif.; dye:ampholyte ratio of ~0.1 given average ampholyte MW of ~500 g mol$^{-1}$ (1)) and incubating at 50° C. for 1 hr. wtGFP (recombinant from *E. coli, A. victoria* wild-type; 632373, Clontech, Mountain View, Calif.), purified PSA (from human seminal fluid; ab78528, Abcam, Boston, Mass.) and the Serva IEF 3-10 protein marker mix (39212-01, Invitrogen, Carlsbad, Calif.) were labeled with CE540 according to manufacturer instructions. 1° antibodies to PSA (goat pAb; AF1344, R&D Systems, Minneapolis, Minn.; mouse mAb; M167, CalBioreagents, San Mateo, Calif.) were labeled with Alexa Fluor 568 dye according to manufacturer instructions (Invitrogen). Fluorophore:protein molar labeling ratios, MR, were 4.0 and 4.7 for the pAb* and mAb* respectively. The rabbit anti-goat IgG 2° was labeled similarly (MR=3.2; 305-005-045, Jackson ImmunoResearch, West Grove, Pa.). The 1° goat pAb to GFP was prelabeled with Texas Red by the manufacturer (MR=2.9; ab6660, Abcam). Fluorescently labeled proteins were purified using P-6 (PSA, GFP) or P-30 (antibodies) Bio-Spin chromatography columns (Bio-Rad, Hercules, Calif.) to remove free dye prior to loading on the separation medium.

6. Buffers.

Sample loading buffer was of the same composition as gel precursor, but lacked monomers and initiators. Catholyte was 20 mM lysine, 20 mM arginine pH 10.1. Anolyte was 70 mM phosphoric acid. pH gradient washout buffer/probing buffer was 15 mM glycine pH 9.9, 3% CHAPS, 200 mM nondetergent sulfobetaine (NDSB) 256, 10% sorbitol.

A list of buffers used for microfluidic chip operation is provided below in Table 1.

7. Microscopy and UV Exposure.

Chip imaging was conducted using an Olympus IX50 inverted fluorescence microscope equipped with CCD camera (CoolSNAP HQ$^2$, Photometrics, Tucson, Ariz.) motorized stage (Applied Scientific Instrumentation, Eugene, Oreg.) and shutter systems (Sutter Instrument, Novato, Calif.) controlled by MetaMorph software (Molecular Devices, Sunnyvale, Calif.). Flood UV duty was provided by a Hamamatsu Lightningcure LC5 (Bridgewater, N.J.) directed through a Lumatec series 380 liquid light guide (Deisenhofen, Germany) with inline UV filter (~300-380 nm bandpass; XF1001, Omega Optical, Brattleboro, Vt.) suspended ~10 mm above the chip plane with UV power at the chip plane of ~160 mW cm$^{-2}$ (UV513AB meter, General Tools, New York, N.Y.). Kinetic study of separation medium immobilization was conducted via spot UV exposure through a 10× objective (Olympus UPlanFl, NA 0.3) and XF1001 exciter, with UV power at the chip plane of ~40 mW cm$^{-2}$.

Green and red fluorescence channels were imaged at 10× using Omega Optical filter cubes optimized for GFP (XF100-3) and DsRed2 (XF111-2). IEF pI markers were imaged prior to UV immobilization using a custom UV-longpass filter cube (excitation 300-380 nm, emission>410 nm; XF1001, XF3097, Omega Optical) and channel positions were manually scored (gradient drift between focused-state marker and analyte imaging steps was assumed to be negligible). Exposure times were 50 ms for pre-washout scans and 400 ms post-washout, all with 4×4 pixel binning (CCD signals were linear in exposure time). Real-time single-point imaging of GFP isoform dynamics and GFP was conducted in burst acquisition mode to eliminate camera and image transfer lag.

Transformation of fluorescence data via linear fits to pI markers and associated data processing was performed using MATLAB scripts written in-house (MathWorks, Natick, Mass.). Least-squares fitting of kinetic data was performed using gnuplot software.

8. Microfluidic Chip Operation Protocol.

After gelation, access wells were filled with gel buffer (see Table 1). 30 µl samples were made in loading buffer and titrated to pH 9.9 with 1.5 µl 1M NaOH just prior to introduction at loading wells (~5 µl per well). Sample injection was performed at 200 V cm$^{-1}$ for 3 minutes. Catholyte and anolyte buffers were used to wash opposite wells twice; wells were subsequently filled. Focusing was conducted simultaneously for the four devices in each chip (i.e., all well pairs), at 50 V cm$^{-1}$ for 4 min; 100 V cm$^{-1}$, 5 min; 200 V cm$^{-1}$, 5 min. 3 min, 300 V cm$^{-1}$ focusing, imaging and flood UV exposure steps were conducted individually for each device in series. Imaging of pI markers via 50 ms exposures was preceded by any green and/or red channel scans required. Following marker imaging, the chip was moved into position beneath the lightguide tip under motorized stage control. Under stopped electric field, 2×5 s flood UV exposures were applied in neighboring spots (~5 mm apart along the channel axis) to ensure uniform UV dosage. The final focusing, imaging and flood exposure steps were repeated for the other devices on the same chip. Refocusing and imaging was conducted as necessary prior to simultaneous washout of all devices. Access wells were washed and filled with glycine washout/probe buffer. Mobilization and washout of pH gradients to the anodic wells was achieved via a 20 min electrophoretic step. Labeled antibody probes were diluted in washout/probe buffer, loaded, and removed from the separation medium in 20 min electrophoretic steps; wells were washed with buffer as required to prevent undesired cross-reaction of 1° and 2° probes in access wells. Probe loading and washout were conducted in opposite directions to minimize non-specific signal remaining after washout. Final green and/or red scans were performed as necessary with 400 ms image exposure time.

In the case of kinetic studies of separation medium immobilization, GFP was electrophoretically loaded at 200 V cm$^{-1}$ as a homogeneous stream in untitrated loading buffer (pH~6.5). UV exposure dosage applied via the microscope mercury lamp was tightly controlled via the mechanical excitation shutter. 20 min GFP washout was performed by replacing sample with fresh untitrated loading buffer before application of 200 V cm$^{-1}$ field in the opposite direction to loading for 20 min.

9. Cell Culture.

The human prostate cancer cell lines DU145 and LAPC4 were obtained from American Type Culture Collection (ATCC, Manassas, Va.) and Dr. Charles Sawyers (UCLA), respectively. DU145 cells were grown in DMEM (Invitrogen) and LAPC4 cells in IMDM (Invitrogen) supplemented with 10% fetal bovine serum (FBS) (HyClone, Logan, Utah) and 100 µg/ml of gentamycin (Fisher, Fairlawn, N.J.) in 100-mm dishes at 37° C. in 5% $CO_2$. Medium was changed twice a week and the cells were subcultured using TrypLE Express (Invitrogen).

10. Lysate Preparation.

One day after feeding, three to five 100-mm dishes of DU145 cells at 90% confluency or LAPC4 cells at 75% confluency were used to prepare cell lysates. Each dish was washed once with HEPES-buffered saline (HBS) and then incubated with 1 ml of TrypLE Express at 37° C. for 5 minutes. Dishes were washed with HBS to collect cells, which were then centrifuged to pellet the cells. After the HBS was removed, each cell pellet was resuspended in HNTG buffer (20 mM HEPES pH 7.5, 25 mM NaCl, 0.1% Triton X-100, 10% glycerol). Each of these samples was then supplemented with 1:100 Protease Inhibitor Cocktail (Calbiochem, La Jolla, Calif.) and 1 mM phenylmethylsulfonyl fluoride (Sigma). Samples were incubated on ice for 30 minutes, vortexing every 5 minutes. Next, samples were centrifuged at 16,000 g for 10 minutes at 4° C. The lysate supernatant was collected and the protein concentration was measured using a Bio-Rad protein assay (Bio-Rad, Hercules, Calif.). Aliquots of 20 µL from each lysate were frozen on dry ice and stored at −80° C.

11. Serum Preparation.

Pooled negative control serum was from US Biological (S1005-05). Advanced metastatic prostate cancer patient blood samples were collected between 1998 and 1999 with informed consent under an institutional review board-approved protocol in red-top vacutainer tubes (BD Biosciences) at Stanford University Medical Center Oncology Clinic. Tubes were inverted five times and blood allowed to clot. Tubes were then centrifuged at 1,000×g for 10 min. Serum was extracted and stored at −80° C. until assay.

12. Benchmark Assays.

Figure 10:
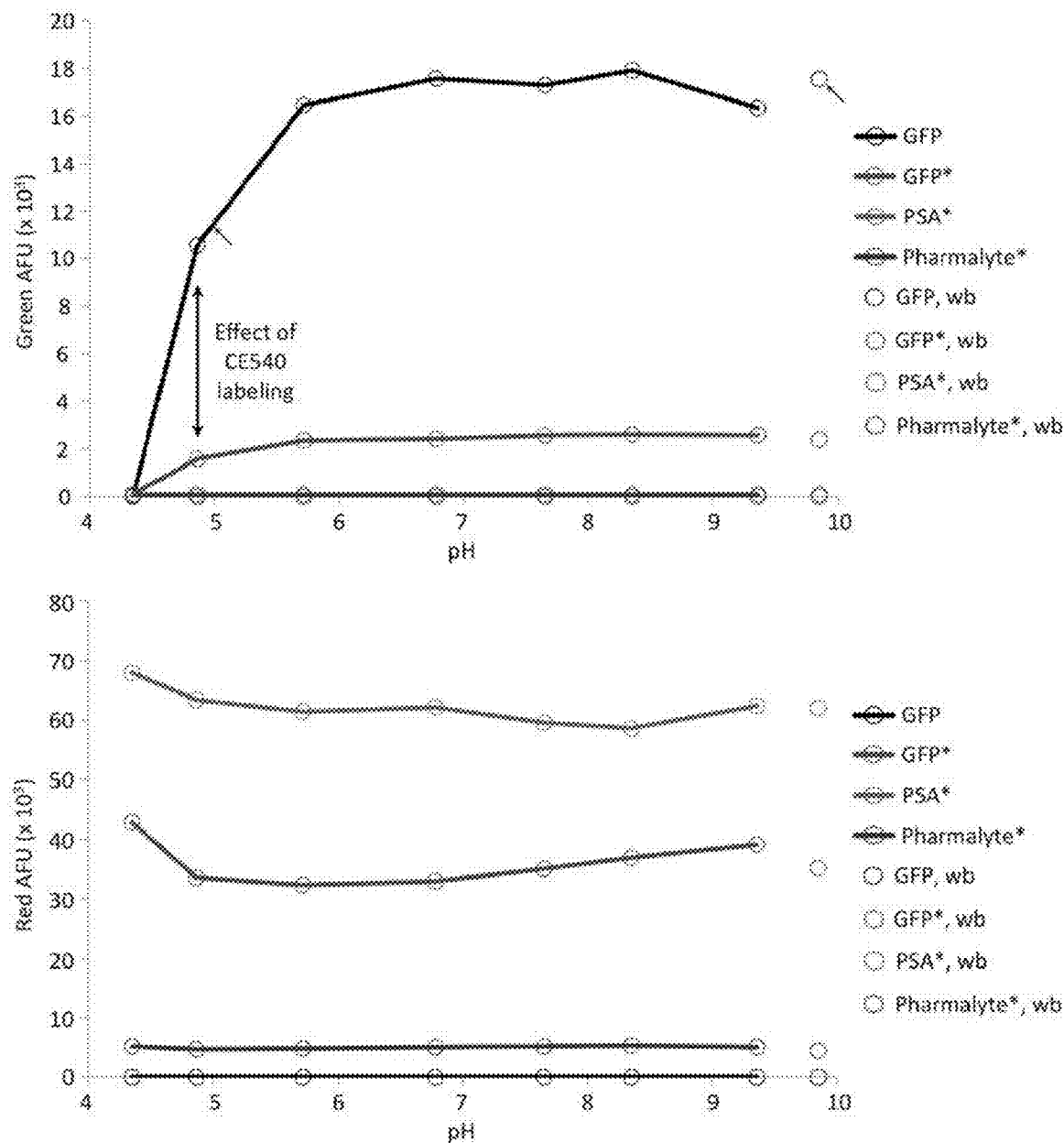
FIG. 10 shows graphs of microplate experiments that show the denaturing effect of GFP labeling and allow extraction of $\varepsilon_{pHw,pHf}$.

PSA ELISAs (DKK300, R&D Systems) were conducted on LAPC4 and DU145 lysates according to manufacturer instructions using a Tecan Infinite microplate reader (Tecan, San Jose, Calif.). ELISA calibration standards were run in duplicate; the standard curve was linear in the 1-60 ng ml$^{-1}$ range ($R^2$>0.99). Unknown lysate sample were diluted in the range of 20-500 fold and run in duplicate, inferred concentrations falling in the linear calibration range were pooled as assay readout. Novex 3-10 IEF gels were run in a Novex Mini-Cell against the Serva protein marker mix according to manufacturer instructions with 1 µg total protein per lane; gels were silver stained with a SilverXpress kit (Invitrogen). Custom slab gels were run on a Mini IEF Cell (Bio-Rad) and were of the same composition as the BPMA− separation medium. $\varepsilon_{pHw,pHf}$ were determined for labeled analytes via fluorescence measurements in loading buffers titrated to pH values in the range of interest and in washout buffer (FIG. 10).

Results and Discussion

1. Influence of Target Protein Hydrophobicity on Capture Efficiency.

Figure 11:
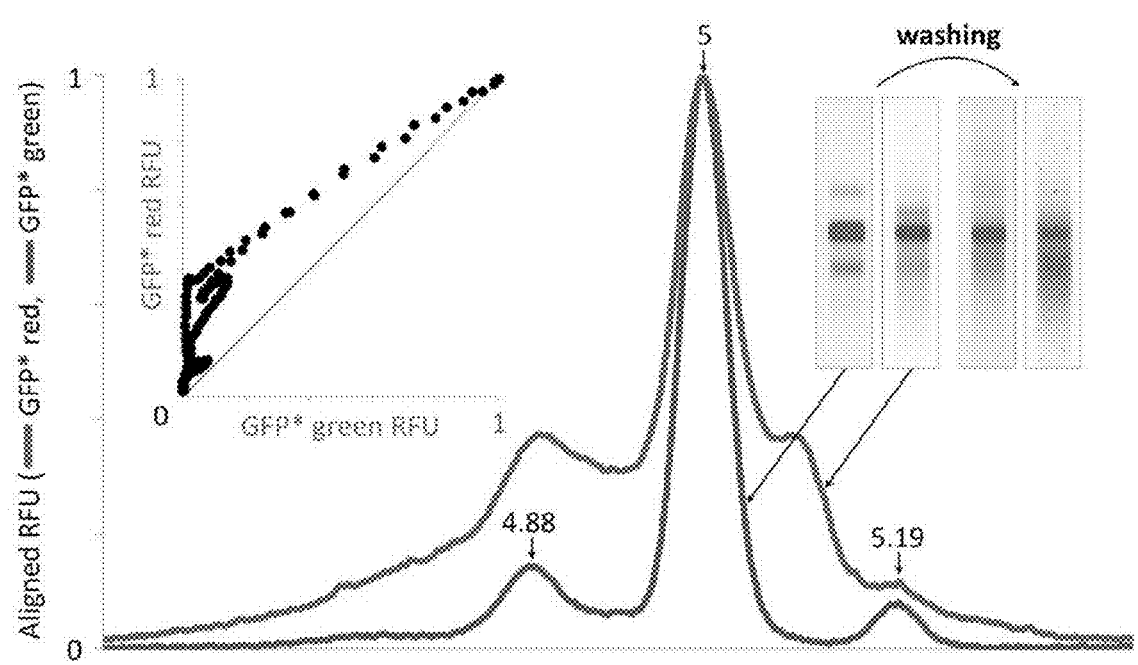
FIG. 11 shows graphs indicating CE540-labeled GFP exists as native (green+, red+) and denatured (green−, red+) sub-populations. The graph shows aligned relative fluorescence data from sequential imaging on green and red spectral channels for GFP* focused at 300 V cm$^{-1}$ in a single separation medium (nominal [GFP*]=617 nM). The red fluorescence readout was dominated by the denatured population, presenting as a diffuse set of bands with rough correspondence to those of the native GFP* population (green fluorescence readout). The canonical 3-band structure observed for the native GFP* population was similar to that of unlabeled GFP (see FIG. 2A).

Experiments were performed to assess the effect of fluorescence labeling of samples on the apparent capture efficiency η. The focusing and immobilization data for CE540-labeled wtGFP* showed that CE540 labeling generated native and denatured protein sub-populations (FIG. 11). During IEF, the native population was characterized by co-localized green (endogenous) and red (CE540) fluorescence (i.e., green+, red+). A dominant GFP* population was also observed that lacked any co-localized green signal (i.e., green−, red+). In this latter population of GFP*, the green fluorescence of the GFP chromophore was irreversibly destroyed upon CE540 labeling. In supporting studies, a microplate experiment showed a 7-fold reduction in green fluorescence of GFP* from that of GFP in an isoelectric ampholyte buffer, providing further evidence for labeling-induced denaturation (see FIG. 10).

Experiments performed on the photoimmobilization efficiencies of fluorescently labeled proteins indicated that the native GFP* population showed a $\eta_{green}$ based on native green fluorescence of 10.1%, while the denatured GFP* segment gave $\eta_{red}$ based on its red CE540 signal of 34.5% (see Table 2). Taken together, the high 34.5% value described immobilization of an unfolded form of GFP that may be prone to a greater degree of hydrophobic "pre-covalent" interactions with the benzophenone moieties in the gel matrix. This is consistent with the observation that minor conformational increases in solvent-accessible surface area of protein targets produced disproportionately large increases in diazirine-mediated photolabeling efficiency, suggesting higher protein-label affinity for looser protein conformations.

2. Benchmark Macroscale IEF Slab Gels.

Figure 12:
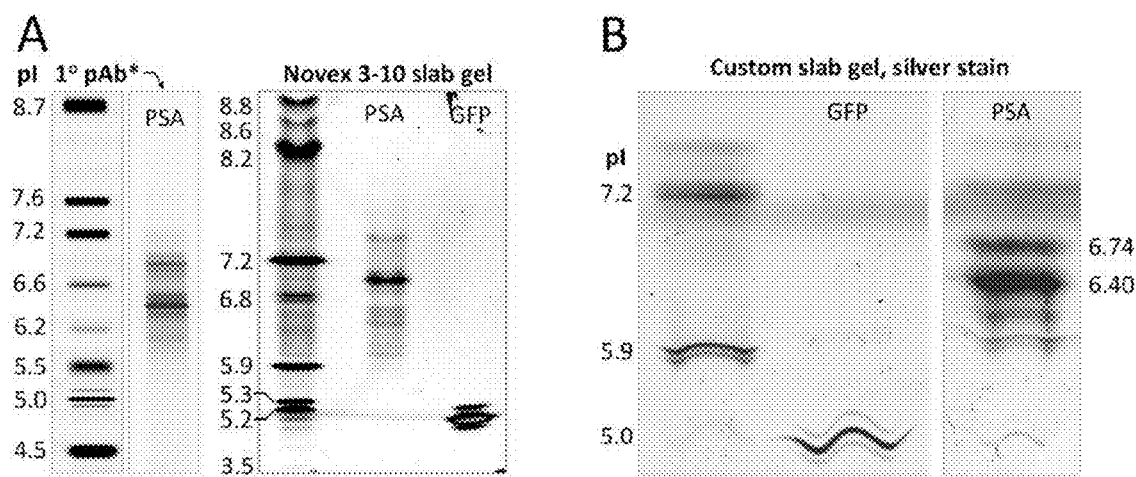
FIG. 12 shows gel images of embodiments of the microfluidic devices and companion slab-gel IEF assays.

Experiments were performed to compare the PSA and GFP readouts in the subject microfluidic device to those of a conventional Novex pH 3-10 IEF slab gel (FIG. 12). Slight differences between the microfluidic device and conventional Novex assays of PSA were mitigated using a custom slab gel with the same buffer composition as the microfluidic device. In contrast, the GFP isoforms arising by differential C-terminal proteolytic cleavage exhibited similar behavior in the chip and Novex gels. This comparison study suggested that the isoform pattern of PSA was sensitive to the presence of the solubilizing additives used in microfluidic device (CHAPS, sorbitol and NDSB-256) that may modulate PSA glycan solvation.

3. Probe Binding Stoichiometry.

Based on antibody probing analyses for purified PSA, the stoichiometry of secondary:primary Ab* binding can be inferred from the ratio of the respective fluorescence traces (FIGS. 4B and 4C). The degrees of labeling of each antibody probe were similar, and the labeling dye was the same (red Alexa Fluor 568). The binding stoichiometry was determined to be approximately 2.5 across the relevant pH range, exhibiting somewhat higher values at the acidic end of the isoform pattern due to a nonspecific contribution of the secondary Ab* to the assay readout.

4. Assays in Isoform "Affinity Mapping" Mode.

Experiments were performed to validate the capability of the microfluidic assay to measure immunoreagent isoform specificity. The isoform distribution of IEF-focused CE540-labeled PSA* was compared to the fluorescence readout after photoimmobilization and probing with mAb* and pAb* (FIG. 5). Alignment between each pair of fluorescence intensity profiles (PSA*, Ab*) was accomplished by applying a translation inferred from their cross-correlation. The translational shift corrected for the slight drift (ca. 190 μm) between imaging of focused PSA* and the photoimmobilization step. The focused PSA* isoform pattern agreed well with that of the probed unlabeled PSA, suggesting a minimal effect of CE540 on the pI values of the native PSA isoforms (compare FIGS. 5A and 5B and FIG. 4A). Ratiometric comparison of the probed and focused PSA* signals suggested spatially uniform probe layering onto immobilized PSA* across the pH region of interest, for both polyclonal and monoclonal detection antibodies (FIGS. 5C and 5D). Some apparent variation across the pH range was induced by diffusional band broadening during photoimmobilization, which had the expected "peak blunting" effect on the probing data. Comparison of the monoclonal and polyclonal probing ratios showed a 2.5:1 pAb*:PSA* stoichiometry (FIG. 5E, assuming a 1:1 stoichiometry inherent in the monoclonal readout with $[Ab^*] \gg K_d$, equilibrium in binding, and negligible PSA "epitope disfigurement" upon immobilization).

5. Target Antigen Immobilization Kinetics.

The reaction between BPMA and the protein target of interest occurred against a background of competing reactions. In some cases, a portion of the BPMA sites formed conjugates with off-target species, such as the ampholytes, gel matrix, sorbitol, NDSB 256 and CHAPS. The combined concentration of these off-target species was >20% wt/vol in the separation medium precursor, constituting a ~$10^6$ fold excess over protein targets in the normal device operating regime. A kinetic scheme that characterized the capture efficiency of a protein target in this regime was developed. Consider parallel irreversible reactions between one reactant (BPMA, species A) and a set of competing species (species $B_i$), one of which is the target protein of interest. The reaction scheme is as follows:

$$A + B_1 \xrightarrow{k_1} P_1$$
$$A + B_2 \xrightarrow{k_2} P_2$$
$$A + B_3 \xrightarrow{k_3} P_3$$
$$\vdots$$
$$A + B_n \xrightarrow{k_n} P_n$$

For low capture efficiencies η, it can be assumed that the free species concentrations do not change appreciably from their initial values, i.e. $b_i \sim b_{i,o}$ (lower case denotes concentration of a species). The rate of disappearance of BPMA is thus:

$$\frac{da}{dt} = -k'_T a$$

Where $$k'_T = \sum_{i=1}^{n} k'_i = \sum_{i=1}^{n} b_{i,o} k_i$$

is a sum of the pseudo-first-order rate constants $k'_i$ of the competing species.

Integrating this expression gives:

$$a = a_o e^{-k'_T t} \quad [1]$$

For generation of a given product $P_i$:

$$\frac{dp_i}{dt} = b_{i,o} k_i a \quad [2]$$

Substituting Equation 1 into Equation 2 and integrating gives:

$$\int_0^{p_i} dp_i = b_{i,o} k_i a_o \int_0^t e^{-k'_T t} dt \Rightarrow p_i = \frac{b_{i,o} k_i a_o}{(k'_T)(1 - e^{-k'_T t})} \quad [3]$$

This result reveals the property that despite each individual reaction having different pseudo-first-order rate constants ($k'_i = b_{i,o} k_i$) the product generation rates are identical and are characterized by a time constant $$\tau = \frac{1}{k'_T} = \frac{1}{\sum_{i=1}^{n} b_{i,o} k_i}.$$

In certain instances, $k'_T \gg b_{target,o} k_{target}$ (subscript target denotes the reaction between the protein target of interest and BPMA), i.e. that the contribution of $k'_{target}$ to $k'_T$ is small given the large excess of off-target species in the reaction. As such, the observed reaction rate is expected to be approximately independent of the target protein concentration. Thus, the observed separation medium immobilization time constant is expected to be invariant across the target calibration curve concentration range.

For long reaction times (t→∞), from Equation 3:

$$p_{target} = \frac{b_{target,o} k_{target} a_o}{k'_T} \Rightarrow \eta = \frac{p_{target}}{b_{target,o}} \times 100 = \quad [4]$$

$$\frac{k_{target} a_o}{k'_T} \times 100 \Rightarrow \eta = \frac{p_{target}}{b_{target,o}} \times 100 = \frac{k_{target} a_o}{k'_T} \times 100$$

Again, for $k'_T$ approximately independent of $b_{target,o}$, the separation medium capture efficiency is also expected to be independent of $b_{target,o}$ (i.e., constant across the calibration curve). Further, increased $k_{target}$, increased $a_o$ (increased [BPMA]), or decreased $k_T$ (decreased concentration of competing species and/or rates of competing reactions) all increase η.

Given that the immobilized target concentration is expected to be a constant fraction of the nominal concentration, and that probe saturation of captured target is guaranteed across the calibration curve at equilibrium for Da ≪ 1 and sufficiently high probe concentration above $K_D$, a linear calibration relationship in the microfluidic system was expected and was observed in the experimental data for PSA.

The benefit of high immobilization surface area is shown by considering the volumetric concentration of BPMA, $a_o$ given a consistent site density $a_{o,s}$ distributed across an immobilization surface with surface area to volume ratio of $$\frac{A_s}{V}: a_o = \frac{a_{o,s} A_s}{V} \quad [5]$$

Substituting Equation 5 into Equation 4 determines a ratio of gel to open capillary capture efficiencies:

$$\frac{\eta_{gel}}{\eta_{cap}} = \frac{\frac{A_{s,gel}}{V}}{\frac{A_{s,cap}}{V}} \qquad [6]$$

The gel surface area $A_{s,gel}$ can be compared to an open capillary $A_{s,cap}$ by approximating the gel structure to be a bundle of packed cylinders in simple cubic arrangement with radius $r_{gel}$ equal to that of the mean pore radius of 120 nm for a 4% T, 2.6% C gel (8), giving:

$$\frac{A_{s,gel}}{V} \sim \frac{2\pi r_{gel} l}{(2[\![ r_{gel})]\!]^2 l} = \frac{\pi}{2r_{gel}}$$

$$\frac{A_{s,cap}}{V} = \frac{2\pi r_{cap} l}{\pi r_{cap}^2 l} = \frac{2}{r_{cap}}$$

From Equation 6:

$$\frac{\eta_{gel}}{\eta_{cap}} \sim \frac{\pi r_{cap}}{4 r_{gel}} = 327$$

With $r_{cap}$=50 μm.

A ~2-3 order-of-magnitude increase in capture efficiency was expected within the gel matrix as compared to the capillary surface, which was confirmed by experimental observation of an ~180-fold improvement in η over that observed from a capillary surface.

6. Probe Binding to Immobilized Antigen.

Experiments were performed to compare the timescales of probe mass transfer and binding for a target analyte ($P_{target}$) immobilized to the wall of an open capillary or to the separation medium. In the following analysis, gel and free solution antibody probe diffusivities of ~4.5×10$^{-12}$ and ~3.4×10$^{-11}$ m$^2$ s$^{-1}$ respectively were used. The capillary tube length y in the open-channel case was the approximate length of an immobilized target peak (~100 μm) with tube diameter 100 μm. The surface concentration of target antigen, $P_{target}$, was that resulting from attachment of focused analyte at η=1% from a 100 nM nominal solution assuming an IEF concentration factor of ~

$$\sim \frac{10.4 \text{ mm}}{0.1 \text{ mm}} \sim 100$$

onto a surface area arising from the cylindrical pore model already described. This gives $P_{target}$=7.6×10$^{-12}$ mol m$^{-2}$. For equivalence of the two cases, the same $P_{target}$ for the open capillary was assumed. The values of $k_{off}$~10$^{-3}$ s$^{-1}$ and $k_{on}$~10$^6$ M$^{-1}$ s$^{-1}$ for Ab-Ag interactions.

Consider an immobilized antigen target $P_{target}$ attached to a capillary wall and probed with a detection antibody C to form a stationary complex X:

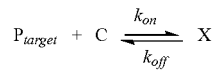

To determine when mass transfer limitation of the reaction timescale will occur due to probe depletion near the reaction surface, the rate equation for immunocomplex formation at the surface is:

$$\frac{dx}{dt} = k_{on} c_s p_{target} - k_{off} x, \text{ units: mol m}^{-2}\text{s}^{-1} \qquad [7]$$

Where $c_s$ is the surface concentration of probe, which is equal to the bulk probe concentration $c_o$ under conditions of reaction limitation, but is between zero and $c_o$ where mass transfer (by convection at the edge of a boundary layer and diffusion through this layer) to the surface is limiting. Neglecting the "off" term in x, the surface flux of probe $\dot{n}_{c_s}$ is:

$$\dot{n}_{c_s} = -\frac{dx}{dt} = -k_{on} p_{target} c_s \qquad [8]$$

Low probe concentration compared to captured target allowed the possibility of mass transfer limitation on surface flux of probe. Thus, $P_{target}$ (mol m$^{-2}$) may be combined with $k_{on}$ (M$^{-1}$ s$^{-1}$) into a pseudo-first-order rate constant k' (standard units of ms$^{-1}$):

$$\dot{n}_{c_s} = -k' C_S, \; k' = k_{on} P_{target} \qquad [9]$$

This simplified kinetic is sufficient to demonstrate the effect of mass transfer resistance in the surface boundary layer on the apparent rate of immunocomplex formation. For convection, diffusion and reaction under simplifying assumptions that the probe is not depleted at the edge of the boundary layer, and that the probe diffusion profile is at steady state (linear c between and $c_o$), it can be shown that:

$$\dot{n}_{c_s} = -\frac{k' c_o}{\left(1 + \frac{k'}{\beta}\right)} \qquad [10]$$

Essentially the probe consumption at the surface depends on a bulk reaction rate k'$c_o$ adjusted by a factor $$\left(1 + \frac{k'}{\beta}\right)$$

accounting for mass transfer resistance in the boundary layer, where β is the mass transfer coefficient (ms$^{-1}$). The dimensionless factor that evaluates the interplay between reaction and mass transfer is the Damkohler number:

$$Da_1 = \frac{k'}{\beta} \qquad [11]$$

Thus for $Da_1 \gg 1$, the reaction speed is greater than mass transfer and the system is mass transfer limited with apparent rate $$\dot{n}_{c_s} = -\frac{dx}{dt} = -\beta c_o;$$

whereas for $Da_1 \ll 1$, mass transfer is greater than the reaction speed and the system is reaction limited with apparent rate $$\dot{n}_{c_s} = -\frac{dx}{dt} = -k'c_o$$

$$\dot{n}_{c_s} = -\frac{dx}{dt} = -k'C_{\overline{s}}.$$

The mass transfer coefficient $\beta$ is a component of the Sherwood number Sh (a mass transport analog of the Nusselt number in heat transfer), which can be estimated from empirical relations determined for different flow properties and interface geometries.

$$Sh = \frac{\beta l}{D} = \frac{\text{mass transfer velocity}}{\text{diffusion velocity}}, \quad [12]$$

where $l$ is a characteristic length in the system.

For the open capillary case, an accurate (within ~1%) relationship for laminar flow in a cylindrical tube is readily available:

$$Sh = \frac{\beta d}{D} = 1.62\left(\frac{d^2 u}{yD}\right)^{\frac{1}{3}} \quad [13]$$

Where d is the tube diameter, y the tube length (length of the reaction zone), u the average velocity in the tube and D the diffusivity of the probe in free solution.

Equations 11 and 13 give $Da_1 < 1$ for probe flowrates greater than $u \sim 1$ mm s$^{-1}$. Further decreases in $Da_1$ occur relatively "slowly" with increases in u due to the cube root dependence of Sh on u. However, given that $\eta \sim 0.01\%$ would be more reasonable in the open capillary case, $Da_1 \ll 1$, and thus the probing step is reaction rather than mass transfer limited.

For probing in the microfluidic device, the target antigen is distributed throughout the channel volume, suggesting that probe driven through the gel pores reacts with captured antigen in a homogeneous fashion (i.e., no boundary layer resistance exists). An alternative Damkohler number has been posited for such electrophoretic "band crossing" reactions:

$$Da_2 = \frac{t_{cross}}{\tau_R} \quad [14]$$

Where $$t_{cross} = \frac{w}{u_{rel}}$$

is the time required for the probe front to sweep through the captured band, which is ~2 sec given an observed probe velocity of $u_{rel} \sim 50$ $\mu$ms$^{-1}$ in the separation medium and a target band width $w = 100$ $\mu$m. Reaction-limited conditions ($Da_2 \ll 1$) was also expected in this framework given the experimental observation that $t_{cross} \ll \tau R$ (see FIG. 1F).

$Da_{1,2} \ll 1$ such that the relevant probe transport timescale is substantially smaller than the reaction timescale (i.e., mass transfer is faster than the reaction). Thus, the binding reaction at the surface may be focused on depletion of captured target as it is occupied by relatively unconstrained delivery of probe:

$$\frac{dx}{dt} = k_{on} c_s p_{target} - k_{off} x, \quad [15]$$

This equation is identical to Equation 7, but $c_s \sim c_o$ and $P_{target} = (P_{target,total} - x)$ where $P_{target,total}$ is the total concentration of immobilized target. Thus:

$$\frac{x(t)}{p_{target,total}} = \frac{\frac{c_o}{K_D}}{1 + \frac{c_o}{K_D}}\left(1 - e^{-(k_{on} c_o + k_{off})t}\right) \quad [16]$$

for $Da_{1,2} \ll 1$

Where $$K_D = \frac{k_{off}}{k_{on}}$$

is the equilibrium dissociation constant for the Ab-Ag interaction.

The bulk probe antibody concentration $c_o$ was in large excess compared to $K_D$ at $c_o > 100$ $c_o > 100$ nM, giving $$\tau_R \lesssim \frac{1}{k_{on} c_o} = 10$$

$$\tau_R \lesssim \frac{1}{k_{on} c_o} = 10$$

sec ($t_{cross} \ll \tau_R$, as observed experimentally), and at equilibrium $$\frac{x(t)}{p_{target,total}} = \frac{\frac{c_o}{K_D}}{1 + \frac{c_o}{K_D}} \sim 1$$

(i.e., probe binding saturates captured target).

7. Determination of Free Solution and in-Gel Diffusivities.

The diffusion coefficient for GFP in 4% T, 2.6% C polyacrylamide gel was determined by defocusing to be $2.05 \times 10^{-7}$ cm$^2$ s$^{-1}$ (FIG. 3A). The diffusion coefficient for a given protein in a polyacrylamide matrix can be estimated via an adjusted Stokes-Einstein diffusivity:

$$r_H = 0.595 \, (M_W)^{0.427} \quad [17]$$

$$D = \frac{k_B T}{6\pi\mu r_H} e^{-k_c r_H \varphi^{0.75}} \quad [18]$$

$r_H$ is the protein hydrodynamic radius, $M_w$ the protein molecular weight in kDa, $k_E$ is Boltzmann's constant, T temperature, $\mu$ the viscosity of the medium ($\mu \sim 1.26 \times 10^{-3}$ Pa·s for a 10% sorbitol solution (17)), $k_c = 0.45$ Å$^{-1}$, $\varphi$ the polymer volume fraction.

This relationship gives a diffusivity of GFP in 4% T, 2.6% C polyacrylamide gel of $\sim 2.5 \times 10^{-7}$ cm$^2$ s$^{-1}$, which is within 20% of the value measured by defocusing ($2.05 \times 10^{-7}$ cm$^2$ s$^{-1}$). Thus, the diffusivity for a probe antibody can be estimated by similar means to be $\sim 4.5 \times 10^{-8}$ cm$^2$ s$^{-1}$ in the gel and $\sim 34 \times 10^{-7}$ cm$^2$ s$^{-1}$ in free solution.

TABLE 2

Capture efficiencies η (%) under focusing conditions. CE540-labeling indicated by "*", fluorescence emission channel used to determine η denoted by "green" and "red".

| Target | pH | $\eta_{green}$ | $\eta_{red}$ |
|---|---|---|---|
| GFP | ~5.2 | 1.30 ± 0.17 (n = 44) | — |
| GFP* | ~5.2 | 10.1 ± 1.91 (n = 8) | 34.5 ± 3.04 (n = 8) |
| PSA* | ~6.5 | — | 9.92 ± 0.86 (n = 3) |
| Pharmalyte 3-10* | 5.0 | — | 7.17 ± 1.95 (n = 4) |
|  | 7.5 | — | 13.3 ± 1.70 (n = 4) |

TABLE 1

Buffers used, all % values are w/v unless stated otherwise.

| | Vol (μl) | Component | Final |
|---|---|---|---|
| Gel Precursor (BPMA+) | 56.3 | 26.7% CHAPS | 3% |
| | 66.7 | 1.5M NDSB 256 | 200 mM |
| | 62.5 | 80% sorbitol | 10% |
| | 66.7 | 30% T, 2.6% C (37.5:1 premix) | 4% T, 2.6% C |
| | 40 | Pharmalytes 3-10 pH 9.9 (25%) | 2% |
| | 22.5 | 100 mM BPMA in DMSO | 4.5 mM BPMA, 4.5% DMSO v/v |
| | 177.3 | DI H$_2$O | |
| | 4 | 10% APS | 0.08% |
| | 4 | 10% TEMED v/v | 0.08% v/v |
| Total | 500 | | |
| Loading Buffer | 112.5 | 26.7% CHAPS | 3% |
| | 133.3 | 1.5M NDSB 256 | 200 mM |
| | 125 | 80% sorbitol | 10% |
| | 55.6 | Pharmalytes 3-10 (36%) | 2% |
| | 45 | DMSO | 4.5% v/v |
| | 478.5 | DI H2O | |
| Total | 950 | | |
| Catholyte | 168.8 | 26.7% CHAPS | 3% |
| | 200 | 1.5M NDSB 256 | 200 mM |
| | 187.5 | 80% sorbitol | 10% |
| | 150 | 10x Novex catholyte | 1x (20 mM lysine, 20 mM arginine) |
| | 67.5 | DMSO | 4.5% v/v |
| | 726.2 | DI H2O | |
| Total | 1500 | | |
| Anolyte | 1500 | 10x Bio-Rad anolyte | 10x (70 mM H$_3$PO$_4$) |
| Total | 1500 | | |
| Gel Buffer | 112.5 | 26.7% CHAPS | 3% |
| | 133.3 | 1.5M NDSB 256 | 200 mM |
| | 125 | 80% sorbitol | 10% |
| | 80 | Pharmalytes 3-10 pH 9.9 (25%) | 2% |
| | 45 | DMSO | 4.5% v/v |
| | 504 | DI H2O | |
| Total | 1000 | | |
| Washout/Probe Buffer | 168.8 | 26.7% CHAPS | 3% |
| | 200 | 1.5M NDSB 256 | 200 mM |
| | 187.5 | 80% sorbitol | 10% |
| | 22.5 | 1M glycine NaOH pH 9.9 | 15 mM glycine |
| | 67.5 | DMSO | 4.5% v/v |
| | 853.8 | DI H2O | |
| Total | 1500 | | |

Example 2

Figure 13:
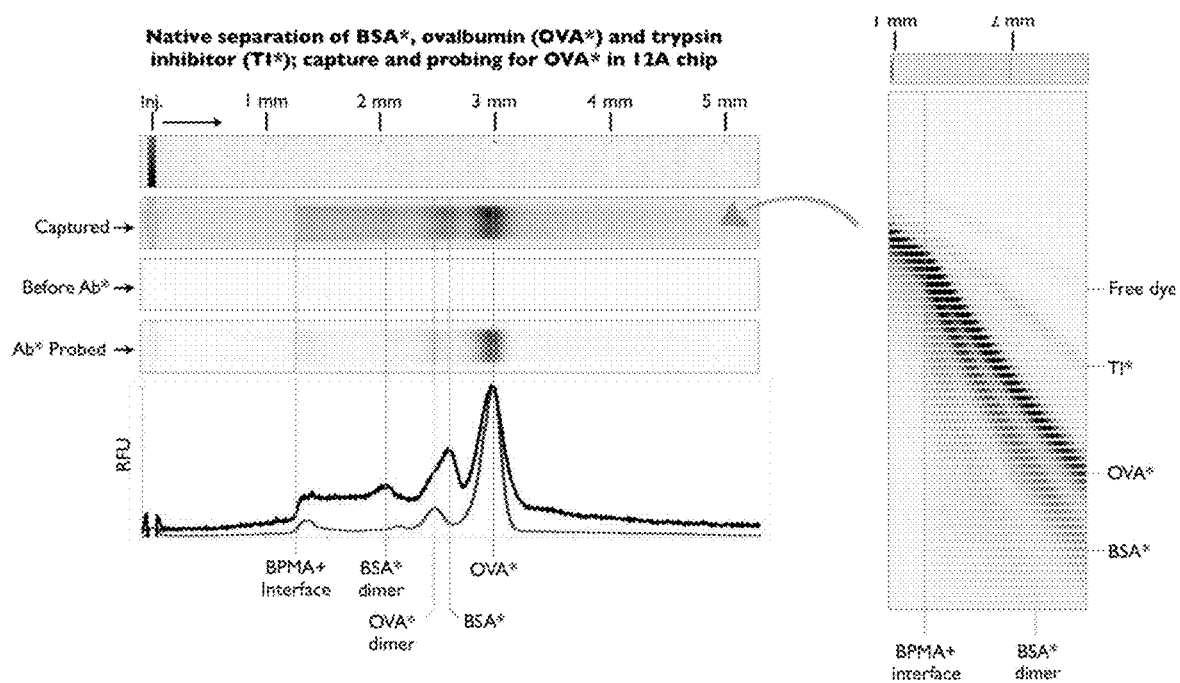
FIG. 13 shows experiments of the integration of microfluidic native size-based separation and immunoprobing in a microfluidic device according to embodiments of the present disclosure. Separation of a mixture of fluorescent proteins (top trace) was performed in the gel from left to right from an injection zone at a cross-channel T chip. Photocapture was initiated via application of UV light. Washout of unbound protein and subsequent immunoprobing for ovalbumin (OVA*) was performed in situ, with specific fluorescent readout (bottom trace).
Figure 14:
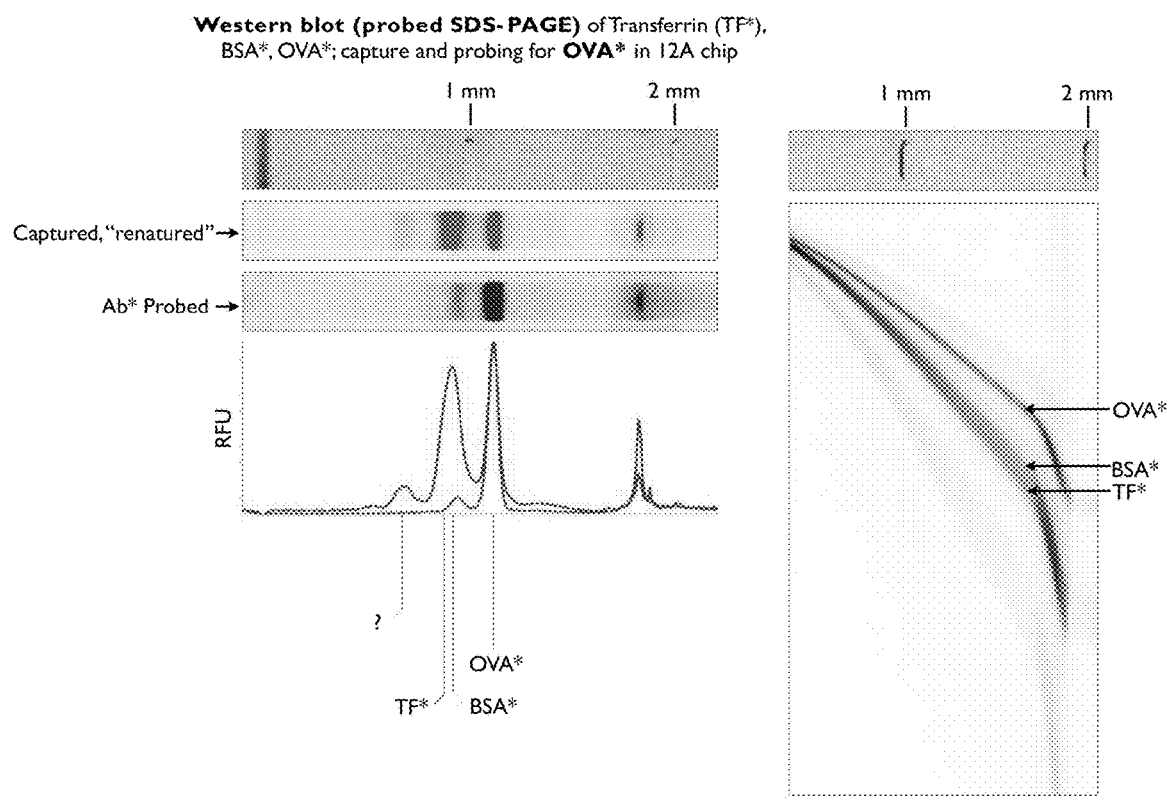
FIG. 14 shows an experiment performed similarly to FIG. 13, except with reduced and denatured sample (e.g., SDS-PAGE), according to embodiments of the present disclosure. Sample preparation with SDS, DTT reducing agent and heating was performed in the vein of traditional Laemmli SDS-PAGE. In-situ immunoprobing (red) was then performed for ovalbumin after capture of separated species (green) onto the separation medium and washout of excess SDS detergent. This experiment demonstrates SDS-PAGE with immunoprobing (typically referred to as "Western blotting") performed in an integrated microfluidic device.

The subject microfluidic device can be used to perform size based separations linked to immunoprobing in both native and SDS-PAGE variants. Embodiments that include size based separation (SDS-PAGE) and immunoprobing may facilitate a microfluidic "western blot". Experiments were performed that show native (FIG. 13) and SDS-PAGE (FIG. 14) separations of Alexa Fluor 488-labeled fluorescent protein ladder species with subsequent photocapture onto the separation medium and in-situ probing for ovalbumin (OVA*) with a specific antibody labeled with Alexa Fluor 568. The assay was performed with unlabeled target analytes, and was directly analogous to Western blotting, with significantly reduced assay time, reagent and sample requirements as compared to typical Western blotting.

The first separation step was performed across a discontinuous polyacrylamide interface built using two-step chemical polymerization of a high percentage (6% T) separation gel precursor (BPMA+) and a low percentage (3.5% T) loading gel precursor (BPMA−). The high percentage precursor was chemically polymerized against an air interface at a microfluidic cross-channel injection T.

Once the high percentage separation gel was polymerized, the low percentage precursor solution was added, wetting directly against the separation gel interface at the injection T. The low percentage solution was then polymerized chemically as well, forming a discontinuous separation gel analogous to those used in macroscale polyacrylamide slab gels.

After timing and recording an initial separation, the second separation was performed, at which point the E field was stopped and UV light applied via a 4× microscope objective. Washout of excess protein was done rapidly directly after capture. The captured ladder profile was repeatable, with capture efficiencies of approximately 50%, regardless of species identity. Introducing and washing out the fluorescent antibody for ovalbumin produced quantitative detection duty in both native (FIG. 13) and SDS-PAGE (FIGS. 14 and 16) assay versions.

Figure 15:
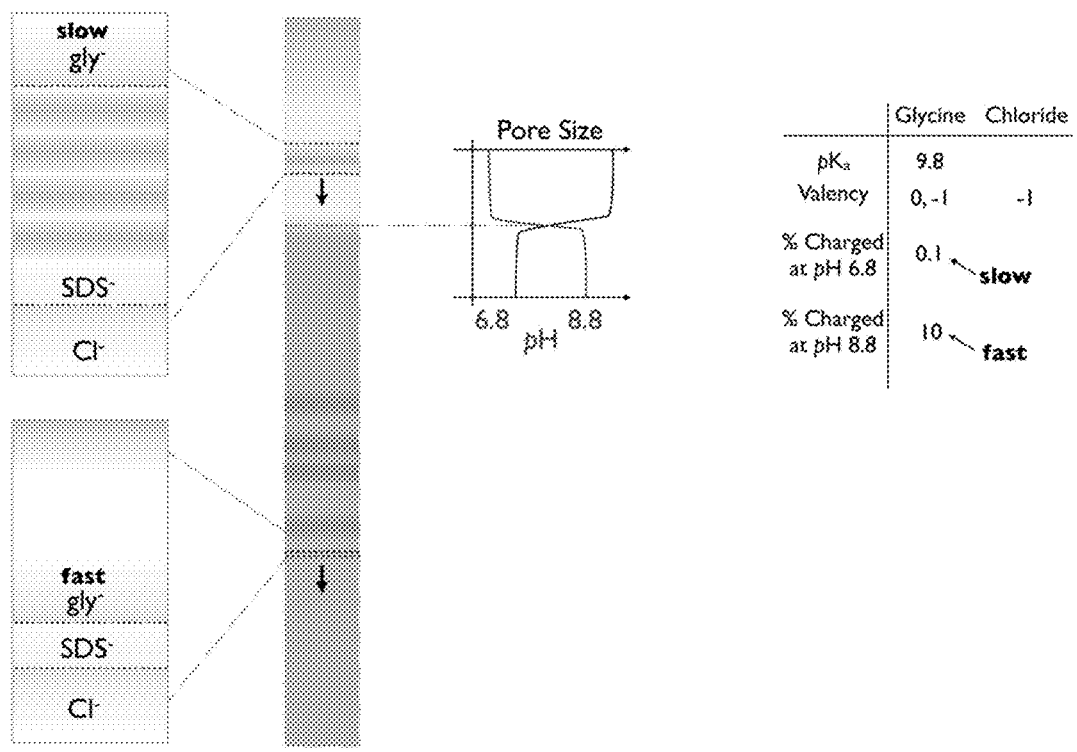
FIG. 15 shows gel images of transient isotachophoretic stacking of proteins induced by a step change in channel pH, which manipulated the mobility of a glycine trailing ion similar to traditional Laemmli SDS-PAGE, according to embodiments of the present disclosure. The initial diffuse sample zone was stacked in the low pH region before entering a higher pH region in which the glycine trailing ion overtook the protein bands, causing them to separate by size.
Figure 16:
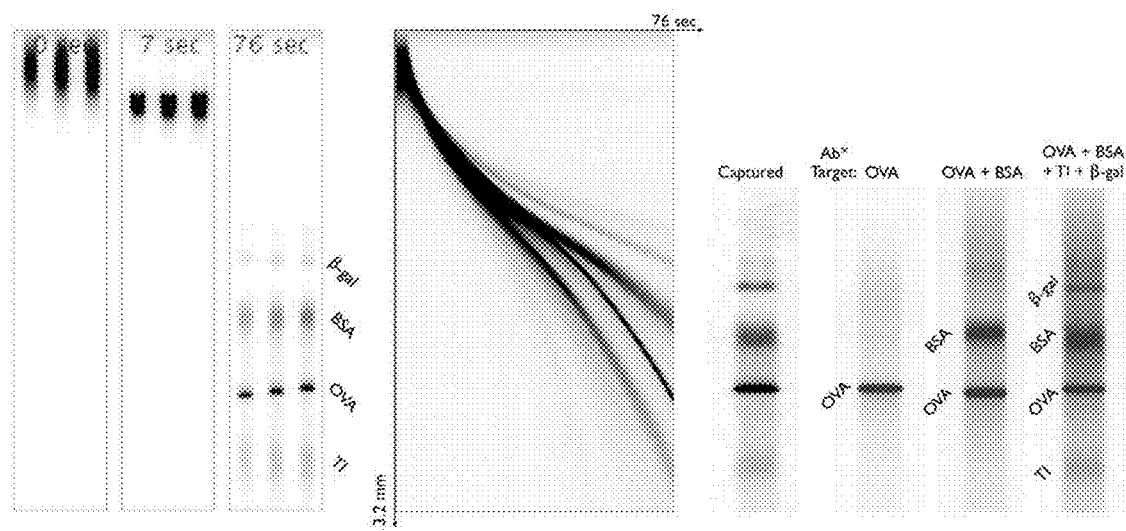
FIG. 16 shows gel images of single-channel SDS-PAGE with stacking by transient ITP (frames 1 and 2 at left), separation of proteins by size (frame 3 and continuous plot at center), and probing for multiple analytes in separate devices following immobilization (antibody fluorescence data at right), according to embodiments of the present disclosure. β-gal is β-galactosidase.
Figure 17:
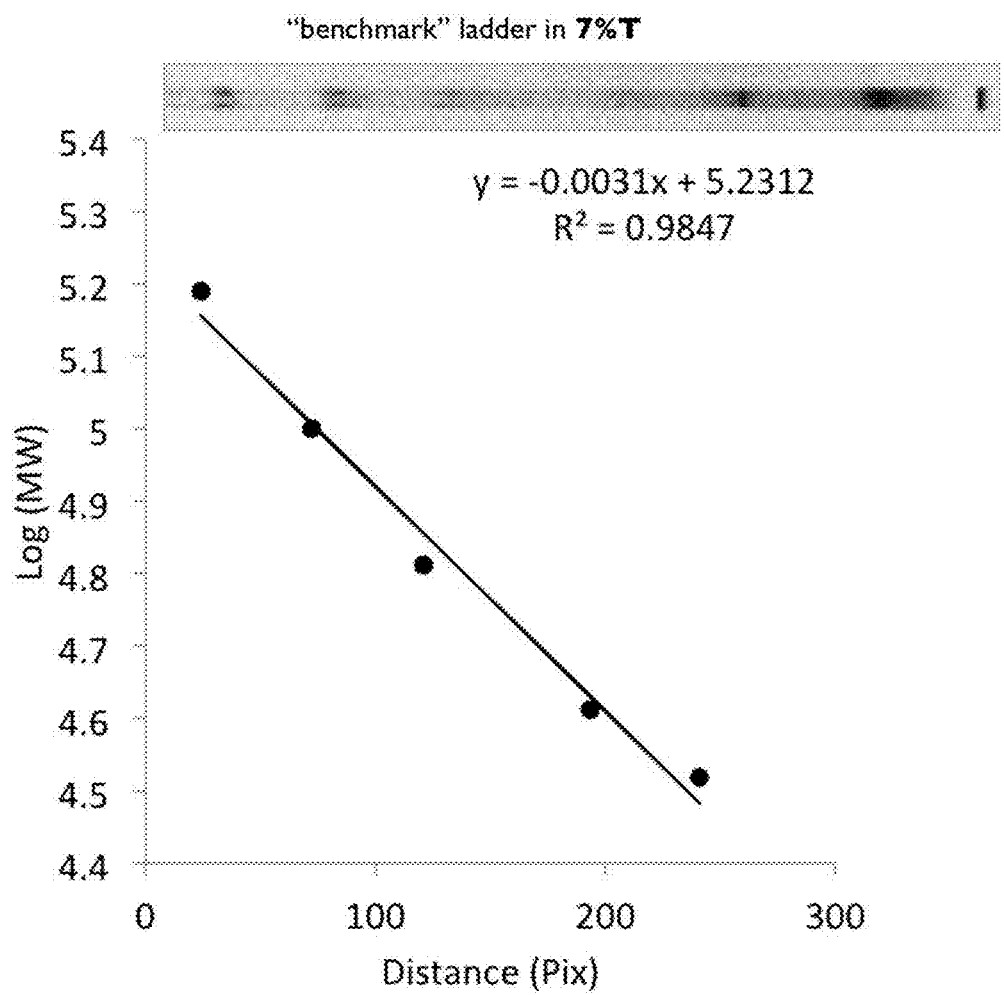
FIG. 17 shows a graph of separation of a benchmark protein ladder by SDS-PAGE, showing the expected log-linear relationship, according to embodiments of the present disclosure.

A single-microchannel approach was also developed that allowed the same SDS-PAGE separation to be performed in a reduced complexity device that included two (rather than four) access wells. Sample stacking was achieved by transient isotachophoresis followed by a zone electrophoresis process in direct series (FIG. 15). In some embodiments, sample stacking improved band resolution, improved assay sensitivity and removed the need for T-injection. A similar separate-capture-probe strategy then allowed multiplexed analyte detection (FIG. 16, four proteins probed simultaneously). Analyte sizing conformed to the expected log-linear relationship between protein molecular weight and migration distance in the device (FIG. 17).

Example 3

Experiments were performed using a microfluidic device according to embodiments of the present disclosure for western blotting. In certain embodiments, the assay duration was reduced from 3-18 hours to 10-60 min as compared to typical western blotting. In some instances, 5-plex simultaneous analyte detection and quantitative readout was performed. In a single microchannel, the subject microfluidic device performed stacking sodium dodecyl sulfate-polyacrylamide gel electrophoresis (SDS-PAGE), protein immobilization with SDS removal (blotting), and subsequent antibody probing. The scalable, high-throughput nature of microfluidic design allowed 54-plex parallelization, and 10 min assay times. A photopatternable (blue light) and photoreactive (UV light) polyacrylamide gel forms the separation medium for the assay. The polymer included both an SDS-PAGE separation matrix with a defined stacking interface and, after brief UV-switching, a protein immobilization matrix offering high capture efficiencies (>75%, obviating blocking). Experiments were performed to analyze NFκB in 293T cell lysate yielding femtogram sensitivities (tens of transfected cells per 3 μl sample). Antibody requirements were typically <1 ng per blot, which represented a 1.000-fold reduction over conventional immunoblotting. Experiments were performed to validate a rapid confirmatory HIV diagnostic requiring <1 μl of human serum using p24 and gp120 bait antigens.

Results and Discussion

Dual Band-Tunable PACTgel for Protein Separations and Capture.

Figure 18:
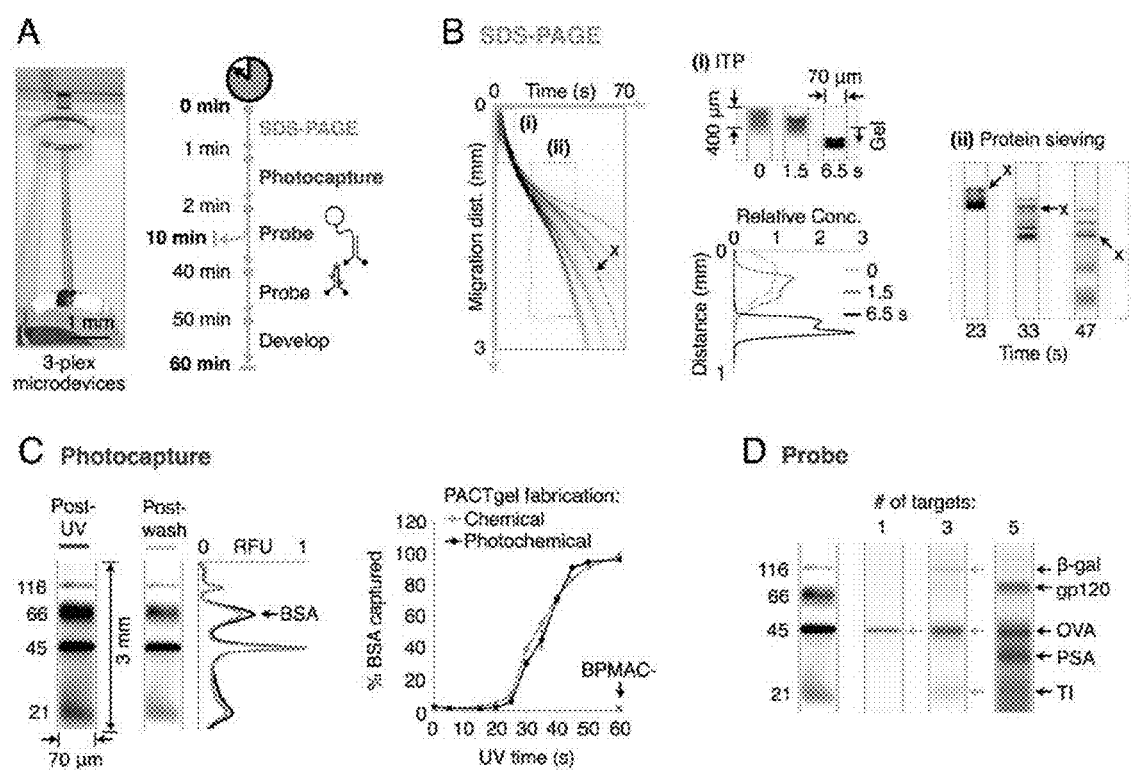
FIG. 18 shows experiments for rapid, multiplexed micro-Western blotting in a single microchannel, according to embodiments of the present disclosure.

Microchannels were filled with a dual spectral band photoactive protein capture gel with tunable porosity separation and blotting polymer (FIG. 18A). Using microfluidic integration and the functional polymer, all steps from isotachophoretic (ITP) stacking during sample injection to weight-based separation of denatured protein analytes (SDS-PAGE, FIG. 18B) to immunoblotting with fluorescently labeled primary and secondary antibodies were performed in one microfluidic channel in 10-60 min. The polyacrylamide-based separation medium was built using a riboflavin-driven photopolymerization strategy that preserved a spectrally distinct UV light-responsive capture functionality of the gel. Photochemically fabricated separation media were patterned using blue light via photomask exposure to provide fine spatial control over gel porosity and sieving interface position (coefficient of variation, CV, of 3.5%, n=60). Control of gel porosity may facilitate assay repeatability across the full 54-channel implementation. Separation media were also optimized for quantitative protein analyte capture following SDS-PAGE separations (>75% capture efficiencies for all analytes) with UV exposure times of 45-60 s applied via a 4× microscope objective (FIG. 18C). Due to the benzophenone-functionalized, light-activated character of the gel, no separate blocking steps were needed after protein immobilization. Simultaneous probing of 5 analyte species was performed using antibody cocktails applied in a single electrophoretic step (FIG. 18D).

Micro-Western Blot Assay Design.

Figure 19:
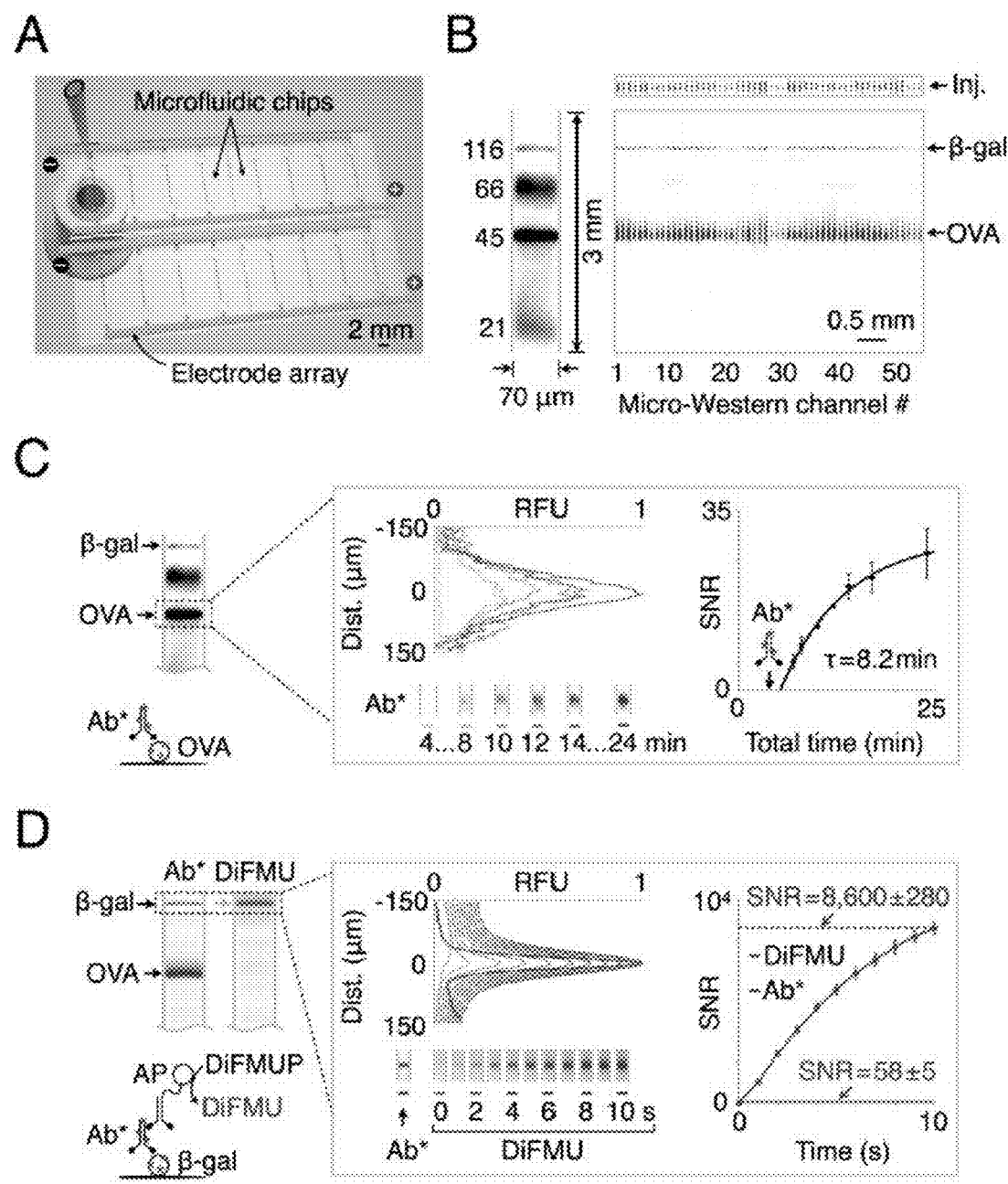
FIG. 19 shows a micro-Western blot for quantitative, rapid, and high-sensitivity readout modes, according to embodiments of the present disclosure.

In some embodiments, microfluidic chips for micro-Western blot included 4 sample throughput in technical triplicate (FIG. 19A). Parallelization was scalable by altering the number of chips interfacing with the electrode array. As shown in FIG. 19B, 54 microchannel throughput (18 samples) was performed, with increased throughput achievable with adjustment to the UV exposure and electrical connectivity hardware. Channels included one access well pair per triplicate blot, and channel widths were 70 μm. Between-device peak area CVs for identical samples probed simultaneously for ovalbumin (OVA) and β-galactosidase (β-gal) were 25% each, with the ratio of their peak areas varying with a CV of 14.7%. The measured reproducibility and use of internal migration controls allowed data comparison across devices and chip modules. In addition to the stacking gel pore-size discontinuity employed here for transition from ITP to SDS-PAGE, spatial control over gel porosity allowed formation of e.g., separation gels with gradients in pore size.

Micro-Western Blot Readout Modes.

Experiments were performed to test three methods of analyte detection. In some instances, dynamic imaging of fluorescent antibody probe accumulation at the site of captured analytes was performed. This dynamic imaging approach yielded a primary antibody probing time constant of 8.2 min for a roughly 1 µM OVA band captured on the separation medium after SDS-PAGE (FIG. 19C). Probe was electrophoretically introduced 4 min after the start of the assay, and required ~1 min to migrate through the gel pores to the immobilized OVA band. A probe band SNR of >10 was recorded for a 10 min total assay time. In some cases, the rapid probing kinetics may be due to electrokinetic through-pore probe delivery that is not significantly impeded by surface boundary layer diffusion resistances. Dynamic monitoring of target peak SNR achieved an acceptable readout signal and assay time.

Experiments were also performed using both primary and secondary fluorescently labeled antibody probes and an endpoint readout with washout of excess probe. This approach resulted in higher SNRs over the full separation range while still maintaining relatively rapid assay times of less than 60 min (FIG. 18D and FIG. 19B).

Experiments were also performed to achieve a high-sensitivity detection method using enzyme-amplified secondary antibody detection. An alkaline phosphatase-conjugated secondary antibody and a charged fluorogenic substrate (6,8-difluoro-4-methylumbelliferyl phosphate or DiFMUP, FIG. 19D) suitable for electrophoretic introduction into separation medium-filled microchannels was used.

High Resolution Single Microchannel SDS-PAGE.

A transient-ITP buffer arrangement using a tris-glycine SDS-PAGE system was used as the first assay stage (FIG. 18B). During the stacking phase, a diffuse plug of protein injected at the microchannel entrance was electrophoretically compacted into an ~200 µm zone prior to electromigration across a sharp sieving gel interface (a 7.5% T sieving separation medium at ~400 µm into the microchannel). Protein electromigration through the gel interface caused a transition from transient ITP to SDS-PAGE, as the trailing glycine electrolyte overtook the stacked protein zones. Stacking achieved >2-fold sample preconcentration and minimized injection dispersion, increasing analyte resolution during the sieving phase. In this implementation, band ordering in the stack was not necessarily governed by molecular weight during ITP, thus, in some instances, dynamic band reordering was observed during the brief transition from ITP to PAGE (see band "x" in FIG. 18B).

On-chip SDS-PAGE yielded a log-linear molecular weight versus migration distance relationship ($R^2 > 0.98$ for MW marker proteins), providing reliable sizing over the 20-150 kDa analyte range. The sieving gel formulation was tunable for enhanced resolution over specific weight ranges of interest. Immobilized peaks with differences in weight of >19% were resolvable (separation resolution $R_s \geq 1$). This micro-Western stacking and sizing performance resulted in a resolution competitive with both conventional slab-gel and capillary western blotting systems. However, the micro-Western system achieved these results in a 3 mm separation distance; >10-fold shorter than either conventional technique. Minimized separation distances resulted in a decrease in assay time during SDS-PAGE, which typically requires 60 s to complete on-chip, a 40- to 90-fold reduction in time as compared to conventional techniques.

Rapid, High Efficiency Analyte Blotting by Photocapture.

Directly following SDS-PAGE a 60 s or less exposure to UV light activated protein capture on the channel-filling separation medium. Pendant benzophenone groups built into the polyacrylamide gel scaffold via a methacrylamide comonomer (N-[3-[(4-benzoylphenyl)formamido]propyl] methacrylamide, BPMAC) underwent hydrogen abstraction and covalent coupling to nearby biomolecules via a radical mechanism. The separation medium capture efficiencies of fluorescently-labeled marker proteins (assayed simultaneously with unlabeled target proteins) for a 45 s UV exposure period were measured and found to be: 107.9±0.6%, 85.4±3.5%, 103.4±3.8%, and 75.2±0.8% for β-gal (116 kDa), bovine serum albumin (BSA, 66 kDa), OVA (45 kDa) and trypsin inhibitor (TI, 21 kDa), respectively (all±SD, n=3, respective within- and between-device coefficients of variation of <5% and <20% for each band, FIG. 18C).

High capture efficiencies were maintained for protein concentrations of at least 100 pg nl$^{-1}$ (~$10^9$ proteins nl$^{-1}$) due to an excess of benzophenone capture sites (~$10^{12}$ sites nl$^{-1}$) distributed throughout the separation medium. In contrast, a BPMAC-negative control separation medium lacking capture sites exhibited negligible protein blotting (FIG. 18C). High capture efficiency after SDS-PAGE may be due to analyte denaturation. Denaturation may expose buried protein residues to the sieving matrix, thus promoting hydrophobic interactions between the unfolded analytes and the pendant separation medium benzophenone groups. In some cases, the reduced requirement for protein solubilizing agents (e.g., detergents) in SDS-PAGE as compared to IEF may reduce steric barriers to productive coupling. The 75-100% separation medium capture efficiency range was comparable to conventional electrotransfer blotting efficiencies on polymer membranes and was a 10.000-fold improvement over conventional capillary surface-capture (0.01% for green fluorescent protein). Completion of analyte capture in 60 s was a ~90-fold increase over typical membrane electrotransfer timescales in conventional bench top western blotting.

Characterization of chemically and photochemically fabricated separation media showed a sigmoidal dependence of fluorescently labeled BSA capture efficiency on UV exposure time (FIG. 18C). The low capture efficiencies obtained for exposure times of less than ~20 s may be due to an initial inhibitory phase caused by scavenging of reactive benzophenone sites by dissolved oxygen prior to a productive phase of analyte capture onto the separation medium. The capture time courses for the two separation media formulations were substantially identical, with complete BSA capture measured in each for UV exposure times of greater than ~45 s. This result confirmed that the use of blue light with a wavelength of approximately 470 nm for spatially directed, photochemical separation medium fabrication does not compromise subsequent protein analyte blotting.

Enzyme-Amplified Micro-Western Blot Readout.

Following photocapture, analyte bands were probed with fluorescently-labeled primary and secondary antibodies via active electrophoretic introduction and washout from the nanoporous separation medium. Use of an enzyme-amplified assay detection protocol yielded SNR increases of >100-fold in a 10 s reaction time at a ~1 µM β-gal analyte band (FIG. 19D). This increase may be due to in situ conversion of a charged DiFMUP substrate by an alkaline phosphatase-conjugated secondary antibody. The blue fluorescent DiFMU product diffused away from the production site even under stopped (floating) electric field, presenting a tradeoff between the amplification factor and the separation resolution of the blot. In certain embodiments, precipitating phosphatase substrates may minimize this tradeoff.

Quantitative Micro-Western Blots with Gold-Standard Validation.

Figure 20:
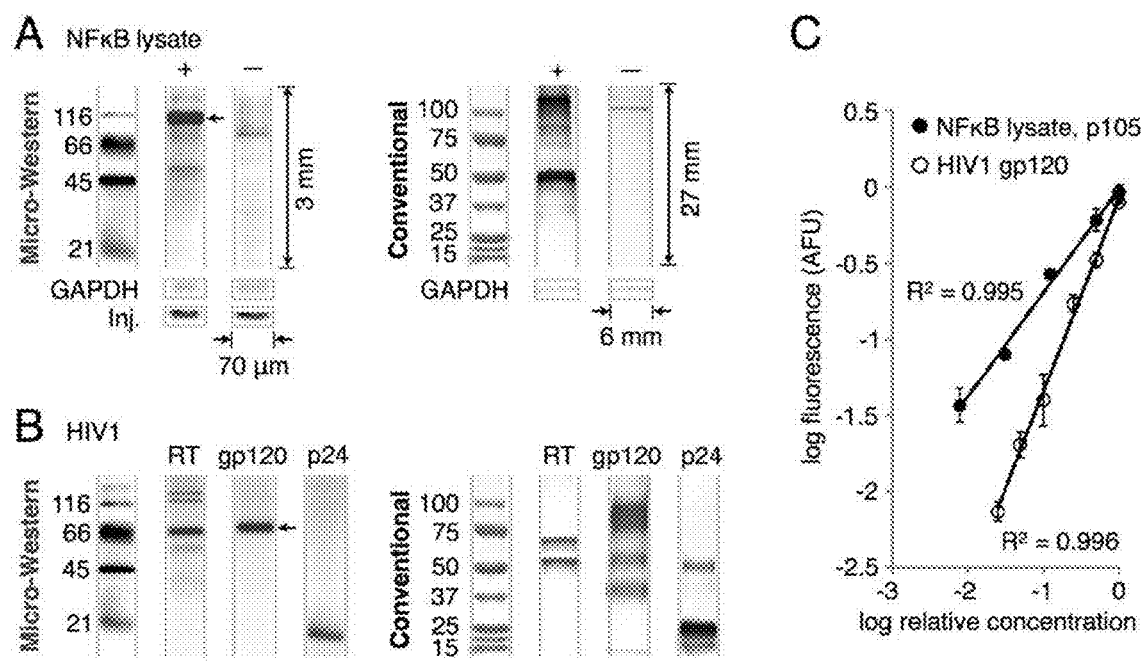
FIG. 20 shows experiments for the validation of micro-Western blotting for lysates and purified proteins, according to embodiments of the present disclosure.

To validate the microfluidic western blot, experiments were performed to assay for the transcription factor NFκB (p105, p50) in lysate from an NFκB-transfected 293T cell line (FIG. 20A). A primary and a fluorescently-labeled secondary antibody were employed for immunoprobing. Assays of NFκB transfected lysate and untransfected negative controls yielded similar probing patterns in on-chip and conventional formats. In addition to conventional GAPDH probing, measurement of the total injected zone fluorescence for the weight ladder proteins was a useful loading control in micro-Western assays.

Experiments were performed to assay for several purified human immunodeficiency virus (HIV) proteins (FIG. 20B). The weights of the major bands of viral reverse transcriptase and the envelope glycoprotein gp120 determined from micro- and conventional slab-gel western blotting agreed to within 12%. Within-device CVs for all bands were <2% (n=3 for each). Minor bands for both gp120 (56, 40 kDa) and p24 (49 kDa) observed only on conventional western blots were likely attributable to the factors that differ between the macro- and microscale workflows, including differences in blotting efficiency, in the SDS-PAGE and probing buffer systems, and in the degree of analyte renaturation prior to immunoprobing.

Quantitative micro-Westerns were achieved over a linear dynamic range of 2.1 logs with a 5 nM LOD for gp120 (FIG. 20C); on par with enzyme-amplified chromogenic signal development in conventional western blots. The average within-device peak area CV across the calibration curve data of FIG. 20C was 14% (n=11 points). The NFκB p105 LOD was reached at 128-fold dilution of a 0.5 mg ml-1 lysate, corresponding to the total protein mass from ~60 transfected mammalian cells in the 3 µl sample volume. Stated another way, the detected analyte mass represented <1% of the mass of a single cell on the basis of the 0.2 nl volume injected into each microchannel. These detection limits were achieved in the micro-Western blot without use of amplified detection. The micro-Western LOD of 1.2 ng per 3 µl sample or 70 fg of gp120 per 0.2 nl injected volume implied the ability to detect 25,000 virus particles on a gp120 basis (4-35 copies per virion), or as few as 100 particles for p24 (5,000 copies per virion). Concentration-based LODs may be reduced by 2-3 orders of magnitude, for example by using enzyme-amplification (see FIG. 19D).

Micro-Western blotting consumed <1 ng of each antibody, in contrast with ~1 µg consumed in conventional western blotting. Similarly, the total wash and transfer buffer requirement was reduced by 1.000-fold in the microfluidic system.

HIV Diagnosis from Human Sera.

Figure 21:
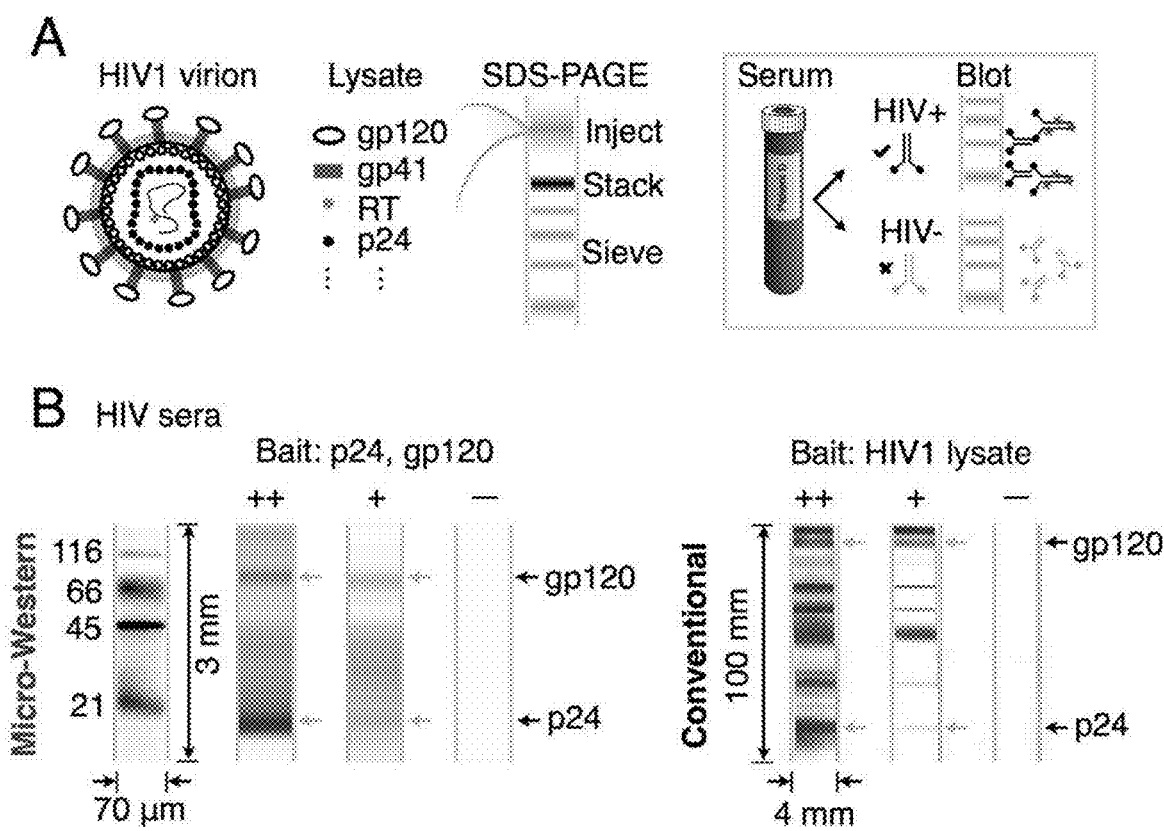
FIG. 21 shows 60 min micro-Western blots for human immunodeficiency virus (HIV) antibody detection in human sera, according to embodiments of the present disclosure.

Experiments were performed using the micro-Western as a HIV diagnostic assay for human sera. Typically, HIV diagnosis employs a conventional western blot as the final (confirmatory) assay, following a positive ELISA-based screening result. In a 6-18 hr workflow, an HIV viral lysate is subjected to SDS-PAGE and immunoblotting (FIG. 21A). A 1:100 dilution of patient serum is incubated with a nitrocellulose strip carrying the HIV protein bands. Any HIV-reactive antibodies in the serum bind to specific HIV proteins on the strip. A positive result is indicated if two or more of the p24, gp41 and gp120/160 bands exhibit reactivity at least as intense as that of the p24 band on a blotting strip subjected to a weakly reactive control serum.

Experiments were performed using the micro-Western blot to assay human sera against purified gp120 and p24 HIV proteins (FIG. 21B). A mixture of these antigens was subjected to the micro-Western assay, the last step being probing of the immobilized antigens with 1:100 diluted human serum. Specific serum reactivity to each "bait" protein was determined using a fluorescently labeled secondary antibody directed to human IgG on the separation medium. The resulting dose response was consistent with the expected antibody titer in each of three serum samples (strongly reactive, weakly reactive, non-reactive); in accordance with the U.S. Centers for Disease Control and Prevention guidelines for determining HIV infection in humans.

Materials and Methods

Microfluidic Assay Instrumentation.

Glass microchannels were functionalized with acrylate-terminated self-assembled monolayers. The separation medium precursor contained 7.5% w/v total acrylamide (7.5% T) with 2.7% of the total as the crosslinker N,N'-ethylenebisacrylamide (2.7% C). BPMAC monomer was added to precursor solutions at 3 mM from a 100 mM stock in DMSO (0.3 mol % with respect to acrylamides). BPMAC− precursors contained an equivalent volume of DMSO lacking BPMAC. Gel precursor buffer was 37.5 mM tris titrated to pH 8.8 with HCl, 0.1% SDS, 0.1% Triton X-100. The initiators ammonium persulfate (APS, 0.015%; A3678, Sigma-Aldrich, St. Louis, Mo.), N,N,N',N'-tetramethylethylenediamine (TEMED, 0.05% v/v; T9281, Sigma-Aldrich) and riboflavin 5' monophosphate (0.0006%; F1392, Sigma-Aldrich) were added just before introduction of degassed precursor to channels by capillary action. Separation gels and interfaces were photochemically fabricated by 3 min chip exposure to a collimated blue (470 nm) LED source (M470L2, Thorlabs, Newton, N.J.) yielding ~2.2 mW cm$^2$ at the chip plane for a 470 nm probe setting (LaserCheck light meter; 1098293, Coherent, Santa Clara, Calif.) through a custom chrome photomask (Photo Sciences Inc., Torrance, Calif.), followed by another 3 min exposure step following exchange of gel precursor at access wells with gel precursor buffer. Chemically fabricated gels did not require blue light exposure, and were made similarly from precursors containing 0.08% of each of APS and TEMED, but which lacked riboflavin.

Micro-Western Blot Protocol.

Samples were combined with a fluorescent molecular weight marker cocktail in SDS-PAGE sample buffer (50 mM tris titrated to pH 6.8 with HCl, 2% SDS, 40 mM dithiothreitol), heated at 90° C. for 3 min, and loaded immediately after cooling to room temperature. Sample loading was performed electrophoretically at 100 V cm$^{-1}$ for 5 s. Sample was removed and the injection well filled with SDS run buffer containing glycine as a trailing ion for transient ITP (25 mM tris, 192 mM glycine, pH 8.3, 0.1% SDS, 0.1% Triton X-100, 3% DMSO). Sample injection was performed under constant-current conditions of 0.7 µA per well pair, producing a voltage ramp during SDS-PAGE from 50-350 V cm$^{-1}$ over a 60 s separation time. SDS-PAGE was imaged in real time via a 4× epi-fluorescence microscope objective, voltage stopped and UV applied via the objective at ~40 mW cm-2 for 45 s directly after separation was complete. Whole-channel green fluorescence imaging for marker proteins was conducted under 10× magnification, prior to electrophoretic washing of the separation medium to remove uncaptured protein, 1 min each with SDS run buffer and plain run buffer lacking SDS (25 mM tris, 192 mM glycine, pH 8.3, 0.1% Triton X-100, 3% DMSO) at 150 V cm$^{-1}$. Primary antibody probes were introduced in successive steps of electrophoretic loading and washout from the separation medium, 20 min for each step at 150 V cm$^{-1}$. Secondary antibodies were loaded and washed out for 10 min per step. Antibodies were 100 nM each in plain run buffer (mixed in a cocktail for multiplexed antigen detection) with 2 µM BSA for blocking purposes (no separate gel blocking step was necessary). Final green and red fluorescence channel imaging was performed for marker proteins and Micro-Western blot probe readout respectively. Enzyme amplified detection was carried out via electrophoretic introduction of fluorogenic DiFMUP phosphatase substrate (D6567, Invitrogen, Carlsbad, Calif.) at 600 V cm$^{-1}$, with blue DiFMU enzyme product imaged dynamically via a UV-longpass filter cube under stopped-field conditions. DiFMUP fronts required <30 s to transit Micro-Western devices, with signal development observed over 10-30 s periods. Since DiFMU product was also charged, immobilized analyte bands could be assayed multiple times by removing product electrophoretically between imaging cycles via 10 s field pulses at 600 V cm$^{-1}$. For HIV serum assays, primary antibody solution was replaced with 1:100 diluted serum in plain run buffer. All other steps were performed as described.

Reagents and Samples.

BPMAC monomer was synthesized and verified by 1H NMR and mass spectrometry as previously described in Example 1. Purified proteins, antibodies and fluorescence labeling protocols are described in Example 1.

Data Acquisition and Analysis.

Whole channel imaging at 10× was conducted via stitching of adjacent, overlapping CCD images in ImageJ (NIH, Bethesda, Md.) to produce full gel channel images and electropherograms.

Example 4

Microfluidic Separations for the Study of Molecule Switching

Introduction

Experiments were performed to study molecule switching during separations in microfluidic devices. In addition, experiments were performed to determine how specific protein mutations impact the coupled electrostatic and photophysical properties of the fluorescent proteins. Physicochemical properties, such as isoelectric point, governed the separations of molecules. When molecules switched states spontaneously or due to external stimuli, the properties governing the separation behavior also changed, resulting in different separation patterns. Properties such as the switching rates, as well as underlying physical mechanisms underlying the switching process were obtained from the separation patterns.

Time-resolved microfluidic isoelectric focusing (IEF) and in situ antibody blotting IEF were employed to monitor dark (non-fluorescent) and bright (fluorescent) protein populations of both wild-type *Aequorea victoria* (av) green fluorescent protein (GFP) and the E222G mutant *Aequorea coerulescens* (ac) GFP. Through IEF, each population was observed to exhibit distinct isoelectric points (pI) and, thus, distinct formal electrostatic charges. Interconversion between the dark and bright populations was controlled by differential exposure routines. The stoichiometry and kinetics of charge transfer tied to this reversible photobleaching process were determined. In concert with a reaction-transport model of bistable reversible charge and fluorescence photoswitching, the on-chip measurements of population interconversion rates indicated that both rheostatic and discrete switch-like modulation of the electrostatic charge of the proteins depending on the illumination profile was possible. Additionally, it was estimated that 3-4 formal charges distinguished the bright and dark populations of avGFP, compared to one charge for those of acGFP. Given the proposed role of E222 as a bridge between internal and exit hydrogen bond clusters within the GFP β-barrel, The difference in charge switching magnitude between the two mutants indicated the proton wire proton transport within the GFP structure, and proton exchange with the bulk solvent.

Experimental Procedures

Reagents and Materials

N-[3-[(4-Benzoylphenyl)formamido]-propyl]methacrylamide (BPMAC, C21H22N2O3, 350.2 g mol-1) monomer was synthesized via reaction of the succinimidyl ester of 4-benzoylbenzoic acid (323.3 g mol$^{-1}$; B1577, Invitrogen) with N-(3-aminopropyl)methacrylamide hydrochloride (178.7 g mol$^{-1}$; 21200, Polysciences, Warrington, Pa.) in the presence of catalytic triethylamine in dimethylformamide, purified, and characterized by 1H NMR and mass spectrometry. The monomer was added to BPMAC+ gel precursor solutions at 4.5 mM (~1 mol % with respect to acrylamide) from a 100 mM stock in dimethylsulfoxide (DMSO) to imbue UV-induced protein photocapture functionality. BPMAC− precursors were used in dynamic focusing experiments in which protein photocapture was not required and contained an equivalent volume of DMSO lacking BPMAC.

Purified recombinant wild-type GFP from *Aequorea Victoria* (avGFP) and the *Aequorea coerulescens* E222G mutant (acGFP) were from Clontech (632373 and 632502, Mountain View, Calif.). Intact mass analysis of GFP isoforms was performed by high-resolution electrospray-ionization liquid chromatography-mass spectrometry in a Thermo LTQ Orbitrap XL instrument at the QB3 Mass Spectrometry Facility at UC Berkeley. The primary goat polyclonal antibody to GFP was prelabeled with Texas Red by the manufacturer (dye:protein molar ratio=2.9; ab6660, Abcam, Boston, Mass.). Equal volumes of a set of fluorescent IEF pI markers with absorption maxima in the near-UV (pI 4.0, 4.5, 5.5, 6.2) were mixed in a cocktail and added to GFP samples at 20× dilution (89827 and related products, Sigma).

Microfluidic Chip Fabrication

Microchannels were wet etched in optical white soda lime glass by Caliper Life Sciences (Hopkinton, Mass.). Each chip contained four straight-channel devices 10.4 mm in length, each consisting of three parallel channels of 10 µm depth and 70 µm width between two 2 mm diameter access wells providing fluidic interfacing via 10 µL press-fit pipet tips. Microchannels were functionalized with acrylate-terminated self-assembled monolayers. Microfluidic gels were fabricated via introduction of a gel precursor solution by capillary action. The precursor contained 6% total acrylamide (6% T; % concentrations are w/v unless otherwise noted) with 2.6% of the total as the cross-linker bisacrylamide (2.6% C), 15% v/v polybuffer 74 ampholytes (P9652, Sigma, St. Louis, Mo.), 0.1% v/v Triton X-100 detergent (T8532, Sigma), and 4.5 mM BPMAC (see Reagents and Materials). The initiators ammonium persulfate (0.015%, A3678, Sigma), N,N,N',N'-tetramethylethylenediamine (0.05% v/v, T9281, Sigma), and riboflavin 5' phosphate (0.0006%, F1392, Sigma) were added just before introduction of degassed precursor to channels. The precursor was polymerized by 6 min flood exposure of chips to 470 nm blue light from a collimated LED source (M470L2, Thorlabs, Newton, N.J.) with access wells masked to restrict gelation to the microchannels. The blue light intensity at a 470 nm probe setting was ~2.2 mW cm-2 at the chip plane, as measured by a LaserCheck light meter (1098293, Coherent, Santa Clara, Calif.). Equivalent isoelectric photoswitching behavior was observed in gels chemically polymerized in the absence of riboflavin.

Apparatus and Imaging

Chip imaging was conducted using an Olympus IX71 inverted fluorescence microscope equipped with an EMCCD camera (iXon3 885, Andor, Belfast, Northern Ireland), motorized stage (Applied Scientific Instrumentation, Eugene, Oreg.), and automated filter cube turret controlled through MetaMorph software (Molecular Devices, Sunnyvale, Calif.). Illumination was provided by a mercury arc lamp mated to an automated shutter and attenuation system (X-Cite Exacte, Lumen Dynamics, Mississauga, ON, Canada). Electric field was applied via a custom high voltage power supply built in-house. Gel photoimmobilization of proteins was conducted via spot UV exposure through a 10× objective (Olympus UPIanFI, NA 0.3) and custom UV-long-pass filter cube (excitation 300-380 nm, emission >410 nm; XF1001, XF3097, Omega Optical) at ~269 mW cm$^{-2}$ as measured via a 365 nm probe (UV513AB meter, General Tools, New York, N.Y.). The same cube was used to observe GFP under UV illumination along with fluorescent pI marker peptides, and channel positions were manually scored (gradient drift between focused-state marker and GFP isoform imaging steps was assumed to be negligible). Green and red fluorescence channels were imaged at 10× using Omega Optical filter cubes optimized for GFP (XF100-3, excitation 445-495 nm at ~89 mW cm$^{-2}$ for a 470 nm probe setting, emission 508-583 nm) and DsRed2 (XF111-2, excitation 525-555 nm, emission >575 nm). Whole channel imaging at 10× magnification was conducted via stitching of adjacent, overlapping CCD images with 4×4 pixel binning in ImageJ (NIH, Bethesda, Md.) to produce full gel channel images and electropherograms. Imaging scans required ~20 s to complete. Real-time single-point imaging of GFP isoform dynamics was conducted in burst acquisition mode.

Transformation of fluorescence data via linear fits to pI markers and associated data processing, including correction for constant cathodic isoform drift velocities in dynamic focusing experiments was performed using MATLAB scripts written in-house (MathWorks, Natick, Mass.). Least-squares fitting of kinetic data was performed using gnuplot software.

Chip Operation

Figure 22:
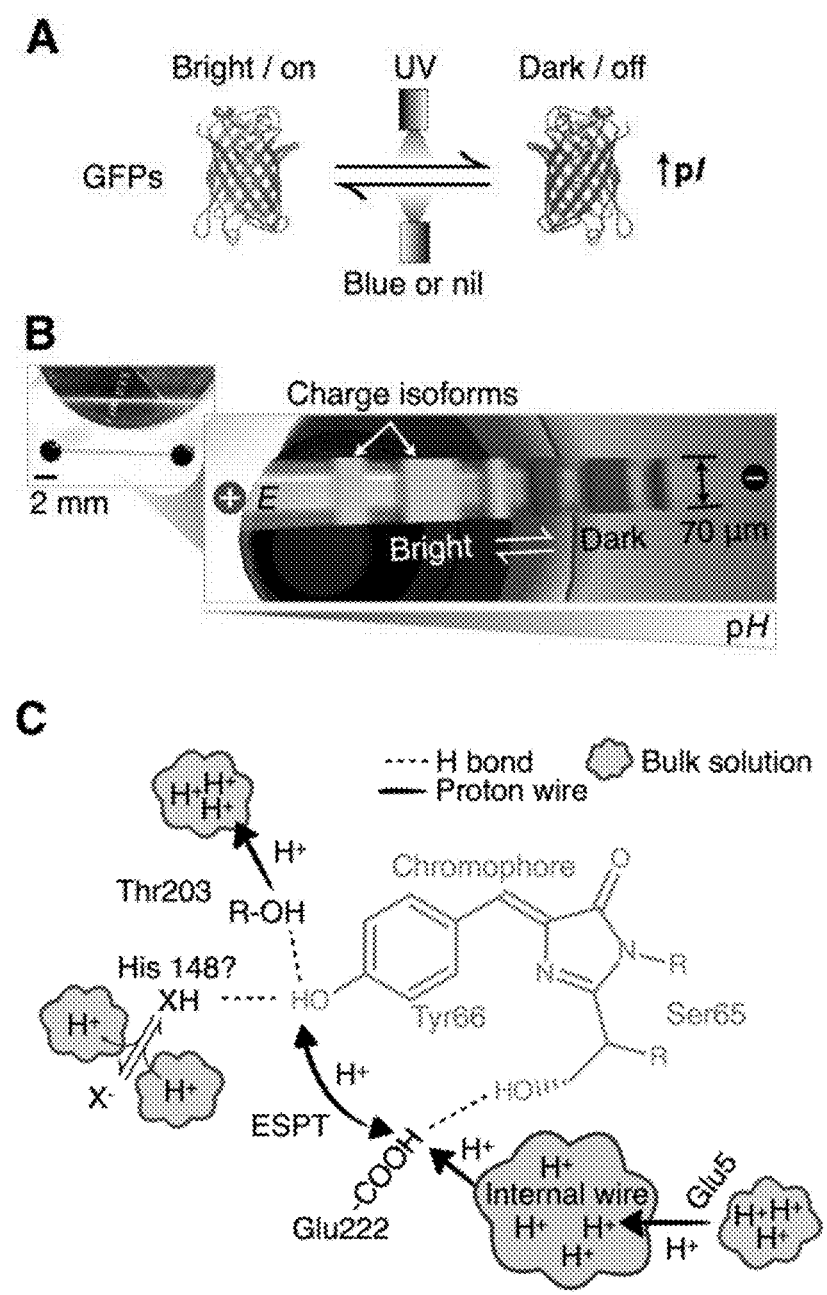
FIG. 22 shows immunoprobed isoelectric focusing, which allows dynamic and immunoreactivity-verified monitoring of GFP isoform dynamics during reversible photobleaching, according to embodiments of the present disclosure.

After precursor gelation, gel access wells were flushed and replaced with gel buffer consisting of precursor lacking monomers and initiators. Samples were made in gel buffer and introduced at loading wells (~3 µL per well). Sample injection was performed at 200 V cm$^{-1}$ for 3 min. Opposing wells were briefly washed with catholyte (20 mM lysine, 20 mM arginine pH 10.1) and anolyte (70 mM phosphoric acid pH 1.4) and subsequently filled. Focusing was conducted at 200 V cm$^{-1}$ for 2 min followed by 400 V cm$^{-1}$ for 1 min (focusing typically completed to equilibrium in 3 min or less). Imaging and UV photocapture steps (where applicable) were conducted individually for each device in series. UV photocapture was conducted under floating (halted) electric field for 15 s. Access wells were washed and filled with pH gradient mobilization/probe buffer consisting of 25 mM Tris, 192 mM glycine pH 8.3, 0.1% v/v Triton X-100, and 3% v/v DMSO. Mobilization and washout of pH gradients to the anodic wells was achieved via a 20 min electrophoretic step. Fluorescently labeled anti-GFP antibody was diluted in probe buffer, loaded, and removed from gels in 20 min electrophoretic steps. Probe loading and washout were conducted in opposite directions to minimize nonspecific signal remaining after washout. Finally, gels were scanned for captured GFP and antibody fluorescence. Removal of the gel matrix after use was achieved by overnight incubation of the chip in a 2:1 solution of 70% perchloric acid and 30% hydrogen peroxide heated to 75° C., allowing efficient recycling of glass chips General Utility and Demonstrated Applications Using dynamic IEF, dark (non-fluorescent) and bright (fluorescent) populations of avGFP and acGFP were observed and characterized by measuring changes in protein fluorescence and pI (FIG. 22). After IEF, an immunoblotting step was performed so that non-fluorescent analytes could be detected. Incubation of fluorescently labeled antibodies with IEF-resolved- and immobilized-proteins yielded pI and mass distribution for each target, including non-fluorescent forms of GFP. To immobilize proteins, IEF was performed in a light responsive benzophenone-decorated, polyacrylamide gel (light-activated volume-accessible separation gel). Brief exposure of the gel to UV light covalently attached proteins to the gel matrix, allowing subsequent protein probing via introduction of fluorescently labeled antibodies. The ability to blot and probe proteins with near-lithographic spatial control in direct series with controlled light pre-exposure sequences enabled quantitation in the absence of an endogenous fluorescence signal from the protein target. In the case of GFP, immunoblotting corroborated pI photoswitching measurements inferred from intrinsic fluorescence data. The GFP fluorescence signals had complex dependencies on light exposure history and chemical environment.

Figure 23:
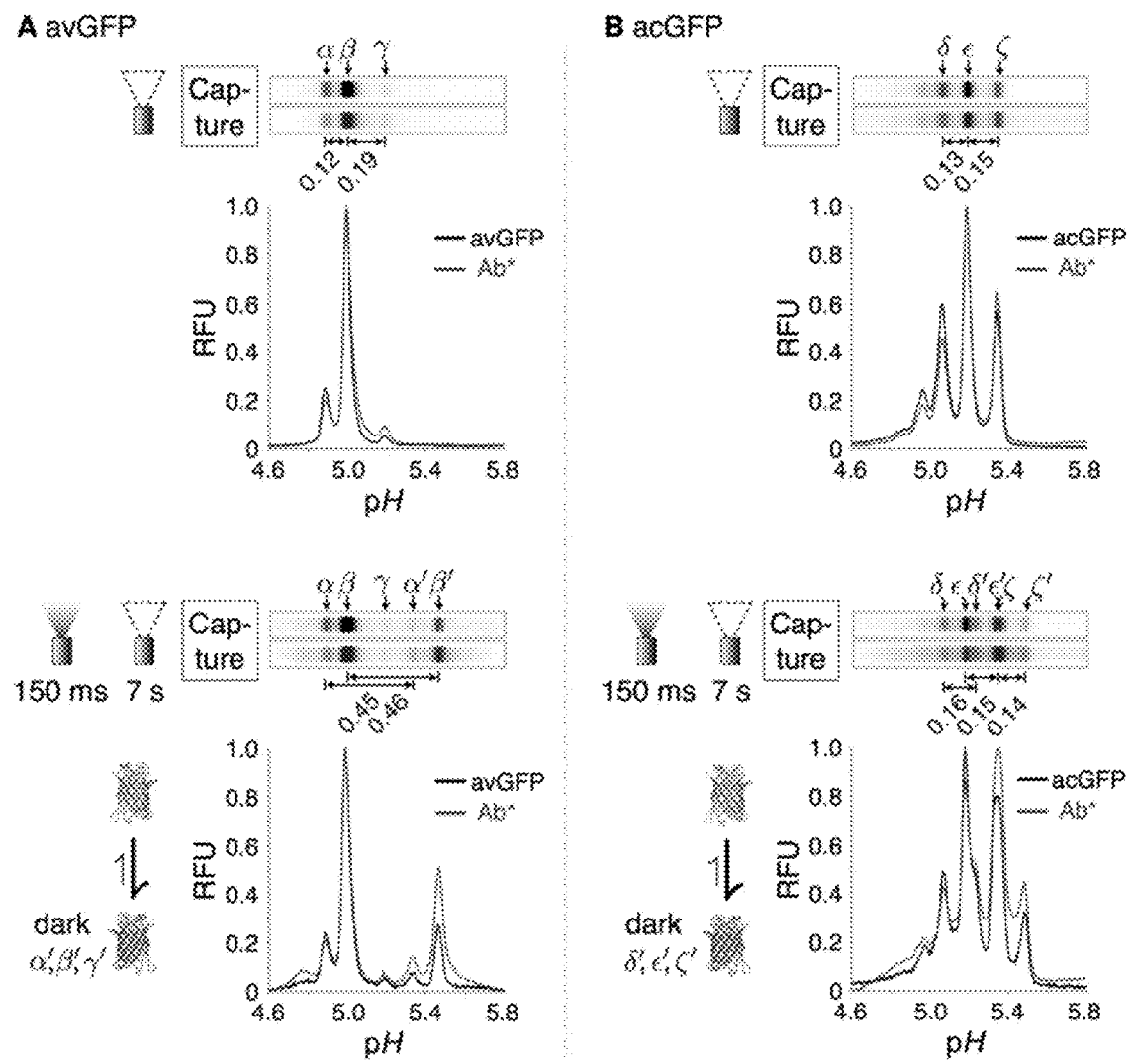
FIG. 23 shows probed isoelectric focusing of avGFP and acGFP, which shows the base-shifted reversibly photobleached isoforms, according to embodiments of the present disclosure.

IEF analysis yielded three predominant isoforms for each variant in the pI 4.8-5.5 range under continuous blue light excitation (isoforms were denoted α, β and γ for avGFP; and δ, ε and ζ for acGFP) (FIG. 23). These heterogeneous isoform patterns were ascribed to differential C-terminal cleavage by non-specific proteases during bacterial expression of the recombinant proteins. This difference was consistent with cleavage of the C-terminal lysine in the α isoform of avGFP. Given that the cleaved lysine residue contributed a full positive charge, the pI shift attributable to a single electrostatic charge was estimated at roughly 0.12-0.15 pH units from the relative bright isoform displacements in the pH axis of FIG. 23, and from further computational estimation of the expected isoform pIs resulting from differential C-terminal cleavage (data not shown). Thus, the magnitudes of isoelectric point photoswitching were calibrated using a ruler of electrostatic charge to allow direct inference of the stoichiometry of charge transfer events at single-charge resolution. The effect of charge transfer on the pI of a protein via its titration behavior had complex dependencies on, for example, the pI itself, and the molecular weight and amino acid composition of the protein. Thus, this "charge ruler" approximation was used under the assumption that the pI range over which charge shifts are estimated was narrow enough to assume a constant local slope in the charge vs. pH titration curve of the isoforms considered.

Figure 24:
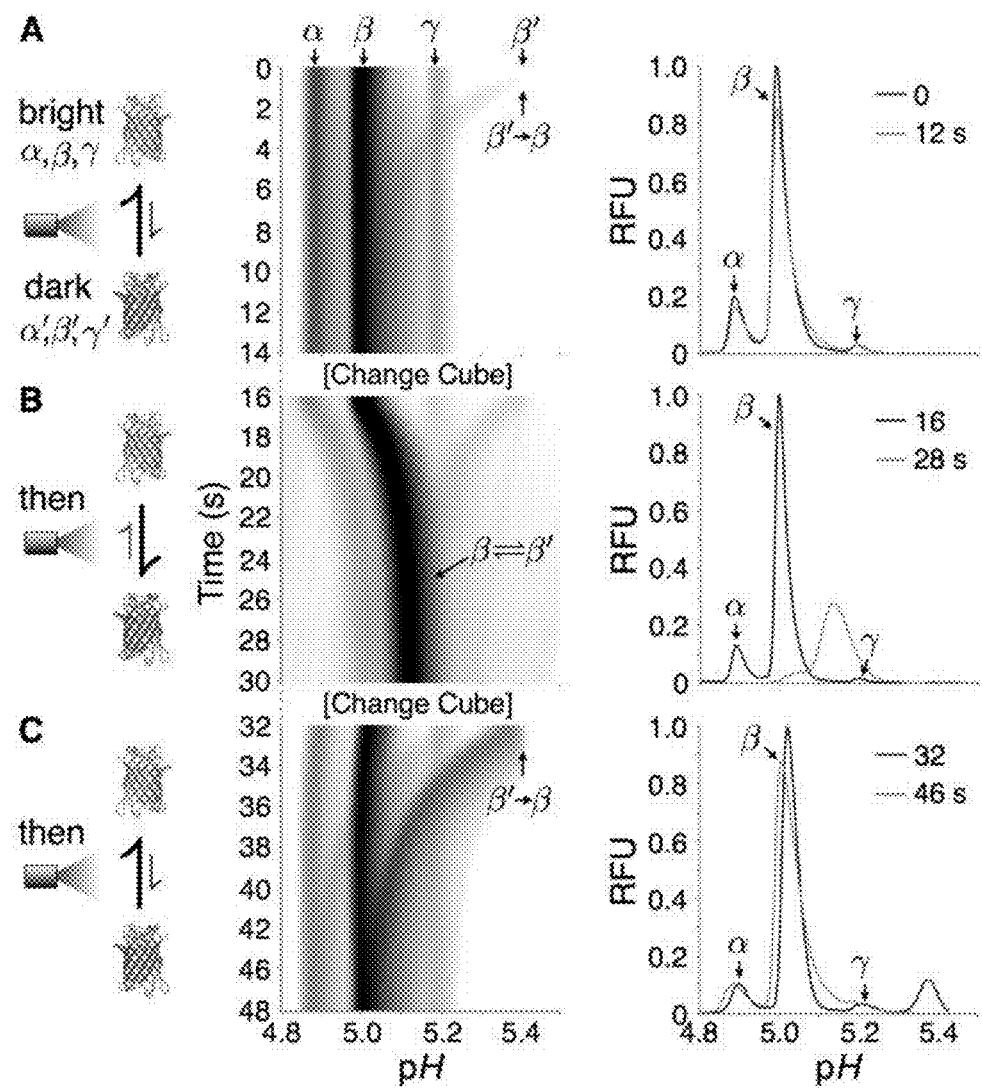
FIG. 24 shows real-time observation of isoelectric point photoswitching in avGFP, according to embodiments of the present disclosure.
Figure 25:
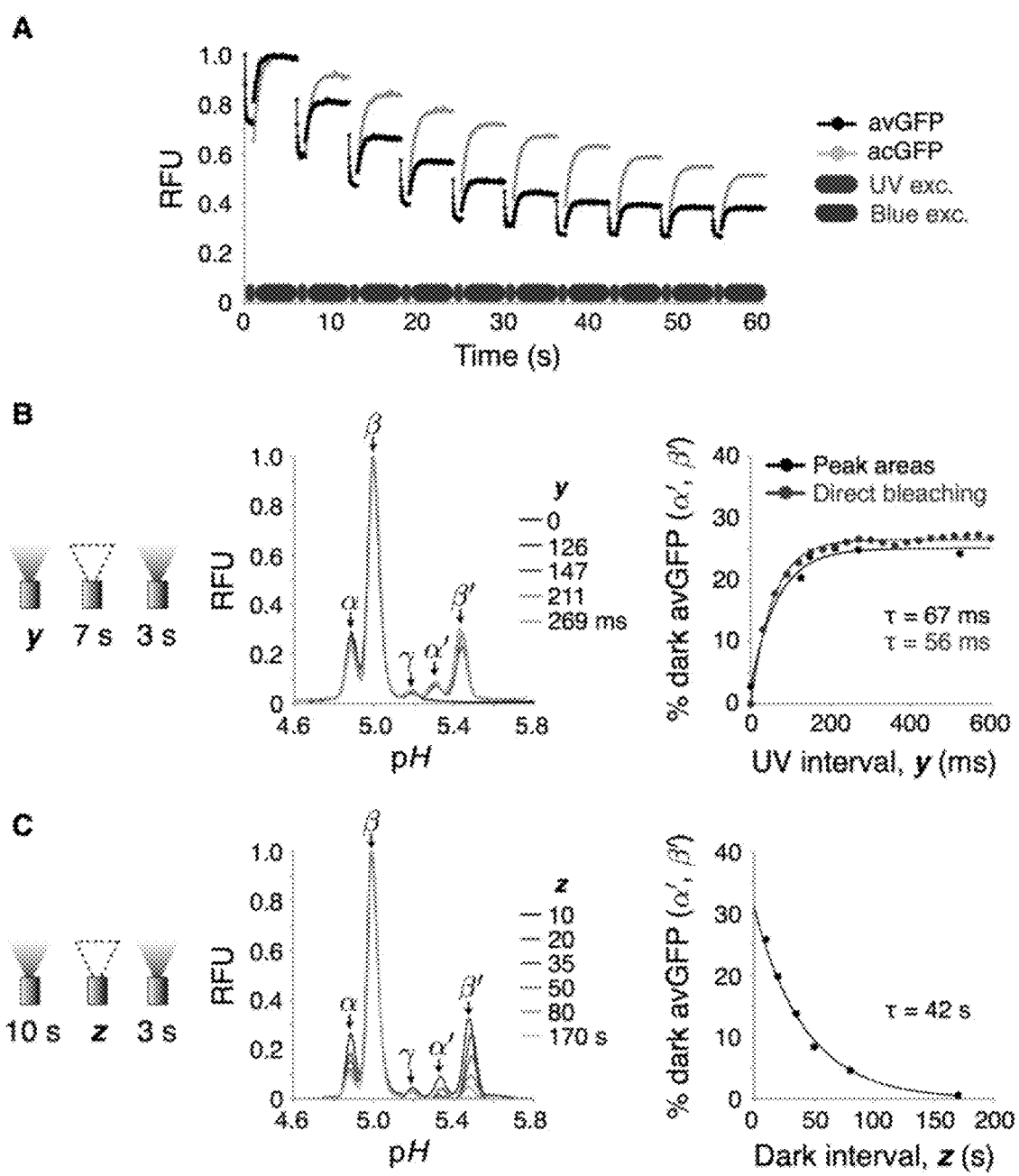
FIG. 25 shows isoelectric photoswitching kinetics, according to embodiments of the present disclosure.

Experiments were performed to investigate the effect of UV and blue light illumination on avGFP and acGFP isoform distributions during dynamic IEF. For both avGFP and acGFP, isoforms exhibited dynamic changes in isoelectric point distributions upon exposure of the focused proteins to sequences of UV and blue light illumination (FIG. 24). To summarize the observed photoswitching phenomena: brief exposure of the focused fluorescent isoform bands to UV light induced formation of dark (reversibly bleached) isoform populations with increased pI compared to bright isoforms (FIGS. 23-25). Following UV exposure, application of blue illumination initiated a dynamic "switch-on" of the fluorescence of the dark isoforms with first-order time constants of 700 ms for avGFP and 720 ms for acGFP (FIG. 24(A)). Concomitantly, migration of the switched-on isoforms to the pIs of their "parent" bright isoforms was observed on a ~5-10 s timescale. More prolonged exposure to UV on the focusing timescale caused a transient increase in the apparent pIs of bright isoforms to values intermediate between the static bright and dark isoform pIs. This apparent bright isoform pI increase reversed when UV illumination was halted (FIG. 24(B)), while dark isoforms assumed their higher pIs until blue light was applied (or until the dark isoforms relaxed back to the bright state during prolonged nil illumination).

Measurement of the dark isoform peak areas as a function of UV pre-exposure time revealed single-exponential switch-off kinetics with a time constant of 67 ms. This kinetic approximately matched the fast bleaching time constant of 56 ms under direct UV exposure of avGFP (FIG. 25(B)). These results indicated that reversible bleaching of bright GFP isoforms by UV exposure was the trigger for formation of dark state isoforms with alkaline-shifted pIs. The dark isoform populations, constituting ~25% of the total mass for avGFP after ≳150 ms UV exposure, also decayed back to the bright state under nil illumination conditions (FIG. 25(C)). The relatively short ~5-10 s focusing timescale (compared to the characteristic time of dark population decay) enabled resolution of dark from bright populations. This decay process was again described by single-exponential kinetics, with a time constant of 42.2 s for avGFP, which was similar to literature values of 58 and 54 s measured in mammalian cells for ECFP and EYFP respectively. Thus, blue photon absorption reduced the fluorescence switch-on time of reversibly bleached dark isoforms by a factor of ~60-fold (from 42 to 0.7 s) under the experimental conditions employed.

The distributions of the photoswitched isoforms may be related to the charge transfer events underlying the changes in isoelectric point. Two mutant-specific differences in these focusing behaviors were observed for avGFP and acGFP. Firstly, prolonged application of UV light caused apparent pI shifts of 0.12 and 0.10 units for all bright avGFP and acGFP isoforms respectively, as well as broadening of the focused zone band widths (4σ) by 2.47- and 1.24-fold respectively (as measured for the major β and ε isoforms, FIG. 24(B)). Secondly, the final pI shifts of each of the dark isoforms (e.g., β') from their parent bright bands (e.g., β) after halting illumination were ~0.45 and ~0.15 pI units for avGFP and acGFP respectively (~3-4 and ~1 charge units, FIG. 23). The fact that these bright-to-dark pI shifts were discrete, rather than spread over a distribution, indicated an all-or-nothing conversion process. Thus, the GFPs exhibited a bistable switch with respect to pI (at least on the fluorescence timescale) and with respect to fluorescence.

The GFP bistable switching was studied by modeling the isoelectric photoswitching of the predominant avGFP isoform between bright (β) and dark (β') states having distinct pIs. GFP molecules interconverted between these states according to an equilibrium reaction of the form β ⇌ β' with forward and backward rate constants of $k_{\beta \to \beta'}$ and $k_{\beta' \to \beta}$ respectively. The rate constants were determined by least squares fitting of the equilibrium bright population distributions obtained from the model to experimentally measured distributions. Focused avGFP isoform distribution fits were made across a range of UV illumination intensities. Governing equations for this model considered focusing and diffusive spreading of peaks (terms 1 and 2 on the right hand side of each equation), as well as first-order interconversion of bright and dark populations (terms 3 and 4):

$$\frac{dC_\beta}{dt} = p_\beta (x - x_{pI,\beta}) E_x \frac{dC_\beta}{dx} + D_\beta \frac{d^2 C_\beta}{dx^2} - k_{\beta \to \beta'} C_\beta + k_{\beta' \to \beta} C_{\beta'} \quad (1)$$

$$\frac{dC_{\beta'}}{dt} = p_{\beta'} (x - x_{pI,\beta'}) E_x \frac{dC_{\beta'}}{dx} + D_{\beta'} \frac{d^2 C_{\beta'}}{dx^2} - k_{\beta' \to \beta} C_{\beta'} + k_{\beta \to \beta'} C_\beta \quad (2)$$

Where C is concentration, t is time, x is distance along the separation axis, $p_\beta \approx p_{\beta'} = p$ is slope in analyte mobility with respect to x, E is applied electric field, and $D_\beta \approx D_{\beta'} = D$ is the diffusivity of GFP in the separation gel. Non-dimensionalization of the model with respect to the characteristic diffusion time between population peaks ($\Delta x_{pI}^2/D$) yielded three parameters 1) a Peclet number $Pe = p \Delta x_{pI}^2 E_x/D$, the ratio of diffusive and convective (focusing) timescales, 2) a Damkohler number $\kappa = k_{\beta \to \beta'} \Delta x_{pI}^2/D$, the ratio of diffusive and forward reaction timescales, and 3) an equilibrium constant $\gamma = k_{\beta' \to \beta}/k_{\beta \to \beta'}$, the ratio of backward and forward reaction rates.

Figure 26:
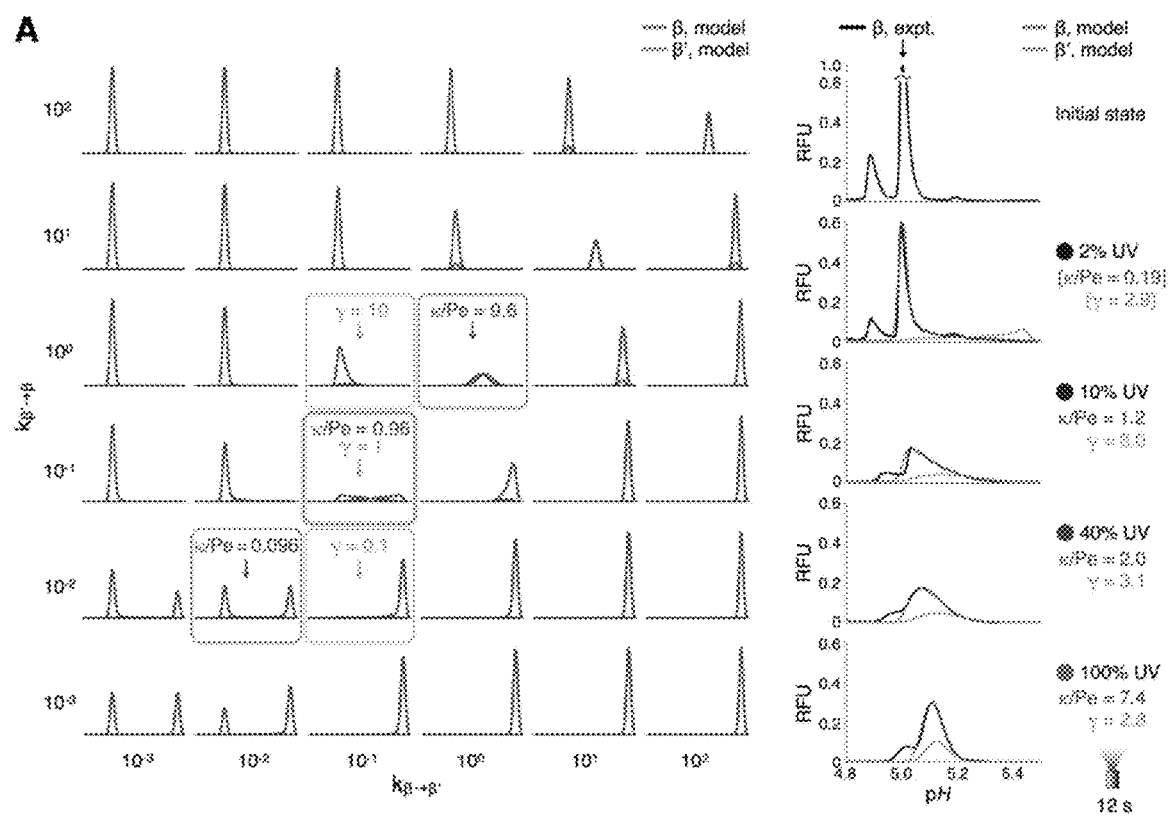
FIG. 26 shows two-state convection-diffusion-reaction model predicts focusing dynamics during perturbation of avGFP with UV light, according to embodiments of the present disclosure.

The dimensional analysis in FIG. 26(A) shows the diverse behavior of this convection-diffusion-reaction model. The reaction:focusing speed ratio κ/Pe and the equilibrium constant γ divide the ($k_{\beta \to \beta'}$, $k_{\beta' \to \beta}$) parameter space into several behavioral regimes that were directly mapped onto experimental data. At low UV intensities (κ/Pe<1), the bright and dark populations interchanged slowly enough compared to the focusing timescale that distinct bright and dark peaks were formed, producing a wide overall concentration distribution in the pI axis. As the UV intensity increased, the populations interchanged more rapidly, and the rate constants $k_{\beta' \to \beta}$ and $k_{\beta \to \beta'}$ increased at an approximately fixed ratio over the intensity range studied (γ~2.9, FIGS. 26(B) and (C)). Rapid interconversion caused the observed bright and dark distributions of the major avGFP isoform to converge along the pI axis at a weighted mean pH of 5.12 at $(pI_{\beta'} - pI_\beta)/(1+\gamma) = 0.12$ pH units from $pI_\beta = 5.00$, since $\gamma = C_\beta/C_{\beta'}$ at equilibrium. The 5-270 mW cm$^{-2}$ range in UV intensity studied produced an intensity-independent equilibrium in which each GFP molecule was bright with pI 5.00 around 74% of the time, and dark with pI 5.45 around 26% of the time. Increasing the UV intensity reduced the average time spent by a molecule in each state between switching events. Increases in each rate constant, and thus κ/Pe, accounted for the transitions in shape (wide to narrow) and position (lower pI to higher pI) of the observed bright isoform distributions, since the ability to resolve the bright and dark populations by focusing decreased as populations interconverted more and more rapidly.

Dynamic analysis over lower intensity ranges was limited by detection sensitivity, given that the GFP stimulation and imaging conditions were one and the same. Under nil illumination conditions, only the bright isoform populations existed (FIG. 23), which indicated a transition to the $\gamma_{avGFP}$ 2.9 equilibrium over the 0-5 mW cm$^{-2}$ UV intensity range and the ability to manipulate the mean avGFP pI from 5.00-5.12 in a rheostatic fashion. Similar fitting of experimental data for acGFP was confounded owing to a low fluorescence SNR caused by the heavily reduced UV absorbance in E222G mutants. However, assuming that the simple two-state model also holds for acGFP, the equilibrium bright distribution pI shift of 0.1 units at 100% UV yields $\gamma_{acGFP}$~0.5 at most, meaning that at least 67% of the acGFP was in the dark state at equilibrium.

The photophysics of the family of green fluorescent proteins derived from *Aequorea* sp. are characterized by an interconnection between spectral properties and short and long-range proton dynamics involving their chromophores. The diversity of photophysical characteristics of the fluorescent proteins indicate a complex interconnection between pH-dependent and -independent protonation equilibria, proton exchange with the bulk solvent ENREF 51, chromophore and pocket residue conformation, electrostatic interactions between the chromophore and surrounding residues in the chromophore pocket, and irreversible chemical reactions at the chromophore or surrounding residues; all of which contribute to the divergent absorption, emission, photoactivation and reversibility aspects of the fluorescence of GFP family members.

Experiments were performed to study the UV intensity-dependent IEF focusing behavior of GFP isoforms at the ensemble level by determining the interplay between reaction and transport timescales. Specific to the GFP studies conducted here, the wild type *Aequorea victoria* avGFP, a β-barrel structure containing a buried tripeptide chromophore formed autocatalytically from Ser65, Tyr66 and Gly67, exhibited fluorescence with absorption bands at both ~400 and ~475 nm. These absorption bands included two subpopulations A and B having, respectively, neutral (protonated) and anionic (deprotonated) charge at the hydroxyl group of Tyr66 of the buried chromophore. While the neutral A form dominated B by 6:1 in wild-type avGFP, S65T (e.g., EGFP) and E222G (e.g., acGFP, a modified GFP from *Aequorea coerulescens*) mutants favored the anionic B state in the physiological pH range, thus suppressing the 404 nm absorption peak and simplifying their photophysical behavior. Picosecond spectroscopy studies indicated an excited-state proton transfer (ESPT) process that occurred upon excitation of the protonated A state, which caused the phenolic proton at Tyr66 to delocalize and transfer to Glu222 via a network of hydrogen bonds due to a drop in the $pK_a$ of the tyrosyl phenol in the excited state.

The isoelectric point photoswitching in avGFP indicated the arrangement of the switching wavelengths (higher energy light shifts equilibrium towards dark state; lower energy light hastens fluorescence recovery), kinetic parameters, and GFP variants studied. The P and $B_r$ fluorescence states were characterized by distinct electrostatic charge states at the whole molecule level via direct physicochemical measurement with dynamic IEF. These distinct electrostatic charge states indicated proton exchange with the bulk solvent. The polarity of the observed pI shifts further indicated that the transition of GFPs to the dark state involved proton uptake into their structures (causing increased pI), and vice versa, that the return to the bright state involved expulsion of protons (causing decreased pI). Thus, the observations of single-charge resolution pI indicated that at least one proton uptake event occurred for the P to $B_r$ transition, although the specific residue(s) involved in this process were not identified via the whole molecule-level measurements of electrostatic charge made here. However, the observed difference in protonation stoichiometry between avGFP and acGFP may indicate structural rearrangements underlying the reversible bleaching process.

Specifically, the all-or-nothing uptake of 3-4 protons by avGFP isoforms during fluorescence switch-off may indicate a cascade of rearrangements in the proposed internal hydrogen bonding network buried within the avGFP structure extending from the chromophore pocket beyond the E222 bridge. For example, there may be multiple proton storage within the GFP structure at buried hydronium ions and titratable residues. Given that proton travel between the proposed internal and exit hydrogen bond clusters was expected to be restricted or rerouted by the E222G mutation in acGFP, the single-charge shift between bright and dark states observed for the acGFP isoforms may result from titration dynamics restricted to the chromophore pocket that were facilitated by acid-induced protonation of a pocket residue that governs transition between the bright P and dark $B_r$ states.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of assaying molecule switching, the method comprising:
    separating a sample comprising a molecule using a microfluidic device to obtain a separation pattern, wherein the microfluidic device comprises a separation medium comprising functional groups that covalently bond to the molecule upon application of electromagnetic radiation and the method further comprises applying the electromagnetic radiation to the separation medium to covalently bond the molecule to the separation medium;
    detecting a first separation pattern of the molecule in a first state of a switching characteristic of the molecule;
    applying an external stimulus to the molecule such that the molecule changes from the first state of the switching characteristic to a second state of the switching;
    detecting a second separation pattern of the molecule in the second state of the switching characteristic of the molecule; and
    determining a change between the first separation pattern and the second separation pattern to assay the switching characteristic of the molecule.

2. The method according to claim 1, further comprising contacting the separation medium with a label that specifically binds to the molecule covalently bound to the separation medium.

3. The method according to claim 2, further comprising detecting the label.

4. The method according to claim 3, wherein the label comprises a labeled antibody.

5. The method according to claim 1, wherein the molecule is a protein.

6. The method according to claim 5, wherein the protein is a fluorescent protein.

7. The method according to claim 6, wherein the switching characteristic is a photoswitching characteristic.

8. The method according to claim 7, wherein the photoswitching characteristic is a change between fluorescent and non-fluorescent states.

9. The method according to claim 8, wherein the method includes determining a rate of photoswitching between fluorescent and non-fluorescent states.

10. The method according to claim 8, wherein the method includes determining a mechanism of photoswitching between fluorescent and non-fluorescent states.

11. The method according to claim 1, wherein the sample is microfluidically separated using an equilibrium separation technique.

12. The method according to claim 11, wherein the equilibrium separation technique comprises isoelectric focusing.

13. The method according to claim 1, wherein the sample is microfluidically separated using a non-equilibrium separation technique.

14. The method according to claim 13, wherein the non-equilibrium separation technique comprises gel electrophoresis.

15. The method of claim 1, wherein determining a change between the first separation pattern and the second separation pattern comprises determining a kinetic property of the switching characteristic of the molecule.

16. The method of claim 1, wherein determining a change between the first separation pattern and the second separation pattern comprises determining a mechanism of the switching characteristic of the molecule.

17. The method of claim 1, wherein the microfluidic device comprises an elongated flow path.

18. The method of claim 17, wherein the separation medium comprises a polymeric gel substantially filling an interior volume of the elongated flow path after application of electromagnetic radiation such that the sample comprising the molecule traverses the separation medium as the sample flows through the elongated flow path.

19. A system for assaying molecule switching, the system comprising:
    (a) a microfluidic device comprising a separation medium configured to separate a sample comprising a molecule to obtain a separation pattern, wherein the separation medium comprises functional groups that covalently bond to the molecule upon application of electromagnetic radiation and the system is configured to apply the electromagnetic radiation to the separation medium to covalently bond the molecule to the separation medium; and
    (b) a processor programmed to determine a switching characteristic of the molecule from a change between a first separation pattern and a second separation pattern of the sample,
    wherein the system is further programmed to:
        detect a first separation pattern of the molecule in a first state of the switching characteristic of the molecule;
        apply an external stimulus to the molecule such that the molecule changes from the first state of the switching characteristic to a second state of the switching characteristic;
        detect a second separation pattern of the molecule in the second state of the switching characteristic; and
        determine a change between the first separation pattern and the second separation pattern to assay the switching characteristic of the molecule.

20. The system according to claim 19, further comprising a source of electromagnetic radiation.

21. The system according to claim 20, wherein the electromagnetic radiation source is a light source.

22. The system of claim 19, wherein the microfluidic device comprises an elongated flow path.

23. The system of claim 22, wherein the separation medium comprises a polymeric gel substantially filling an interior volume of the elongated flow path after application of electromagnetic radiation such that the sample comprising the molecule traverses the separation medium as the sample flows through the elongated flow path.

24. A kit comprising:
(a) system for assaying molecule switching according to claim 19; and
(b) a buffer.

* * * * *